(12) United States Patent
Voigt et al.

(10) Patent No.: US 8,828,658 B2
(45) Date of Patent: Sep. 9, 2014

(54) SPATIO-TEMPORAL CONTROL OF PROTEIN INTERACTIONS USING PHYTOCHROMES

(75) Inventors: Christopher A. Voigt, Oakland, CA (US); Anselm Levskaya, Oakland, CA (US); Wendell Lim, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 760 days.

(21) Appl. No.: 12/993,702

(22) PCT Filed: May 26, 2009

(86) PCT No.: PCT/US2009/045204
§ 371 (c)(1),
(2), (4) Date: May 3, 2011

(87) PCT Pub. No.: WO2009/151948
PCT Pub. Date: Dec. 17, 2009

(65) Prior Publication Data
US 2011/0207116 A1 Aug. 25, 2011

Related U.S. Application Data

(60) Provisional application No. 61/055,783, filed on May 23, 2008.

(51) Int. Cl.
*C12Q 1/68* (2006.01)
*C12N 5/00* (2006.01)

(52) U.S. Cl.
CPC .............. *C12N 5/00* (2013.01); *C12N 2529/10* (2013.01)
USPC .............. 435/6.1; 435/29; 435/325; 530/379; 536/23.6; 536/24.1

(58) Field of Classification Search
None
See application file for complete search history.

(56) References Cited

U.S. PATENT DOCUMENTS

2003/0082809 A1 5/2003 Quail et al.
2005/0277116 A1 12/2005 McKeon et al.

FOREIGN PATENT DOCUMENTS

WO 2009/151948 A2 12/2009

OTHER PUBLICATIONS

Khanna, R. et al. A Novel Molecular Recognition Motif Necessary for Targeting Photoactivated Phytochrome Signaling to Specific Basic Helix-Loop-Helix Transcription Factors. The Plant Cell. Nov. 2004, vol. 16(11), pp. 3033-3044.
Krall, L. et al. The Histidine Kinase-Related Domain Participates in Phytochrome B Function but is Dispensable. PNAS. Jul. 2000, vol. 97(14), pp. 8169-8174.

*Primary Examiner* — Jim Ketter
(74) *Attorney, Agent, or Firm* — Kilpatrick Townsend & Stockton LLP

(57) ABSTRACT

The invention provides methods, materials and systems of regulating association between proteins of interest using light. In an aspect, the invention takes advantage of the ability of phytochromes to change conformation upon exposure to appropriate light conditions, and to bind in a conformation-dependent manner to cognate proteins called phytochrome-interacting factors. The invention comprises a method of regulating interaction between a first protein of interest and second protein within a cell by light. Such a method optionally comprises providing in the cell (1) a first protein construct which comprises the first protein, a phytochrome domain (PHD), and (2) providing in the cell a second protein construct which comprises the second protein and a phytochrome domain-interacting peptide (PIP) that can bind selectively to the Pfr state, but not to the Pr state, of the phytochrome domain.

20 Claims, 14 Drawing Sheets

Figure 1

A) Sequence of Arabidopsis thaliana PhyB full length

MVSGVGGSGGGRGGGRGGEEEPSSSHTPNNRRGGEQAQSSGTKSLRPRSNTESMSKAI-
QQYTVDARLHAVFEQSGESGKSFDYSQSLKTTTYGSSVPEQQITAYLSRIQRGGYIQPFGCMIAVD
ESSFRIIGYSENAREMLGIMPQSVPTLEKPEILAMGTDVRSLFTSSSSILLERAFVAREITLLNPVWIH
SKNTGKPFYAILHRIDVGVVIDLEPARTEDPALSIAGAVQSQKLAVRAISQLQALPGGDIKLLCDTV
VESVRDLTGYDRVMVYKFHEDEHGEVVAESKRDDLEPYIGLHYPATDIPQASRFLFKQNRVRMIV
DCNATPVLVVQDDRLTQSMCLVGSTLRAPHGCHSQYMANMGSIASLAMAVIINGNEDDGSNVA
SGRSSMRLWGLVVCHHTSSRCIPFPLRYACEFLMQAFGLQLNMELQLALQMSEKRVLRTQTLLCD
MLLRDSPAGIVTQSPSIMDLVKCDGAAFLYHGKYYPLGVAPSEVQIKDVVEWLLANHADSTGLST
DSLGDAGYPGAAALGDAVCGMAVAYITKRDFLFWFRSHTAKEIKWGGAKHHPEDKDDGQRMH
PRSSFQAFLEVVKSRSQPWETAEMDAIHSLQLILRDSFKESEAAMNSKVVDGVVQPCRDMAGEQ
GIDELGAVAREMVRLIETATVPIFAVDAGGCINGWNAKIAELTGLSVEEAMGKSLVSDLIYKENEAT
VNKLLSRALRGDEEKNVEVKLKTFSPELQGKAVFVVVNACSSKDYLNNIVGVCFVGQDVTSQKIV
MDKFINIQGDYKAIVHSPNPLIPPIFAADENTCCLEWNMAMEKLTGWSRSEVIGKMIVGEVFGSC
CMLKGPDALTKFMIVLHNAIGGQDTDKFPFPFFDRNGKFVQALLTANKRVSLEGKVIGAFCFLQIP
SPELQQALAVQRRQDTECFTKAKELQDTECFTKAKELQSGMRFANSLQDTECFTKAKELQDTECF
TVSCEKQISRIVGDMDLESIEDGSFVLKREEFFLGSVINAIVSQFMFLLRDRGLQLIRDIPEEIGLQLIR
DIPEQIRIQQLLAEFLGLQLIRDIPEEIGLQLIRDSQLGLQLIRDIPEEIGLQLIRDACPGEGLPPELVRD
MFHSSRWTSPEGLGLSVCRKILKLMNGEVQYIRESERSYFLIILELPVPRKRPLSTASGSGDMMLM
MPY*

Figure 2 (contd).
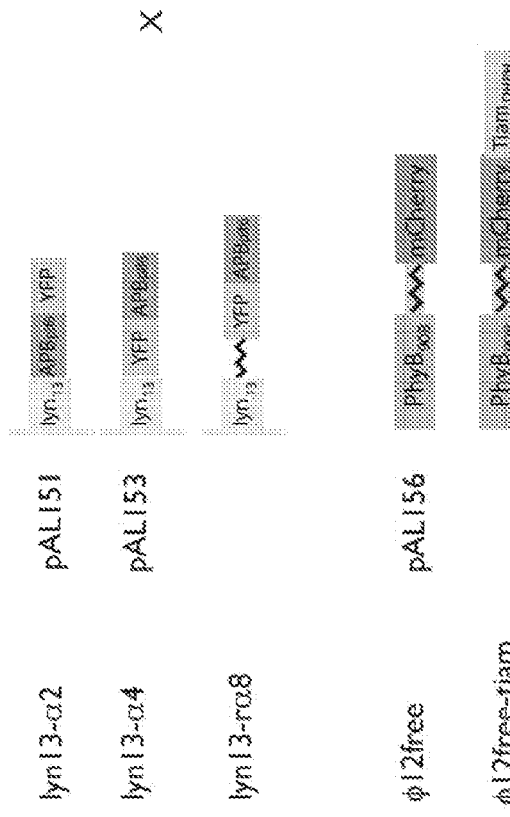

Figure 3 Control of Association with Light

A Phytochrome - PIF Interaction

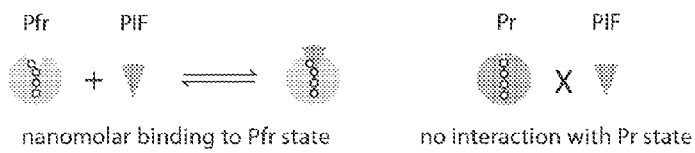

nanomolar binding to Pfr state    no interaction with Pr state

Phytochrome Interaction Factors (PIFs) exhibit strong (~nM) *selective* binding to the ON state of Phytochrome.

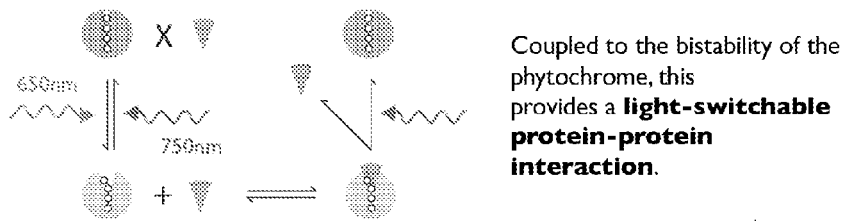

Coupled to the bistability of the phytochrome, this provides a light-switchable protein-protein interaction.

B Association Test Schematic

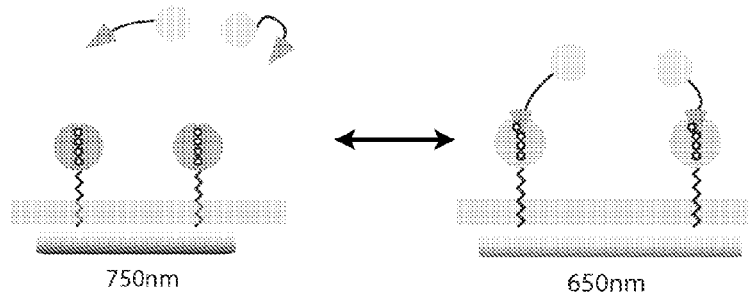

750nm    650nm

C Cytoplasmic Depletion Demonstrates Association

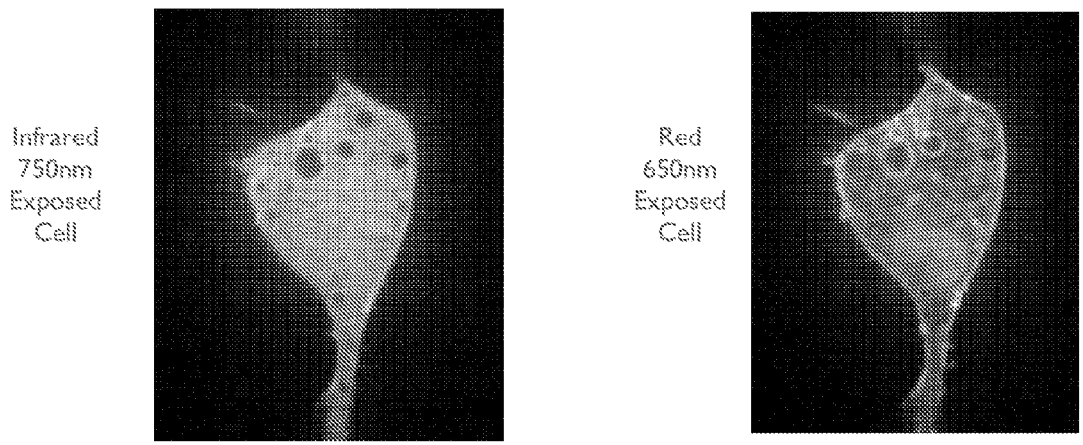

Infrared 750nm Exposed Cell    Red 650nm Exposed Cell

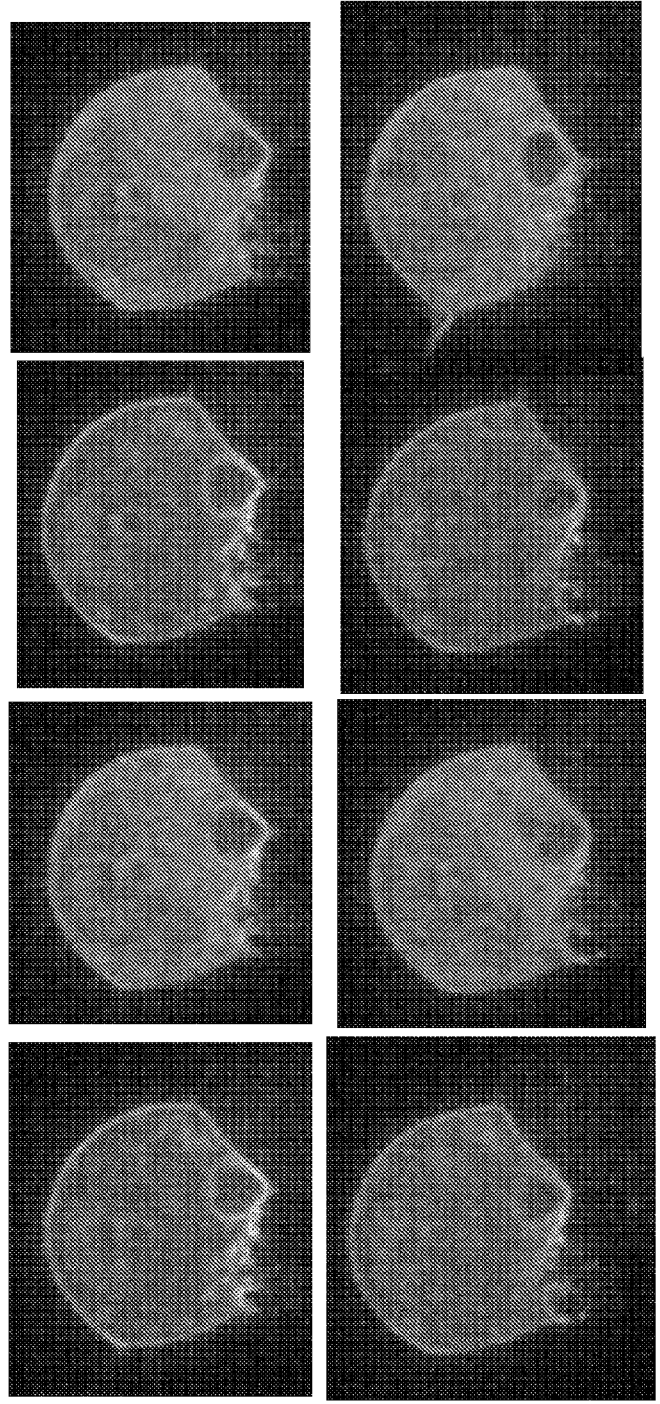

Figure 5 Localized Association Controlled with Light
A  Point stimulation of Red, IR stimulation everywhere
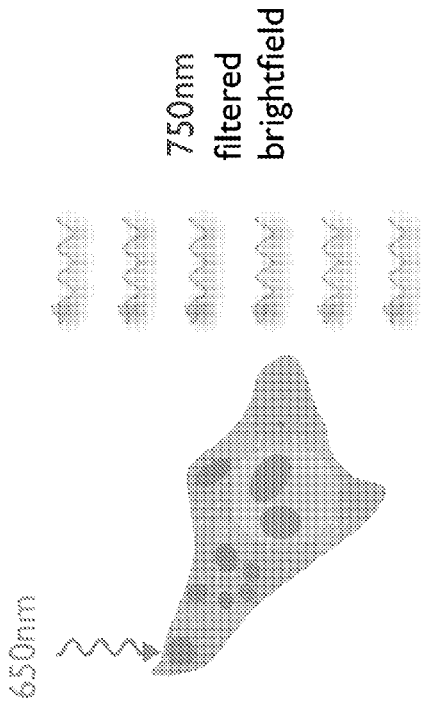
B  Example of localized YFP moving with light
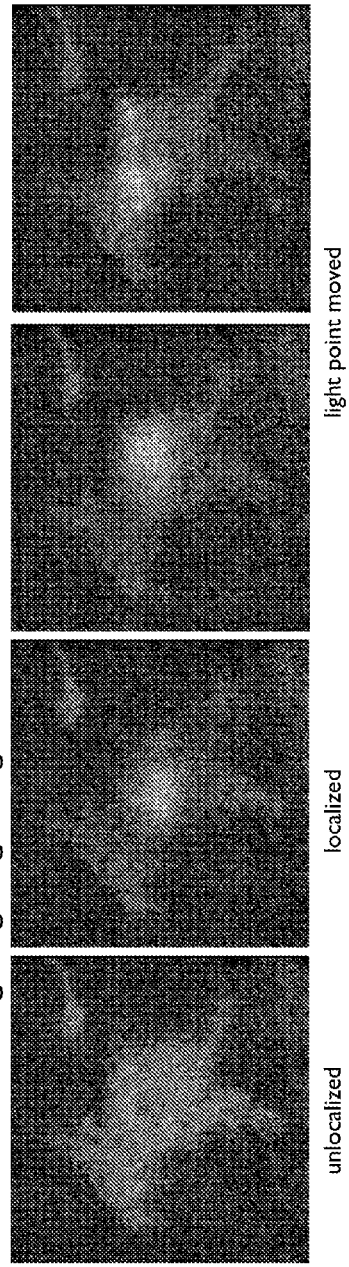

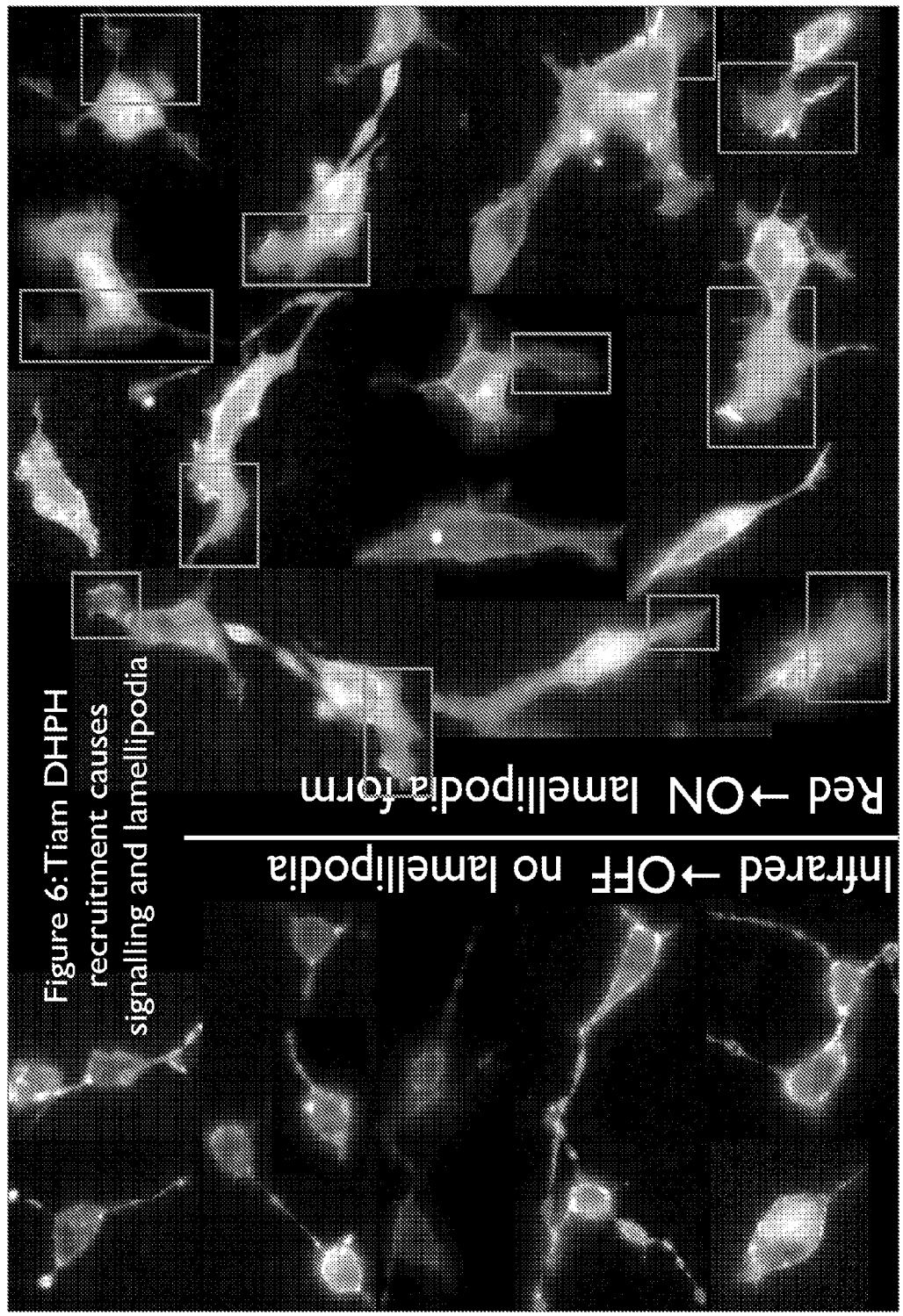

Figure 7 Spatiotemporal Control of Signalling with Light

A  Localized Recruitment Schematic

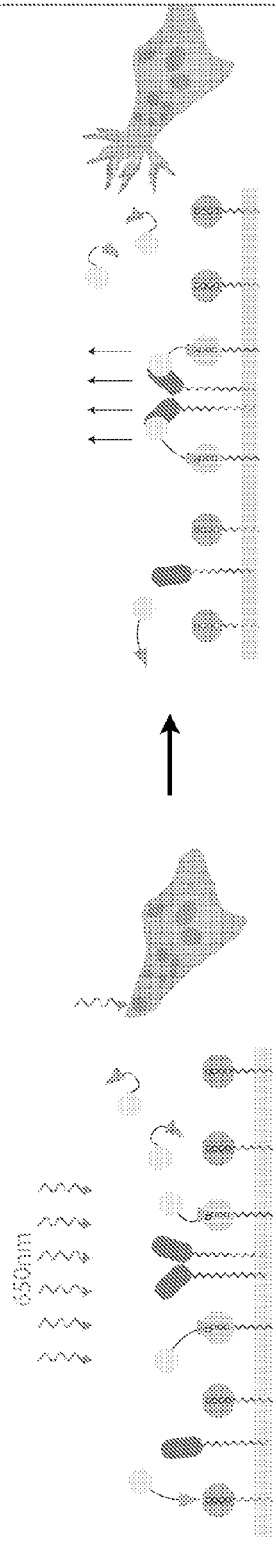

ON phytochromes recruit signalling molecule -locally- via PIF domain.
Signalling domains are then recruited to this patch and interact with their downstream signaling partners, inducing signalling locally in a temporally regulated manner.

B  Induction of Lamellipodia by Tiam recruitment

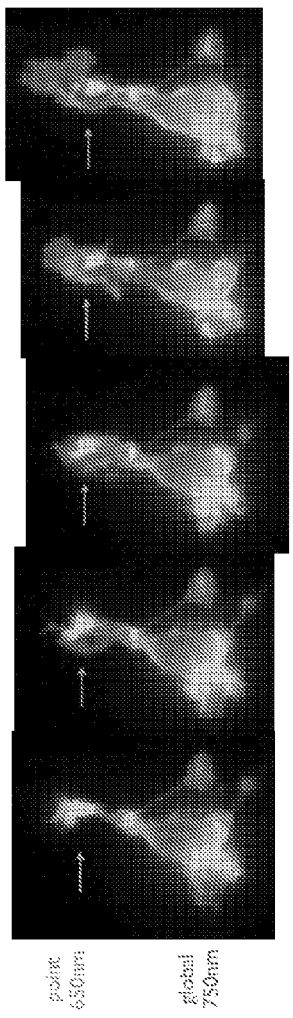

Spatial Localization of Activity induction is the most stringent test of the system's ability: it requires rapidly reversible OFF and ON recruitment to compensate for diffusive drift of recruited signalling molecules.

Here, a point stimulation against a global background locally induces a lamellipodia in a 3T3 fibroblast-like cell.

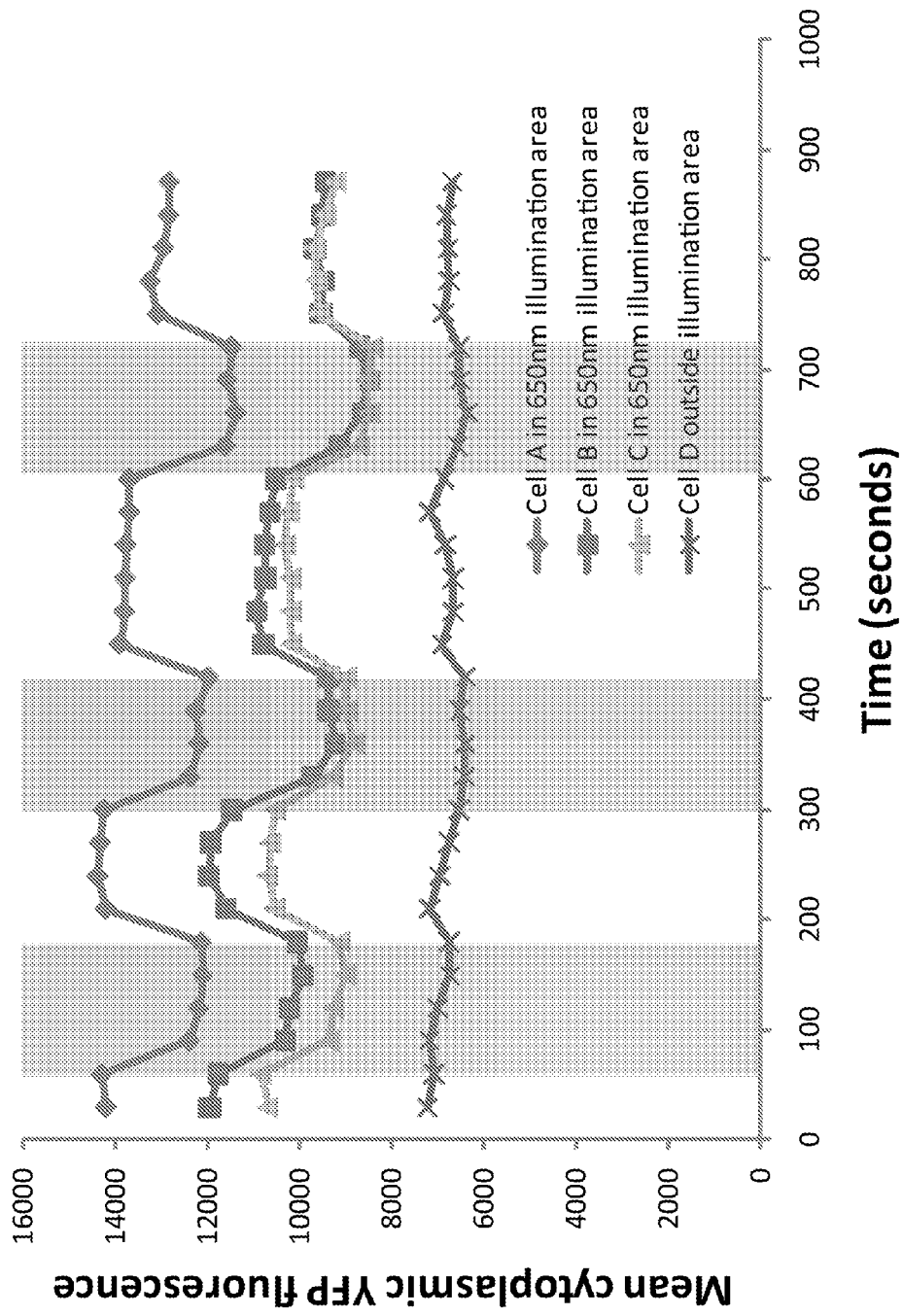

US 8,828,658 B2

SPATIO-TEMPORAL CONTROL OF PROTEIN INTERACTIONS USING PHYTOCHROMES

This application claims the benefit of U.S. Provisional App. No. 61/055,783 filed May 23, 2008, incorporated by reference in its entirety for all purposes.

STATEMENT AS TO RIGHTS TO INVENTIONS MADE UNDER FEDERALLY SPONSORED RESEARCH AND DEVELOPMENT

Research was done with the help of Federal Grant Number NIH/PN2EY016546 and NSF Graduate Fellowship No. 2005030582. The United States Government has certain rights in the invention.

BACKGROUND OF THE INVENTION

Systems for controlling protein interactions have a variety of experimental and commercial applications. The majority of such systems that have been developed are based on the administration of chemical effectors which require diffusion into the cell to provide appropriate, non-toxic concentrations of chemical at the dimer-interface site. In an alternative strategy, attempts have been made to use light to regulate protein interactions. See, e.g., Leug et al., PNAS, Sep. 2, 2008, vol. 105, no. 35, 12797-12802; Shimizu-Sato et al., Nature Biotech. Vol. 20, page 1041-44 (2002); Tyszkiewicz et al., Nature Methods, Vol. 5, No. 4 (2008), p. 303-305.

The phytochromes comprise a family of biliprotein photoreceptors that enable plants to adapt to their prevailing light environment (Kendrick and Kronenberg (1994) Kendrick, Pp. 828 in Photomorphogenesis in Plants, Dordrecht, The Netherlands: Kluwer Academic Publishers). Phytochromes possess the ability to efficiently photointerconvert between red light absorbing Pr and far red light absorbing Pfr forms, a property conferred by covalent association of a linear tetrapyrrole (bilin or phytobilin) with a large apoprotein. Phytochromes from cyanobacteria, to green algae and higher plants consist of a well conserved N-terminal polypeptide, roughly 390-600 amino acids in length (see, e.g. U.S. Pat. No. 6,046, 014), to which the phytobilin prosthetic group, e.g., phytochromobilin (PΦB) or phycocyanobilin (PCB) is bound.

BRIEF SUMMARY OF THE INVENTION

The invention provides methods of spatially and/or temporally regulating an interaction between a first protein sequence and a second protein sequence within a cell by light. Such methods can for example comprise: (a) providing in the cell a first protein construct which comprises the first protein sequence and a phytochrome domain (PHD), (b) providing in the cell a second protein construct which comprises the second protein sequence and a phytochrome domain-interacting peptide (PIP) that can bind selectively to the Pfr state, but not to the Pr state, of the phytochrome domain; and (c) regulating the interaction between the first protein construct and the second protein construct by regulating cell exposure to red light and/or infra-red light. Optionally, the methods can further comprise detecting a change in the interaction between the first protein construct and the second protein construct within the cell.

The phytochrome domain can optionally convert from a red-light absorbing conformer (Pr state) to a far-red light-absorbing conformer (Pfr state) upon exposure to red light. The PHD can also optionally convert from the Pfr state to the Pr state upon exposure to infra-red light. Either or both conversions can be reversible. The red light for example has a wavelength of about 650 nm. The infra-red light for example has a wavelength of about 730 nm.

Optionally, the PHD comprises a partial fragment of PhyB from *Arabidopsis thaliana*, and the PIP comprises the APB domain of PIF6; and/or the cell is a mammalian cell. If so desired, the first protein construct or second protein construct can be optically (e.g., visually) detected, and the change in interaction is detected by visually detecting its spatial distribution. The change in interaction can be optionally detected within one minute of exposure to regulatory red or infra-red light. In an embodiment, a portion of the cell is exposed to regulatory red or infra-red light and the change in interaction is spatially localized within a few microns of the exposed portion.

In an embodiment, at least one of the protein constructs can comprise a subcellular localization tag (SLT), whereby the protein construct is localized to a subcellular compartment. At least one of the protein constructs can comprise a detectable label. For example, one protein construct can comprise a SLT whereas the other can comprise a detectable label, whereby interaction between both protein constructs upon exposure to red light results in recruitment of the detectable label to the subcellular compartment. Optionally, the label can be optically detected.

In such methods, the phytochrome domain can for example be initially converted to (i) the Pr state, thereby disallowing the interaction between the first protein construct and the second protein construct; or (ii) the Pfr state, thereby allowing the interaction between the first protein construct and the second protein construct. For example, the phytochrome domain is converted to (i) the Pr state by exposing the cell to infra-red light, or (ii) the Pr state by exposing the cell to red light, or vice versa.

Optionally, the phytochrome domain, if initially converted to the Pr state, is subsequently converted to the Pfr state, thereby allowing or inducing any interaction between the first protein construct and second protein construct. If initially converted to the Pfr state, the PHD is optionally subsequently converted to the Pr state, thereby disallowing or discontinuing any interaction between the first protein construct and second protein construct. The phytochrome domain is subsequently converted to the Pfr state for example by exposing the cell to red light, or to the Pr state by for example exposing the cell to infrared light.

The phytochrome domain is for example derived from *Arabidopsis thaliana* PhyB. Optionally, the PHD can include the chromophore-binding domain and C-terminal tandem PAS domains of PhyB. The PIP can for example be derived from the activated phytochrome B-binding domain (APB) of PIF6. The cell is for example a yeast, insect, avian or mammalian cell. Optionally, neither the first protein sequence nor the second protein sequence is a transcriptional regulator. The first or second protein sequence is optionally a signaling polypeptide.

The invention also includes isolated or recombinant cells (e.g., mammalian cells) comprising a first and a second protein construct, and/or one or more nucleic acids encoding said first and second protein constructs. The first protein construct for example comprises a first protein sequence of interest and an activated phytochrome B-binding domain (APB) of PIF6; and the second protein construct for example comprises a second protein sequence of interest and a phytochrome domain from PhyB of *A. thaliana*. The phytochrome domain can for example convert in a fully photo-reversible manner from a red-light absorbing conformer (Pr state) to a far-red light-absorbing conformer (Pfr state) upon exposure to red light, and/or can convert in a fully photo-reversible manner from the Pfr state to the Pr state upon exposure to infra-red light. The PHD optionally lacks the kinase domain of the full-length phytochrome, and/or comprises the tandem C-terminal PAS domains.

The invention also includes kits comprising a first and a second protein construct, and/or one or more nucleic acids encoding said first and second protein constructs, and/or recombinant cells comprising such nucleic acids or protein constructs, wherein the first protein construct comprises a first protein sequence of interest and a PIP, and the second protein construct comprises a second protein sequence of interest and a PHD. The PIP for example comprises the activated phytochrome B-binding domain (APB) of PIF6. The PHD is for example the phytochrome domain from PhyB of *A. thaliana* or a fragment or variant thereof. The PHD can for example convert in a fully photo-reversible manner from a red-light absorbing conformer (Pr state) to a far-red light-absorbing conformer (Pfr state) upon exposure to red light, and/or can convert in a fully photo-reversible manner from the Pfr state to the Pr state upon exposure to infra-red light. The PHD optionally lacks the kinase domain of the full-length phytochrome, and/or comprises the tandem C-terminal PAS domains. The kit can further comprise a chromophore such as those described herein.

BRIEF DESCRIPTION OF THE DRAWINGS

FIG. 1: Exemplary sequence of a phytochrome PhyB from *Arabidopsis thaliana* (SEQ ID NO:2).

FIG. 3: Phytochrome-PIF association and disassociation. A) Schematic of Phytochrome-PIF association and disassociation. B) Schematic of association test in vivo by membrane recruitment C) Actual association in mammalian cells as seen by cytoplasmic depletion and membrane recruitment.

FIG. 4: Observation of oscillatory association and disassociation of membrane localized PhyB908 and PIF6APB tagged YFP, a first demonstration of full temporal control of association and dissociation.

FIG. 5: A) Schematic of strategy used to induce localized association and membrane recruitment B) Demonstration of dynamic localized membrane association of PIF6APB tagged YFP.

FIG. 6: Demonstration of activation of lamellipodial signalling cascade by membrane recruitment of signalling factor TiamDHPH in Red light but not infrared IR light.

FIG. 7: A) Schematic of localized induction of association of Phytochrome-PIF pair to recruit signalling molecules. B) Demonstration of localized induction of lamellipodia by recruitment of Tiam DHPH domain to plasma membrane.

FIG. 13. Validation of systems in yeast. Graph showing timecourse of cells containing mCherry-labelled phytochrome recruiter on plasma membrane and the cytoplasmic PIF6-tagged YFP oscillating in concentration in the imaged slice in response to varying red and infrared light exposure.

DETAILED DESCRIPTION OF THE INVENTION

I. Definitions

Figure 2:
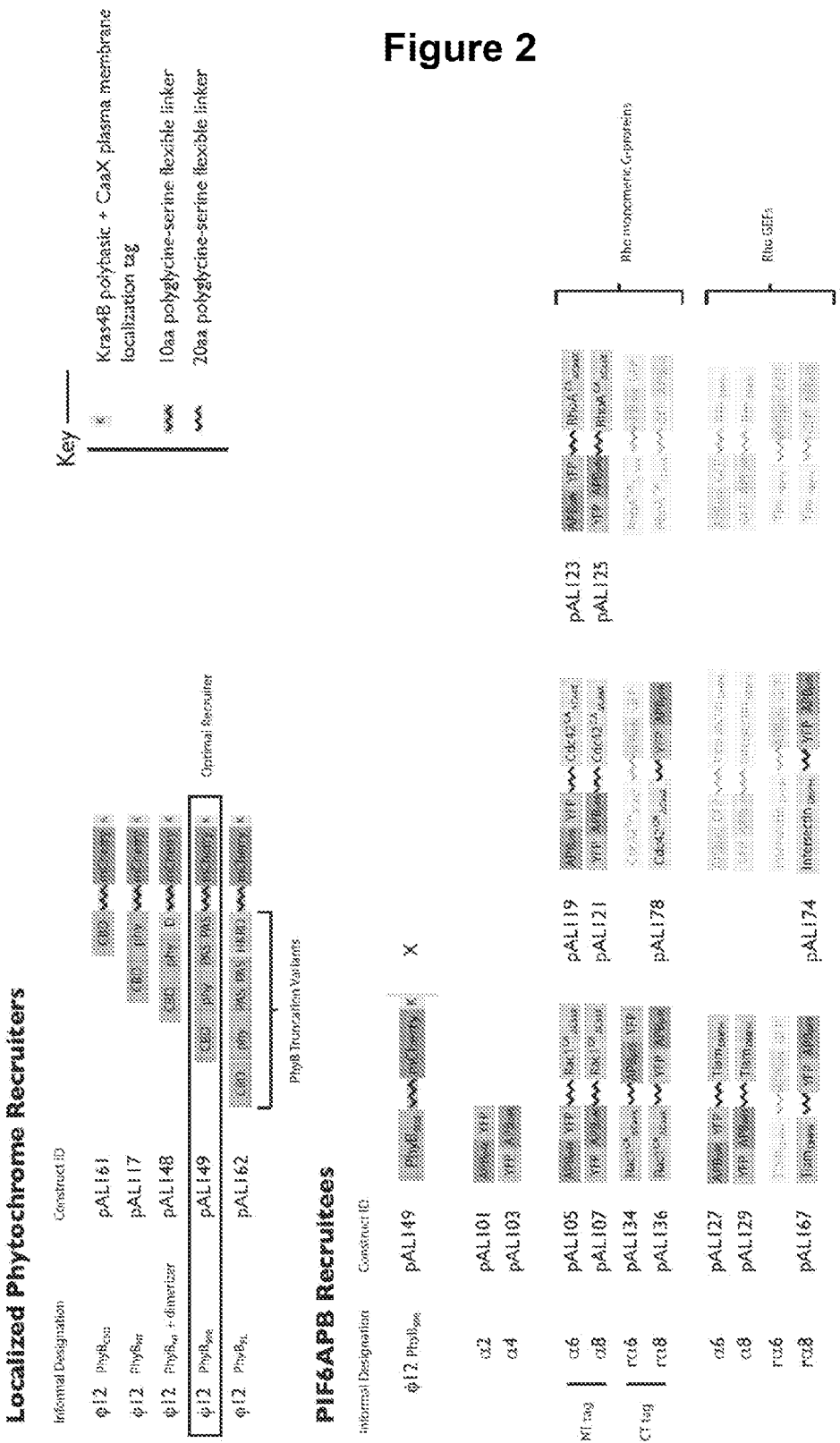
FIG. 2: Atlas of protein construct topologies and specific examples of protein constructs useful for light-regulated association.

The terms "protein" and "protein sequence" are used interchangeably herein to refer to a polymer of amino acid residues. As used herein, these terms can encompass a naturally-occurring protein sequence such as the full-length natural protein or a portion thereof. Also included are proteins with sequence variations that do not interfer the biological activity (e.g., binding specificity) of the protein. Proteins can be produced by a variety of methods, e.g., recombinant technology and/or solid phase synthesis.

A "protein construct" as used herein indicates an artificially made or recombinant molecule that comprises two or more protein sequences that are not naturally found within the same protein. In general, at least one of the two or more protein sequences in a protein construct used in the methods of the invention is a PIP or PHD, as described below3333. In some embodiments, a protein construct can have non-proteinaceous elements as well as proteinaceous elements. For example, in a protein construct comprising a PHD, the PHD can comprise not only a polypeptide but also usually comprises a choromophore.

Protein constructs that comprise more than one protein can be made by any known method. The protein construct can for example be a fusion protein, or can be synthesized by solid phase synthesis methods, or made by conjugation or linkage of existing proteins, e.g., by chemical linkage. If desired, the individual proteins can be attached to each other by linker peptide sequences. Examples of linker sequences include standard polyglycine-serine flexible linkers, which can be made by, e.g., oligo annealing. Examples include a 10aa-linker: DSAGSAGSAG [gat agt gct ggt agt gct ggt agt gct ggt] and a 20aa-linker: SAGGSAGGSAGGSAGGSAGG [agt gct ggt ggt agt gct ggt ggt agt gct ggt ggt agt gct ggt ggt] (SEQ ID NOS:11, 10, 13 and 12).

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds.

A recombinant sequence (e.g., a nucleic acid or protein sequence) herein indicates a sequence that is not naturally occurring or is made by an artificial combination of two otherwise separated segments of sequence. A recombinant sequence can be made by chemical synthesis or by the artificial manipulation of existing sequences, e.g., by genetic engineering techniques. Once introduced into a host cell, a recombinant nucleic acid is replicated by the host cell, however, the recombinant nucleic acid once replicated in the cell remains a recombinant nucleic acid for purposes of this invention. Similarly, the term "recombinant" or "recombinantly expressed" when used with reference to a cell indicates that the cell contains or replicates or expresses a nucleic acid sequence, or contains or expresses a peptide or protein sequence, whose origin is exogenous to the cell. Recombinant cells can also contain or express nucleic acid/protein sequences found in the native form of the cell wherein the nucleic acid/protein sequences are re-introduced into the cell by artificial means, for example under the control of a heterologous promoter.

II. Assays Based on Regulation of Association

The present invention includes a genetically-encoded, light-switchable assay system for modulating protein-protein interactions. The system is based upon a properly-titrated, tight but photo-reversible binding between a phytochrome domain (PHD) with a phytochrome-interacting protein (PIP), for example a phytochrome-interacting factor (PIF). The system allows spatiotemporal control of interaction at a fine resolution. Binding between the PHD and the PIP is strong enough to result in a significant and detectable interaction within the cell, yet is reversible and shows fast association and dissociation rates. As is described herein, the system can control protein interactions within a spatial resolution in the range of a micrometer and within a timescale in the range of a second.

This system can be applied to control processes in living cells, such as a process that is dependent on a recruitment event. Unlike classical uncaging techniques, photoreversibility allows our system to defeat diffusive spreading through exposure to light. Further, the direct relationship between the recruited fluorescent fraction and signalling activity also allows measurable 'dosage' of signalling flux for quantitative perturbations. The examples herein demonstrate that the system works robustly in mammalian cells.

Among other things, the invention provides methods, materials and systems of regulating association between proteins of interest using light. In an aspect, the invention takes advantage of the ability of phytochromes to change conformation upon exposure to appropriate light conditions, and to bind in a conformation-dependent manner to cognate proteins called phytochrome-interacting factors. Phytochromes can efficiently and reversibly photointerconvert between red light absorbing Pr and far red light absorbing Pfr forms, a property conferred by covalent association of a linear tetrapyrrole (bilin or phytobilin) with a large apoprotein.

In an aspect, the invention comprises a method of regulating interaction between a first protein of interest and second protein within a cell by light. Such a method may include (1) providing in the cell a first protein construct which comprises the first protein and a phytochrome domain (PHD), and (2) providing in the cell a second protein construct which comprises the second protein and a phytochrome domain-interacting peptide (PIP) that can bind selectively to the Pfr state, but not to the Pr state, of the phytochrome domain. In one strategy, the first and/or second protein construct is a fusion protein. In one aspect, the phytochrome domain can reversibly convert from the red-light absorbing conformer (Pr state) to a far-red light-absorbing conformer (Pfr state) upon exposure to red light, and can reversibly convert from the Pfr state to the Pr state upon exposure to infra-red light. In such embodiments, interaction between the first protein construct and the second protein construct can be regulated by regulating cell exposure to red light and/or infra-red light. In other words, association between the first and second protein of interest can be controlled by controlling through light exposure the association between the PHD of one protein construct and the PIP of the other protein construct, according to the methods taught herein.

In one aspect, the first and/or the second protein sequences of interest are not endogenously present in the cell, or are present at low levels that do not interfere with the purposes of the assay.

In one aspect, the first and second protein sequences of interest do not normally associate or interact with each other. In cases where the first and second protein can interact with each other in their naturally-occurring forms, either or both can be modified if desired in such a manner that they do not associate or interact with each other in the absence of association between the PHD and the PIP.

In an example, a PHD (e.g., PhyB 1-908, i.e., a PHD comprising PhyB (SEQ ID NO:2) sequence from amino acid residue 1 to 908) is fused to a first protein sequence of interest in a first protein construct and a PIP (e.g., the activated phytochrome B-binding domain (APB) of SEQ ID NO:7 (i.e., PIF6)) is fused to a second protein sequence of interest to form a second protein construct. A protein sequence of interest need not correspond to a full-length protein found in nature, but can be derived from any portion thereof and can contain variations that do not eliminate binding activity.

In certain embodiments the invention includes the use of polypeptides with at least about 60%, 70%, 80%, 90%, 95% or at least 99% identity (at the nucleotide level) with a known polypeptide of interest (such as a PHD or PIP described herein). As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison, and multiplying the result by 100 to yield the percentage of sequence identity.

Optionally the first and second protein sequences of interest do not interact with each other. For example, the first and second protein sequences of interest can be derived from non-interacting portions of one or more proteins. Optionally, the first and second protein constructs only interact with each other through the PHD and PIP domains. Alternatively, the first and second protein sequences are capable of interacting with each other independently of any interaction between the PHD and PIP. Association between the PHD and PIP can serve to enhance or modify or impair the interaction between the first and second protein sequences. For example, association of the PHD and PIP serves to localize interaction between the first and second protein sequences to a specific subcompartment within the cell.

Association of the PHD and the PIP, and the resulting association between the first protein and/or the second proteins of interest, can result in a biologically significant effect upon the cell. In one embodiment, the first and second proteins interact when associated via the PHD and the PIP, and the interaction produces an effect on a cell structure or process. For example, the first protein can cause the second protein to be modified when both are brought into proximity by the association between the PHD and PIP, or visa versa. In one such situation, the first protein is a kinase and the second protein is a substrate for the kinase, or visa versa. In another embodiment, the first and/or second protein can associate or interact with a third protein only when the first and second proteins are brought together through an association between the PHD and the PIP. In yet another example, the first protein can dissociate from a third protein (e.g., an inhibitory protein) only when brought together with the second protein through an association between the PHD and the PIP, or visa versa.

In another aspect, dissociation (rather than association) between the first and second protein of interest results in a biologically significant effect upon the cell. In one such example, association between the PHD and PIP portions acts to prevent a different association or interaction between the first and second proteins. In another such example, the first and/or second protein can only associate with or interact with a third protein when separated from each other due to dissociation between the PHD and the PIP. In another example, the first and/or second protein can dissociate from a third protein (e.g., an inhibitory protein) only when separated from each other due to dissociation between the PHD and the PIP.

The association between the proteins of interest can modulate or have an effect on any biologically significant cellular process. In an aspect, the association (or dissociation) between the proteins or protein constructs of interest can have an effect on a cellular signaling process (e.g., the first and/or second proteins of interest are signaling proteins).

III. Phytochrome Domains (PHD)

A. Conversion Between the Pfr State and the Pr State

In an aspect, a phytochrome domain (PHD) of the invention comprises a protein sequence derived from a phytochrome protein. In one aspect, a phytochrome domain (PHD) of the invention is capable of light-regulated, reversible interconversion between two conformational states: a biologically inactive Pr state which absorbs red (R) photons more efficiently, and a biologically active Pfr state which absorbs FR (far-red, also called infra-red herein) photons more efficiently.

In one aspect, the PHD can convert between a Pfr state and a Pr state in response to the presence, absence, spectral quality, fluence rate, and/or directionality of light to which the cell or organism is exposed. When associated with an appropriate chromophore the phytochrome protein sequence can convert between the Pfr state and Pr state.

The PHD preferably binds reversibly to the PIP, although PHDs that undergo irreversible binding can also be used in some situations. In one aspect, the PHD can comprise minimal portions of a phytochrome protein competent to undergo reversible conversion. For example, residues 1-650 of a Phy protein, e.g., PhyB (SEQ ID NO:2), can bind reversibly to PIF3 (SEQ ID NO:6). In certain situations a strong affinity interaction between the PHD and PIF may be desired, e.g., a strong interaction that results in a significant and visually detectable interaction inside mammalian cells. In certain embodiments the PHD and PIP pair of interest results in strong binding within a system of interest (e.g., within cells such as mammalian cells). One non-limiting example of a PHD-PIP pair showing strong affinity that generates a visually detectable interaction in mammalian cells is PhyB+PIF6. For example, a first protein construct comprising Phy B (1-450) or PhyB(1-650) can show strong interaction with a second protein construct comprising the APB of PIF6, that can be visually detected in mammalian cells using the methods taught herein. However, this binding is irreversible in mammalian cells.

Where reversibility is desired, then the protein construct comprising the PHD can optionally comprise an autoinhibitory sequence that allows the PHD to retain reversibility (e.g., full reversibility) of binding with the PIP. In an embodiment, the autoinhibitory sequence comprises one or more PAS domains from a phytochrome. PAS domains have been identified in a variety of phytochromes by homology. Ponting, C. P., and Aravind, L. (1997), Curr. Biol. 7, R674-R677. This domain is well conserved and easily identifiable by sequence homology within diverse phytochromes. Montgomery et al., Trends Plant Sci. 7, 357-366. For example, the PAS domains can be identified by sequence identity of at least 70%, 80% or 90% with the PAS domains of *A. thaliana* PhyB (SEQ ID NO: 2). For example, residues 650 to 908 of a Phy protein from *Arabidopsis*, e.g., PhyB (Genbank ID. 816394; SEQ ID NO:2) can confer reversibility of binding between PhyB and PIF6-APB.

The minimal sequence needed for reversible binding for a given PHD can be determined using the methods described herein. For example, a first protein construct comprising a test fragment of a PHD, and a second protein construct comprising a cognate PIP, can be introduced into a cell and exposed successively to red (to promote binding) and then to infra-red light (to promote dissociation). The observation of association between the PHD and PIP, followed by dissociation, indicates that binding is reversible. Association and dissociation can be visualized using methods described herein, e.g., by adding appropriate labels or proteins to the first and/or second construct. For example, one construct can contain a membrane localization sequence, while the other construct can contain a detectable tag, e.g., green fluorescent protein (GFP), wherein binding can be detected by localization of the GFP to the membrane. In another example, established techniques can be used to determine association (and its reversibility) between a PHD and a PIP, including bimolecular fluorescence complementation (BiFC), fluorescence resonance energy transfer (FRET), chemical crosslinking, dual polarisation interferometry (DPI), static light scattering (SLS), or a yeast two-hybrid assay.

B. Phytochrome Protein Portion of the Phytochrome Domain

The phytochrome domain (PHD) can comprise any portion of a phytochrome protein, or any variant, or derivative of such a portion, that retains the ability to convert (optionally reversibly) between a Pfr state and a Pr state upon exposure to light of specific wavelengths.

A typical phytochrome protein is a soluble dimer of two polypeptides of about 125 kD, each of which folds into two major structural domains: an N-terminal domain that is associated with a single, covalently attached tetrapyrrole chromophore, phytochromobilin; and a C-terminal domain that mediates dimerization. Phytochrome proteins from which PHDs of the invention can be derived include phyA-phyE from *Arabidopsis*. Other phytochrome proteins include PhyA from oat (Avena sativa); PhyA, PhyB1, PhyB2 from black cottonwood (Populus spp.); PhyA, PhyB, PhyE from Medicago trunculatus; and PhyA, PhyB, PhyC from rice (oryza sativa). Preferred phytochromes are PhyA (Genbank ID. 837483, SEQ ID NO:1), PhyB (Genbank ID. 816394, SEQ ID NO:2), PhyC (Genbank ID. 833570, SEQ ID NO:3), PhyD (Genbank ID. 827319, SEQ ID NO:4), PhyE (Genbank ID. 827538, SEQ ID NO:5). Plant phytochromes (Phy family) are members of a more widespread family of photosensors that are found in cyanobacteria (cyanobacterial phytochromes Cph1 and Cph2) as well as in purple and nonphotosynthetic bacteria (bacteriophytochromes; BphP) and even fungi (fungal phytochromes; Fph family) (Montgomery and Lagarias, 2002; Blumenstein et al., 2005; Froehlich et al., 2005; Karniol et al., 2005). Given the fundamental photosensory role of phytochromes, their sequence and structure is well conserved across organisms. Rockwell et al., The Plant Cell 18:4-14 (2006).

An exemplary phytochrome sequence (*A. thaliana* PhyB) is shown in FIG. 1 and SEQ ID NO:2.

In one aspect, the PHD comprises an N-terminal domain from a phytochrome protein, where the domain retains the ability to associate with a tetrapyrrole chromophore such as phytochromobilin. For example, the PHD can comprise a bilin lyase domain (BLD) which allows attachment of the chromophore to the apoprotein. The BLD can optionally be less than 200 amino acids long. The first 70 amino acids of the PHD are not required for chromophore binding. The BLD can for example comprise residues 70-150 of a phytochrome such as PhyB (GenBank ID 816394, SEQ ID NO:2), e.g., residues 70-150, 70-160, 70-180 or 70-190.

The PHD domain is optionally from PhyB, such as PhyB from *A. thaliana*. Optionally, the PHD domain is not a full-length phytochrome. Optionally, the PHD domain lacks the C-terminal kinase domain of the phytochrome. The PHD for example does not cause degradation of an associated PIP.

The PHD domain can comprise the chromophore binding domain of PhyB (e.g., residues 1-450 or residues 1-650 of SEQ ID NO:2). Where reversible binding is desired, the PHD can comprise a chromophore binding domain and an autoinhibitory sequence that can confer photo-reversibility. Such an autoinhibitory sequence can for example include the tandem C-terminal PAS domains. The autoinhibitory sequence can for example comprise PhyB sequence spanning from residues 750-850 of GenBank ID 816394, for a fragment spanning PhyB sequence lying between a first residue and a second residue, where the first residue is 650, 670, 690, 700, 710 or 720 and the second residue is 850, 870, 890, 900, 907, 910, 917, 930, 940 or 950. Examples of PhyB fragments that can confer photoreversibility include PhyB(650-908) and PhyB (700-950).

In examples, useful PhyB fragment can comprise *A. thaliana* PhyB sequence spanning from a first residue to a second residue. The first residue is for example residue 1, 5, 10, 15, 30, 50, 70, 73 or 75 of PhyB (SEQ ID NO:2). The second residue is optionally any residue between 850 and 950, including residue 855, 860, 865, 870, 875, 880, 881, 882, 883, 884, 885, 886, 887, 888, 889, 890, 891, 892, 893, 894, 895, 896, 897, 898, 899, 900, 901, 902, 902, 904, 905, 906, 907, 908, 909, 910, 911, 912, 913, 914, 915, 916 or 917 of PhyB from *A. thaliana* (SEQ ID NO:2).

Useful PHDs of the invention can include:
1) PhyB chromophore binding domain, residues 1-450: binds PIF6-APB constitutively, not reversible
2) PhyB N terminus, residues 1-650: binds PIF6-APB constitutively, not reversible
3) PhyB908, residues 1-908: binds PIF6-APB reversibly
4) PhyB917, residues 1-917: binds PIF6-APB reversibly, minor variant used in synthetic, re-encoded versions of the constructs
5) PhyB full length, residues 1-1172: binds PIF6-APB reversibly, but contains a C-terminal kinase domain that is unnecessary Optionally, the phytochrome domain does not translocate into the nucleus in the Pfr state. In an embodiment, the PHD lack any domains that are responsible for regulation of gene expression.

C. Chromophores

In an aspect, the PHD polypeptide is associated with a chromophore, such as phytobilin, that is associated with the phytochrome protein sequence of the PHD. Phytobilins are linear tetrapyrrole molecules synthesized by plants, algae, and cyanobacteria that function as the direct precursors of the PHD chromophores. Absorption of red light triggers a "Z" to "E" isomerization in the C-15 double bond between the C and D rings of the linear tetrapyrrole, resulting in the far-red light-absorbing form Pfr.

Other chromophores that can used in the invention include blue shifted tetrapyrroles like phycoviolobilin PVB, or synthetic tetrapyrrole derivatives of natural phytobilins that retain their ability to attach to phytochromes with possibly altered absorbance spectra. Chromophores can be obtained by purification from natural sources (e.g., *A. thaliana* cells, spirulina cells, and the like).

The chromophore can be introduced into a cell of interest by exogenous administration into the extracellular environment (e.g., the culture medium), such that the outer surface of the cell is placed in contact with the chromophore, and allowing the cell to internalize the chromophore. A cell of interest can optionally be engineered or modified to contain genes for enzymes that will generate PCB from heme or biliverdin.

IV. Phytochrome Domain-Interacting Peptides

A phytochrome domain-interacting peptide (PIP) of the invention can comprise any protein sequence that can bind selectively to one conformeric state of a PHD, but not the other. The PIP can for example bind to the Pfr state but not to the Pr state.

The PIP can comprise an APA (activated phyA-binding) or APB (activated PhyB-binding) domains from phytochrome-interacting factors (PIF), or any portion, variant or derivative thereof. Known PIFS include PIF1 to PIF6 from *Arabidopsis Thaliana*. Especially useful PIFs include PIF3 (Genbank ID. 837479, e.g., SEQ ID NO:6), PIF6 (Genbank ID. 825382, e.g., SEQ ID NO:7), PIF4 (Genbank ID. 818903, e.g., SEQ ID NO:8), and PIL1 (Genbank ID. 819311, e.g., SEQ ID NO:9). PIF6 (SEQ ID NO:2) has the strongest binding PIP and is particularly useful for the invention. The APB domain typically resides in residues 1-100 of the PIFs described herein. The APA motif can reside in residues 100-210 as is the case with PIF3. The minimal sequence required for selective binding of a PIP can be determined using methods taught herein.

In another example, the PIP can comprise an antigen-binding site of an antibody that binds selectively to one conformeric state, e.g., the Pfr state, of a PHD.

V. PHD-PIP Pairs

The invention uses PHD and PIP pair that can associate together, which association can be regulated and/or monitored using the methods taught by the invention.

Any reference to a PHD or PIP protein is intended to include not only the full-length protein but functional fragments thereof. The fragment is optionally capable of binding robustly and reversibly to its corresponding binding partner, for example under intracellular conditions, such as within a mammalian cell.

Suitable PHDs or PIPs are not limited to full-length proteins or fragments encoded by naturally occurring genes. For example, techniques of directed evolution can be used to produce new or hybrid gene products with methyl transferase activity. In addition, catalytically active fragments and variants of naturally occurring PHDs or PIPs can be used. Partially or wholly synthetic PHDs or PIPs, such as enzymes designed in silico or produced by using art-known techniques for directed evolution including gene shuffling, family shuffling, staggered extension process (StEP), random chimeragenesis on transient templates (RACHITT), iterative truncation for the creation of hybrid enzymes (ITCHY), recombined extension on truncated templates (RETT), and the like (see Crameri et al., 1998, "DNA shuffling of a family of genes from diverse species accelerates directed evolution" Nature 391:288-91; Rubin-Pitel et al., 2006, "Recent advances in biocatalysis by directed enzyme evolution" Comb Chem High Throughput Screen 9:247-57; Johannes and Zhao, 2006, "Directed evolution of enzymes and biosynthetic pathways" Curr Opin Microbiol. 9:261-7; Bornscheuer and Pohl, 2001, "Improved biocatalysts by directed evolution and rational protein design" Curr Opin Chem Biol. 5:137-43).

PHD-PIP pairs of interest can be identified using methods taught herein. For example, a first protein construct comprising a test PHD, and a second protein construct comprising a test PIP, can be introduced into a cell and exposed to red light to promote binding. The test PHDs and PIPs can be fragments or variants of known proteins, e.g., those described herein. The observation of association between the test PHD and the test PIP indicates that binding has occurred.

Finally, the reversibility of binding can be determined using the teachings herein. Binding between a PHD and PIP contruct is reversible if the PHD construct and the PIP construct are observed to dissociate upon exposure to infrared light.

Association can be visualized using methods described herein, e.g., by adding appropriate labels or proteins to the first and/or second construct. For example, one protein construct can contain a membrane localization sequence, while the other protein construct can contain a detectable tag, e.g., GFP, wherein binding can be detected by localization of the GFP to the membrane. In another example, established techniques can be used to determine association (and its reversibility) between a PHD and a PIP, including bimolecular fluorescence complementation (BiFC), fluorescence resonance energy transfer (FRET), chemical crosslinking, dual polarisation interferometry (DPI), static light scattering (SLS), or a yeast two-hybrid assay, affinity electrophoresis, label transfer, immunoelectrophoresis, in-vivo crosslinking of protein complexes using photo-reactive analogs, and others. For example, the $K_D$ and binding affinity can be measured by known techniques such as fluorescence correlation spectroscopy.

In an embodiment, the PHD is for example PhyB of *A. thaliana*. The PIP is for example a phytochrome-interacting factor such as PIF6. One such PhyB/PIF6 pair is PhyB908 (a peptide comprising at least the first 908 residues of PhyB), in conjunction with a peptide comprising at least the first 100 residues of PIF6 (PIF6-APB). Other examples of PHD-PIP pairs include PhyB and a peptide comprising the first 100 residues of PIF3 (PIF3-APB); PhyA and the APA motif of PIF3; PhyA and the C terminus of Hfy1 from *Arabidopsis*. The PHD and the PIP optionally associate in a manner that can be regulated by exposure to light. This association is for example reversible, such that the association pair can be dissociated by altering the exposure of the cell to light. In one example, the PHD and the PIP can be made to associate by exposure to red light (resulting in conversion to the Pfr state). When desired, this association is reversed by exposure to infra-red light (and/or very long exposures to darkness, and/or removal of exposure to red light). Alternatively, the association can be irreversible.

VI. Subcellular Localization Signals

In one aspect, the invention can include a first protein construct that comprises (1) a protein of interest, (2) a PHD and (3) a subcellular localization signal (SLS). The SLS can localize the first protein construct to any subcellular compartment of interest. In such an embodiment, a second protein of interest can optionally be attached to a corresponding PIP (to form a second protein construct). The localization of the second protein construct can then be regulated by exposure to light. For example, where the PIP binds to the Pfr state, the cell can be exposed to red light, thereby converting the PHD to the Pfr state, and recruiting the second protein construct comprising the PIP to the same subcellular compartment as the first protein construct. In an alternative strategy, the first protein construct comprises (1) a protein of interest, (2) a PIP and (3) a subcellular localization signal (SLS), while the second protein construct comprises a second protein of interest and a PHD.

Various SLSs are know that can direct proteins to subcellular compartments such as the extracellular space, cytoplasm, nucleus, mitochondria, Golgi apparatus, endoplasmic reticulum (ER), peroxisome, vacuoles, plastids, cytoskeleton, nucleoplasm, nucleolus, nuclear matrix, actin and tubulin filaments, endosomes or ribosomes. The SLS can be attached in the appropriate orientation, N or C terminal to the protein construct. In one aspect, the first and/or second protein construct does not comprise a nuclear localization signal. For example, the first and/or second protein construct can comprise an SLS that localizes to a non-nuclear subcompartment of the cell.

Specific examples of SLSs include:
1) Hras [Entrez Gene ID: 3265] palmitoylation CaaX sequence (GCMSCKCVLS), ggc tgc atg agc tgc aag tgt gtg ctc tcc, (SEQ ID NOS:14 and 15) targets to the plasma membrane, endoplasmic reticulum membrane, and golgi membrane.
2) Kras4B [Entrez Gene ID: 3845] polybasic CaaX terminus (SKTKCVIM) [ggt aaa aag aag aaa aag aag tca aag aca aag tgt gta att atg](SEQ ID NOS:16 and 17), targets to the plasma membrane.
3) Lyn kinase [Entrez Gene ID: 4067] NT13 plasma membrane targeting sequence MGCIKSKGKDSAGA [atg gga tgt ata aaa tca aaa ggg aaa gac agc gcg gga gca] (SEQ ID NOS:18and 19)
4) α-actinin [Entrez Gene ID: 87] F-actin binding domain (ABD) (residues 33-245) was cloned from a vector bearing a partial region of the cDNA. This targets the actin cytoskeleton.
5) human β, 4-galactosyltransferase: the n-terminal 81 amino acids targets a protein to the trans-medial region of the Golgi apparatus.
6) mitochondrial targeting sequence from the precursor of subunit VIII of human cytochrome C oxidase. (Rizzuto, Brini et al. 1995).
7) endoplasmic reticulum targeting sequence of calreticulin (Fliegel, Burns et al. 1989).

Other known SLSs can be found in public databases such as eSLDB (eukaryotic cells, http://gper.biocomp.unibo.it/esldb/) and pSORTb (bacterial signals, available at http://www.psort.org).

VII. Detectable Labels

In one aspect, one or more proteins (or protein constructs) of the invention is attached to a detectable label. A wide variety of detectable labels are known in the art. Such labels include molecules that can be attached to or form part of a protein or protein construct of the invention and is capable of being detected (or is capable of reacting to form a chemical or physical entity (e.g., a reaction product) that is detectable) in an assay according to the instant disclosure. Representative examples of detectable labels or reaction products include precipitates, fluorescent signals, compounds having a color, and the like. Representative labels include, e.g., fluorophores (e.g., below), bioluminescent and/or chemiluminescent compounds, radioisotopes (e.g., 131I, 125I, 14C, 3H, 35S, 32P and the like), enzymes (e.g., below), binding proteins (e.g., biotin, avidin, streptavidin and the like), magnetic particles, chemically reactive compounds (e.g., colored stains), labeled-oligonucleotides; molecular probes (e.g., CY3, Research Organics, Inc.), and the like.

Representative fluorophores include fluorescein isothiocyanate, succinyl fluorescein, rhodamine B, lissamine, 9,10-diphenlyanthracene, perylene, rubrene, pyrene and fluorescent derivatives thereof such as isocyanate, isothiocyanate, acid chloride or sulfonyl chloride, umbelliferone, rare earth chelates of lanthanides such as Europium (Eu) and the like. Representative labels that can be conjugated to include the enzymes in: IUB Class 1, especially 1.1.1 and 1.6 (e.g., alcohol dehydrogenase, glycerol dehydrogenase, lactate dehydrogenase, malate dehydrogenase, glucose-6-phosphate dehydrogenase, glyceraldehyde-3-phosphate dehydrogenase and the like); IUB Class 1.11.1 (e.g., catalase, peroxidase, amino acid oxidase, galactose oxidase, glucose oxidase, ascorbate oxidase, diaphorase, urease and the like); IUB Class 2, especially 2.7 and 2.7.1 (e.g., hexokinase and the like); IUB Class 3, especially 3.2.1 and 3.1.3 (e.g., alpha amylase, cellulase, β-galacturonidase, amyloglucosidase, β-glucuronidase, alkaline phosphatase, acid phosphatase and the like); IUB Class 4 (e.g., lyases); IUB Class 5 especially 5.3 and 5.4 (e.g., phosphoglucose isomerase, trios phosphatase isomerase, phosphoglucose mutase and the like.)

Useful labels also include labels whose products are detectable by fluorescent and chemiluminescent wavelengths, e.g., fluorescence emitting metals such as 152Eu, or others of the lanthanide series; compounds such as luminol, isoluminol, acridinium salts, and the like. Fluorescent or bioluminescent proteins can be especially useful, such as luciferase, luciferin; fluorescent proteins; and the like. Fluorescent proteins include, but are not limited to the following: namely, (i) green fluorescent protein (GFP), i.e., including, but not limited to, a "humanized" versions of GFP wherein codons of the naturally-occurring nucleotide sequence are exchanged to more closely match human codon bias; (ii) GFP derived from Aequoria victoria and derivatives thereof, e.g., a "humanized" derivative such as Enhanced GFP, which are available commercially, e.g., from Clontech, Inc.; (iii) GFP from other species such as *Renilla reniformis, Renilla mulleri*, or *Ptilosarcus guernyi*, as described in, e.g., WO 99/49019 and Peelle et al. (2001) J. Protein Chem. 20:507-519; (iv) "humanized" recombinant GFP (hrGFP) (Stratagene); and, (v) other fluorescent and colored proteins from Anthozoan species, such as those described in Matz et al. (1999) Nature Biotechnol. 17:969-973; and the like. Also included are fluorescent proteins of other colors, e.g., mCherry, mStrawberry, mTangerine, mTomato, mOrange, mBanana and mHoneydew, EGFP, ECFP and EBFP. Yellow fluoresecent protein include the Citrine and Venus versions. Other examples of fluorescent proteins are listed in Shaner et al., Nature Methods, 2(12): 905-917 (2005), incorporated by reference in its entirety.

Where desired, the label reflects or emits a detectable light signal under appropriate conditions that allows the labeled protein to be detected. The label can for example be visually detected by itself instead of having its presence inferred through detection of another labeled product. Examples of appropriate conditions include exposure to light of excitatory wavelength in the case of a fluorescent label or exposure to visible light in the case of a colored label. The visually detectable label can for example emit light within the optically visible range of the spectrum. Optionally, the label emits light that can be detected by the human eye, with or without the aid of other instrumentation such as the microscope.

The labels are optionally detectable using a non-invasive method. One method is visual examination by eye, optionally with the aid of devices such as a microscope. Other methods include methods amenable to automation such as a spectrophotometric method, a fluorescence method, a chemiluminescent method, a electrical nanometric method involving e.g., a change in conductance, impedance, resistance and the like and a magnetic field method.

If desired, the labels can be attached to the protein or protein construct by any known method. The label can be attached for example by using a chemical linking method as discussed herein or if proteinaceous in nature, by generation of a fusion protein. Attaching certain labels to proteins can also be accomplished through metal chelating groups such as EDTA, linkers, etc.

VIII. Strength of Association

The interaction between the PHD and the PIP optionally allows fine spatiotemporal control in vivo. For example, binding between the PHD and PIP should be strong enough to result in a detectable and significant recruitment under intracellular conditions (e.g., within mammalian cells).

For example, the affinity of binding between the PHD and PIP can be expressed in terms of a dissociation constants $K_D$. Optionally the $K_D$ is at least about 500 nM, for example at least about 250 nM. Where fine spatiotemporal control (discussed below) is desired, especially useful binding partners can have an affinity of binding in the range of 10-250 nM. For example, the association constant for binding between the PIP and the Pfr state of the PHD can be less than about 500 nM; for example less than about 250 nM. In especially useful combinations of PIPs and PHDs, the association constant is less than about 100 nM.

The PHD and PIP can specifically bind to each other. For example, the PHD and PIP can preferentially bind to each other when present within a mixture of different proteins (for example the entire repertoire of proteins present within a cell). In some methods, the PHD and PIP can specifically bind to each other instead of other proteins with a greater than about 10- to about 100-fold; sometimes greater than about 1000- to about 10,000-fold increased affinity. In other cases, the PHD and PIP show detectable levels of binding to each other in the presence of a repertoire of proteins present within a living cell, wherein neither protein shows detectable levels of binding to other proteins.

In another aspect, the PIP can specifically bind to the Pfr state of the PHD. For example, the PIP can preferentially bind to the Pfr state and not the Pr state. In some methods, the PIP can specifically bind to the Pfr state with an affinity that is greater than about 10- to about 100-fold; sometimes greater than about 1000- to about 10,000-fold, than its affinity for the Pr state.

In some embodiments interaction between the PIP and PHD can result in a visually detectable change in spatial and/or temporal distribution of one or more protein constructs within a cell. For example, a first protein construct comprising a PHD can comprise a subcellular localization signal that recruits it to a specific subcellular compartment, while a second protein construct containing a PIP can optionally be engineered to emit a visually detectable signal, or vice versa Exposure to red light stimulates PIP-PHD interaction which can further result in the translocation of the detectable signal to the specific subcellular compartment. Optionally, the binding between the PHD in the Pfr state and the PIP is robust enough (i.e., of high enough affinity) to result in sufficient translocation within mammalian cells to produce a change in distribution that is optically visible to the human eye, (e.g., detectable photographically or microscopically, for example with the aid of confocal microscopy). For example, the detectable signal that is emitted from a subcellular compartment after recruitment can be at least about 1.5×, 2×, 3×, 5× or 10× higher than before recruitment. See, e.g., FIG. 9b.

The affinity of the PIP for the Pfr state of the PHD is optionally preferential enough to result in at least a 10×, 20×, 50×, 100× or 500× increase of PIP-PHD complex upon exposure to red light relative to the amount of bound complex upon exposure to infra-red light.

The interaction between the PIP and the PHD optionally exhibits very quick rates of association or dissociation. The "on rate" or rate of dissociation upon exposure to red light can be for example within the range of 0.3-60 s. For example, above 50% of fully-dissociated PHD and PIP can bind together within 1, 5, 10, 30 or 60 seconds of exposure to intense red light (for example a 100-millisecond pulse of red light of about 10,000 micromoles of photons per square meter). Optionally, at least 90% of dissociated PHD and PIP can bind together within 1 second after such a pulse.

The "off rate" or rate of dissociation upon exposure to infrared light is optionally 0.3-60 s. For example, above 50% of fully-associated PHD and PIP can dissociate within 1, 5, 10, 30 or 60 seconds of exposure to intense infrared light (for example a 100-millisecond pulse of infrared light of about 10,000 micromoles of photons per square meter). Optionally, at least 90% of associated PHD and PIP can dissociate within 1 second after such a pulse.

Where PIP-PHD binding results in subcellular localization (e.g., membrane recruitment), it can yield time constants of 1-5 seconds for recruitment to the subcellular compartment and time constants of 1-10 seconds for release from the subcellular compartment, demonstrating second-timescale control.

IX. Reversibility of Association

The PHD and PIP binding partners can be made to associate with each other (wherein the binding partners in the associated state are referred to as the "interaction complex"). Association (or dissociation) can be achieved for example by placing the binding partners in contact with each other (e.g., within the same cell or cellular compartment) and subjecting them to associating (or dissociating) conditions.

Optionally, this association is reversible in that the binding partners within the interaction complex can be made to dissociate by subsequently subjecting the binding partners to dissociating conditions. The presence of interaction complex even under dissociating conditions can be taken to indicate an "irreversible" association. Optionally, the association is fully reversible. A fully reversible association for example is one in which the binding partners can be made to subsequently dissociate after association without retaining any measurable or significant amounts of interaction complex in the dissociated state.

Conversely, where dissociation of two binding partners is desired, the binding partners can be made to dissociate from each other. Optionally, this dissociation is reversible in that the dissociated binding partners re-associate after the dissociated binding partners are subjected to associating conditions. The presence of dissociated binding partners even under associating conditions can be taken to indicate an "irreversible" dissociation. Optionally, the dissociation is fully reversible. A fully reversible dissociation for example is one in which the dissociated binding partners subsequently re-associate after dissociation when subjected to associating conditions, without retaining any measurable or significant amounts of binding partners in the dissociated state.

Optionally, a fully reversible interaction is one in which the binding partners can be made to associate and dissociate repeatedly (e.g., 2, 5, 10, 30 or even 100 times) without any significant or measurable accumulation of interaction complex during dissociating conditions (indicating a fully reversible association), and/or dissociated binding partners during association conditions (indicating a fully reversible dissociation). For example, a system that displays similar ratios of recruited and released marker over a number of iterations can be deemed to be fully reversible. The number of iterations is for example 2, 5, 10, 50 or even 100 iterations. The ratio of recruited and released marker can for example be measured by comparing the concentration of free marker in red light and in infrared light.

If desired, the association or dissociation can be partially reversible, or a fully reversible interaction can be partially reversed by adjusting the parameters of light exposure, as discussed below. For example, the association or dissociation can be 50%, 60%, 70%, 80% or 90% reversible or reversed.

X. Regulation of Association

According to the invention, the overall extent of association between proteins or protein constructs can be precisely controlled in various ways, as defined below. Where desired, the extent of association can be precisely controlled by determining the exact parameters of wavelength, exposure time and/or intensity.

In one aspect, a substantial fraction, or a majority, or substantially all of the PHD is converted to one conformeric state. For example, about 5%, 10%, 20%, 30%, 40%, 50%, 60%, 70%, 80%, 90%, 95% or above 99% of the PHD is converted to one conformeric state. The conformeric state can be the Pfr state or the Pr state, as desired.

A. Control by Wavelength Selection

Under illumination with light of any wavelength, the two different populations of Pr and Pfr states will convert until they reach the equilibrium ratio that corresponds to the wavelengths of light used. Light in wavelength regions that have differences in spectral sensitivity will cause a dominance of Pr or Pfr form at equilibrium.

1. Activating Red Light:

For purposes of this application, red light includes those frequencies that maximally populate the Pfr state. For PhyB, the optimal frequency window is centered within 10 nm of 650 nm. Any light between 550 nm and 700 nm will preferentially populate the Pfr state. For the methods described herein, any visible light below 700 nm will suffice to induce a significant fraction of PHDs into the Pfr state, and optionally recruit a significant fraction of PIP-tagged recruitee constructs.

When it is desired to convert a majority or substantially all of the PHDs into the Pfr state, about 600-700 nm, for example about 630-690 nm, such as about 650, 655, 660, 665, 670, 675, 680, 685 or 690 nm wavelength can be used.

2. De-Activating Infrared Light:

IR light will generate a nearly pure population of "off" Pr phytochrome. Any light above 700 nm will work, with light in the further IR requiring greater intensities to achieve the same kinetic rate of off-switching. For example, a 20 nm bandpass filtered light centered at 750 nm, or a "RG9" long-pass filtered light that allows all light above 750 nm through unblocked, can be used.

When it is desired to convert a majority or substantially all of the PHDs into the Pfr state, about 700-800 nm, for example about 710-790 nm, such as about 710, 720, 725, 730, 735, 740, 745, 750, 755, 760, 770 or 780 nm wavelength can be used.

3. Non-Perturbing Green Safe-Light:

There is a window of frequencies that the Pr and Pfr phytochromes are relatively insensitive too, provided the light source is not too bright (laser illumination). This is the green "safe-light" frequency range and is optimally light within a 20 nm window centered at 550 nm.

4. Darkness:

If exposed to darkness, Pfr can be converted to Pr either by a slow thermal, non-photoinduced reaction over many hours or days (dark reversion).

B. Temporal Control

The methods discussed herein can allow extremely quick detection and/or control of protein interactions. In one aspect, binding between a first and a second protein can be quickly effected or impaired. The first protein optionally comprises a PHD and the second protein a PIP, or vice versa. The quick association and dissociation of PHDs and PIPs (and proteins comprising them) in response to light can allow control of interaction and/or localization within 1 minute, or sometimes within 10-20 seconds, and sometimes even within one second.

In one aspect, the extent of association, and optionally the localization, of a protein of interest can be temporally controlled by the methods described herein, by means of exposure to light. The forward reaction (Pr to Pfr) requires a few seconds to complete, whereas the reverse transformation (Pfr to Pr) is complete by 20 to 30 msec. Accordingly, the timing of association, and optionally the localization, can be controlled down to seconds. Such refined time control can also be used in a system where light is periodically applied, e.g., by employment of pulse signals or other oscillatory signals of light.

C. Spatial Control

In one aspect, the cellular localization of a first protein of interest can be modified by allowing or disallowing binding to a second localized protein (e.g., a protein comprising a subcellular localization tag). The first protein optionally comprises a PHD and the second protein a PIP, or vice versa. The quick association and dissociation of PHDs and PIPs (and proteins comprising them) in response to light can allow control of protein's subcellular localization within 1 minute, or sometimes within 10-20 seconds, and sometimes even within a second.

In another aspect, interaction between two proteins of interest can be selectively regulated within a localized portion of a cell by exposing only that portion of the cell to regulatory light. For example a portion of a cell can be exposed to "activating" red light that induces protein interaction while another portion of the cell can be simultaneously exposed to infrared light. In another example, the entire cell can be bathed in continuous "inactivating" infrared light, while a localized beam of activating red light is restrictively delivered to a specific portion of the cell at higher intensity, resulting in well-defined localization.

In other examples, the interaction between two proteins of interest can result in a detectable change within the cell, such as a change in cell morphology or behaviour. Regulation of such interactions can be used for example to control cell morphology or movements.

By exposing a cell or organism to focused red and/or infrared light, it is further possible to localize the association or recruiting (localization) region to a small, diffraction-limit-sized membrane region or a specific subcellular organelle in the cell. This can be on the order of centometers or millimeters (e.g., when exposing parts of an organism), down to micrometer or even sub-micrometer scales (e.g., when studying intracellular interactions or localization within subcellular compartments within a cell or membrane subdomains such as lipid rafts with slow diffusion rates).

1. Lasers

One light source for local activation can be a nitrogen pulsed UV dye-cell laser exciting a Rhodamine 650 dye which emits at 650 nm. One could also use any other laser with laser lines in the red region of the spectrum, such as a Ar/Kr 647 nm line. This laser beam is then guided optically to be aligned with the imaging axis of the microscope and to center the laser spot directly onto the sample along the Z dimension of this axis.

2. Mirrors

A second light source for spatially controlled activation and deactivation can be any system that uses a computer controlled spatial light modulator to project any coherent or noncoherent light source onto the sample being imaged by the appropriate microscope optics. An example of a spatial light modulation setup could employ a Digital Light Processing (DLP) chip modulating incoherent red and infrared IR light using a fast, millisecond shutter system.

D. Intensity

The intensity of light to which the cell is exposed can be used to control the extent of association, e.g., the proportion of molecules in an associated and unassociated state. For example, low-intensity red light will achieve only partial, titrated association. Total illumination doses less than 1,000 micromoles of photons per square meter can be regarded as low intensity red light. Total illumination doses greater than 10,000 micromoles of photons per square meter can be regarded as high-intensity light that is sufficient for 100% conversion. The intensity of red light required to convert a significant fraction or majority or substantially all PHDs to a Pfr state can be empirically determined using the methods taught herein and described in the Examples. Similarly, the intensity of infrared light required to convert a significant fraction, or majority, or substantially all of the PHDs to a Pfr state can be empirically determined.

The time of exposure to light can be varied according to effect needed and light intensity chosen, e.g., for about 1, 10 or 100 milliseconds, or about 1, 5 or 10 seconds, or about 1, 2, 3, 5, 10, 20 or 30 minutes, or about 1, 2, 3 or 5 hours, or about 1, 2, 3, or 5 days, or 1, 2 or 3 weeks. In am embodiment, the cell is exposed for a short time. For example, the cell can be exposed to ref or infra-red light for less than a minute, e.g., about 1, 5, 10, 20 or 40 seconds. The light can be delivered to a cell by known devices such as a laser, in one or more pulses or individual portions. For example, a UV-pumped red dye cell laser can shoot ultrafast pulses of light that last about 5 ns; these can be applied, e.g., at low intensity at about 20 Hz for about 5 s to minutes.

XI. Nucleic Acids and Vectors

The invention also includes nucleic acids encoding the proteins and protein constructs of the invention. In one aspect, the proteins and/or proteins constructs of this invention are synthesized using recombinant expression systems. For example, this involves creating a DNA sequence that encodes the desired protein(s), placing the DNA in an expression cassette under the control of a particular promoter, expressing the protein in a host, and, if desired isolating the expressed protein. Using the information provided herein, the nucleic acids can be prepared using standard methods known to those of skill in the art. For example, the nucleic acid(s) may be cloned, or amplified by in vitro methods, such as the polymerase chain reaction (PCR), the ligase chain reaction (LCR), the transcription-based amplification system (TAS), the self-sustained sequence replication system (SSR), etc. A wide variety of cloning and in vitro amplification methodologies are well-known to persons of skill. Examples of techniques sufficient to direct persons of skill through in vitro amplification methods are found in by J. Sambrook, E.F. Fritsch, and T. Maniatis, Molecular Cloning: A Laboratory Manual, ISBN-10: 0879693096.

DNA encoding desired proteins (e.g. HY2 family members) described herein can be prepared by any suitable method as described above, including, for example, cloning and restriction of appropriate sequences or direct chemical synthesis.

XII. Host Cells and Organisms

A variety of cells can be used. Useful cells can be eukaryotic, including yeast, algae, fungal, fish, insect, avian and mammalian cells. Prokaryotic cells include bacteria.

One or more proteins or protein constructs of the invention can be introduced into a host cell in a variety of ways. For example, a recombinant cell can be engineered that expresses one or more proteins or protein constructs. Alternatively, the proteins or protein constructs can be introduced by any known method, such as microinjection, transfection and/or transduction of nucleic acid and/or protein. Optionally, the host cell is cultured.

Where needed, the invention includes providing cells with chromophores (e.g., phytobilins) or precursors thereof that can form part of the PHD. For example, the cell can be engineered to contain one or more genes involved in chromophore biosynthesis, e.g., heme oxidase (HO) and/or phycocyanobilin:ferredoxin oxidoreductase (pcyA). Alternatively, chromophores can be isolated and purified as described in the Examples, and added to the extracellular environment, whereupon the chromophore is naturally taken up by cells.

Living or dead, e.g., freshly killed, organisms can also be used, either in whole or in part. The organism can comprise recombinant host cells that contain one or more nucleic acid or protein constructs of the invention. In one aspect, the organism can be a transgenic organism. Some organisms that are widely used in research include mice, rats, hamsters, monkeys, dogs, cats, and hydra. Animals that are naturally transparent at any stage of development can be especially useful in the invention, including zebrafish, jellyfish, and various embryos.

XIII. Uses

The methods, materials and systems of the invention can be used in a variety of ways. In an aspect, the invention can be used as a research tool to study the biological role of a protein or interest, or the role of an interaction between a first and second protein of interest. The invention can also be used to identify proteins that interact in a biologically significant manner with a protein of interest, in which a known protein of interest is attached to a PDF, and a variety of candidate proteins are attached in turn to a cognate PIP, or visa versa (similar to a two-hybrid assay). In another aspect, the invention can be used to identify mutants of a protein of interest that show different interaction from the wild-type protein with a second protein. In yet another application, the invention can be used to screen for potential modulators of a protein-protein interaction or a cellular pathway.

The invention can be used in a variety of settings. For example, the invention can be used in vitro with cultured cells, or in vivo using organisms into which cells containing or expressing protein constructs of the invention have been introduced. Alternatively, the organism can be a transgenic organism that expresses one or more protein constructs of the invention.

Diagnostic uses include the introduction of the protein constructs into cells taken from a patient to detect abnormal effects of the association or dissociation of the protein constructs.

A. Proteins of Interest

The invention can be used to study a wide variety of proteins that are capable of interacting with other proteins. In an embodiments, interactions such as dimerization or multimerization can be studied, wherein the first and second protein construct comprise the same protein of interest. In another variation, the first and second proteins are not involved in protein splicing.

In an embodiment, the first and/or second protein of interest is involved in cell signalling. Molecules involved in signalling include receptors (both at the cell surface and intracellular). Such receptors include G-protein coupled receptors, e.g., chemokine receptors; receptor tyrosine kinases, e.g., growth factor receptors, integrins and toll-like receptors. Signalling proteins downstream of receptors include intracellular proteins activated by a ligand/receptor interaction; these often possess an enzymatic activity. These include small G proteins such as the Ras, Rho, and Ral families, Guanine nucleotide exchange factors such as SOS, eIF-2B, Ras-GRF1, GOCRs and Kalinin. tyrosine kinases, heterotrimeric G proteins, small GTPases, various serine/threoine protein kinases, phosphatases, lipid kinases, and hydrolases. Some receptor-stimulated enzymes create specific second messengers including cyclic nucleotides, such as cyclic AMP (cAMP) and cyclic GMP (cGMP), Phosphatidylinositol derivatives, such as Phosphatidylinositol-triphosphate (PIP3), Diacylglycerol (DAG) and Inositol-triphosphate (IP3), IP3, controlling the release of intracellular calcium stores into the cytoplasm (see second messengers section later in this article).

Adapter proteins are another type of protein involved in signalling. Adapter proteins include GRAP—GRB2-related adaptor protein; GRAP2—GRB2-related adaptor protein 2; LDLRAP1—low density lipoprotein receptor adaptor protein 1; NCK1—NCK adaptor protein 1; NCK2—NCK adaptor protein 2; NOS1AP—nitric oxide synthase 1 (neuronal) adaptor protein; PIK3AP1—phosphoinositide-3-kinase adaptor protein 1; SH2B1—SH2B adaptor protein 1; SH2B2-SH2B adaptor protein 2; SH2B3-SH2B adaptor protein 3; SHB—Src homology 2 domain containing adaptor protein B; SLC4A1AP—solute carrier family 4 (anion exchanger), member 1, adaptor protein; and GAB2, GRB2-associated binding protein 2.

Many proteins involved in signalling possess specialized protein domains that bind to specific secondary messenger molecules. For example, calcium ions bind specifically to the EF hand domains of calmodulin, allowing this molecule to bind and activate Calmodulin-dependent kinase. PIP3, PIP2 and other phosphoinositides may bind to the Pleckstrin homology domains of proteins such as the kinase protein AKT.

Examples of specific signalling proteins of interest include a G protein, Rho Guanine nucleotide Exchange Factors (GEF), or any other signalling proteins of interest. Rac1 [Entrez Gene ID: 5879], Cdc42 [Entrez Gene ID: 998], RhoA [Entrez Gene ID: 387]. Examples of GEFs include Tiam [Entrez Gene ID: 7074], Intersectin [Entrez Gene ID: 6453], and Tim [Entrez Gene ID: 7984]. Other Signalling Factors include Nckap1L (Hem1) [Entrez Gene ID: 3071], G-gamma2 [Entrez Gene ID: 54331], and inter-SH domain (residues 420-615) from p85alpha [Entrez Gene ID: 5295].

Biologically significant effects that result from signal transduction include activation of genes, alterations in metabolism, the continued proliferation and death of the cell, and the stimulation or suppression of locomotion.

XIV. Kits

The invention also includes kits containing any of the proteins, protein constructs, nucleic acids, cells, reagents or materials of the invention or any combination thereof. The kit optionally contains instructions that instruct a user to introduce proteins, protein constructs, nucleic acids, and/or reagents of the invention into cells and/or to regulate association of the proteins or protein constructs of the invention by regulating exposure to light (e.g., red and/or infrared light).

EXAMPLES

Example 1

Materials and Methods

Design and Construction of Plasmids.

Figure 8:
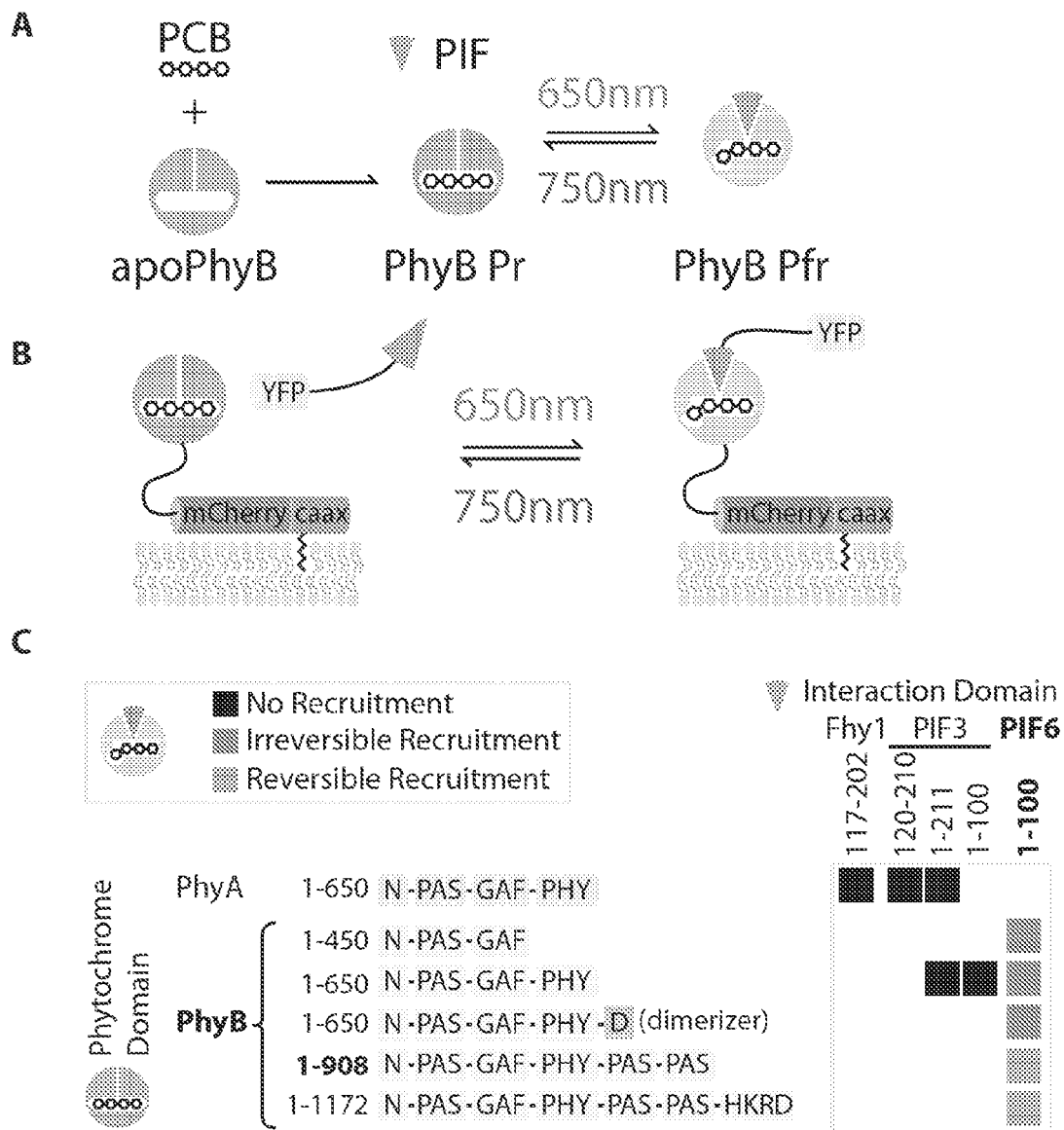
FIG. 8: The phytochrome-APB interaction can by used to reversibly translocate proteins to the plasma membrane in a light-controlled fashion. (a) apoPhyB covalently binds to the chromophore phycocyanobilin (PCB) to form a light-sensitive holoprotein. PhyB undergoes conformational changes between the Pr and Pfr states catalyzed by red and infrared light, reversibly associating with the PIF domain only in the Pfr state. (b) This heterodimerization interaction can be used to translocate a YFP-tagged PIF domain to PhyB tagged by mCherry and localized to the plasma membrane by the C-terminal caax motif of Kras. (c) Phytochrome and PIF domains functional in mammalian cells were tested by their ability to reversibly recruit YFP to the plasma membrane under the action of red and infrared light. Of previously published PIFs, only the PhyB interacting 100-aa N-terminus of PIF6 showed visible recruitment activity in mammalian cells with confocal microscopy. For example, no detectable interaction was seen between any PIF3 construct and any PhyB contruct tested. In addition, the recruitment of PIF6 was irreversible with the previously used PhyB fragments PhyB(1-650) and PhyB (1-450). A PhyB construct harboring the tandem PAS repeat (PhyB 908) showed reversible interaction under infrared light and freed YFP back into the cytosol.
Figure 9:
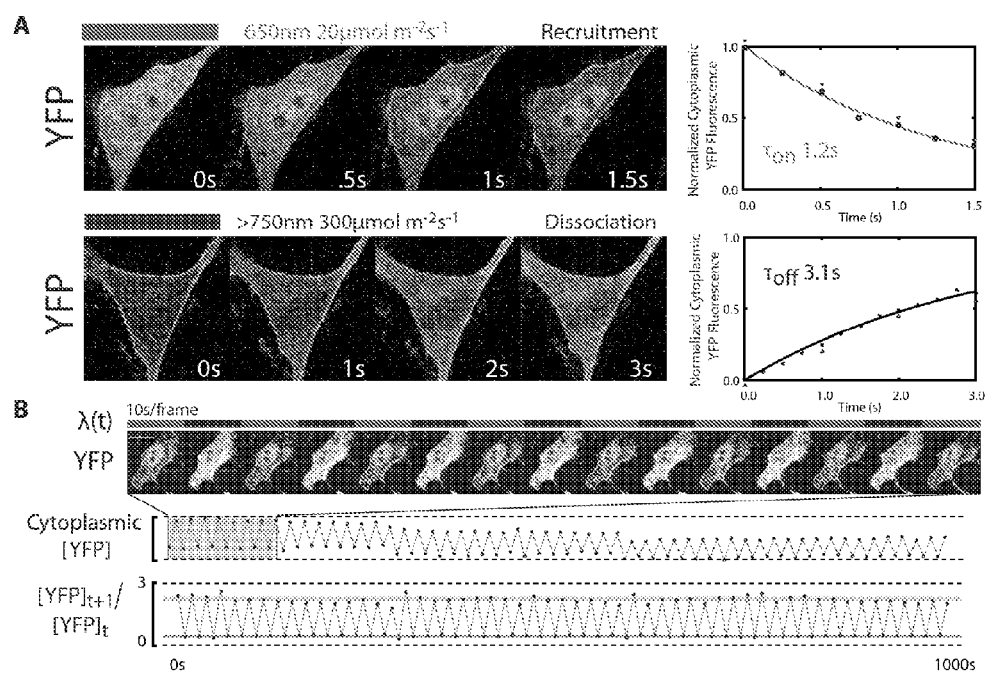
FIG. 9: Confocal microscopy reveals the quick kinetics and robustness of the photoswitchable membrane recruitment system. (a) Confocal microscopy of NIH3T3 cells reveals rapid whole cell translocation of YFP between cytosol and plasma membrane under red and infrared light. Fitting exponentials to the cytoplasmic depletion of YFP in these series gives typical time-constants of 1.2 s for recruitment and 3.1 s for dissociation. Arrows in graphs mark the timepoints shown. (b) Rapid alternation between the two light frequencies can generate oscillations in the cytoplasmic concentrations of YFP. The absolute cytoplasmic concentration of YFP for this series is plotted along with the ratio change between timepoints to adjust for photobleaching and cell-drift. The red and grey bars represent the standard deviations of the recruited and released cytosolic fluorescence, demonstrating near-fixed recruitment ratios over more than a hundred iterations. Scale bars 20 µm.
Figure 11:
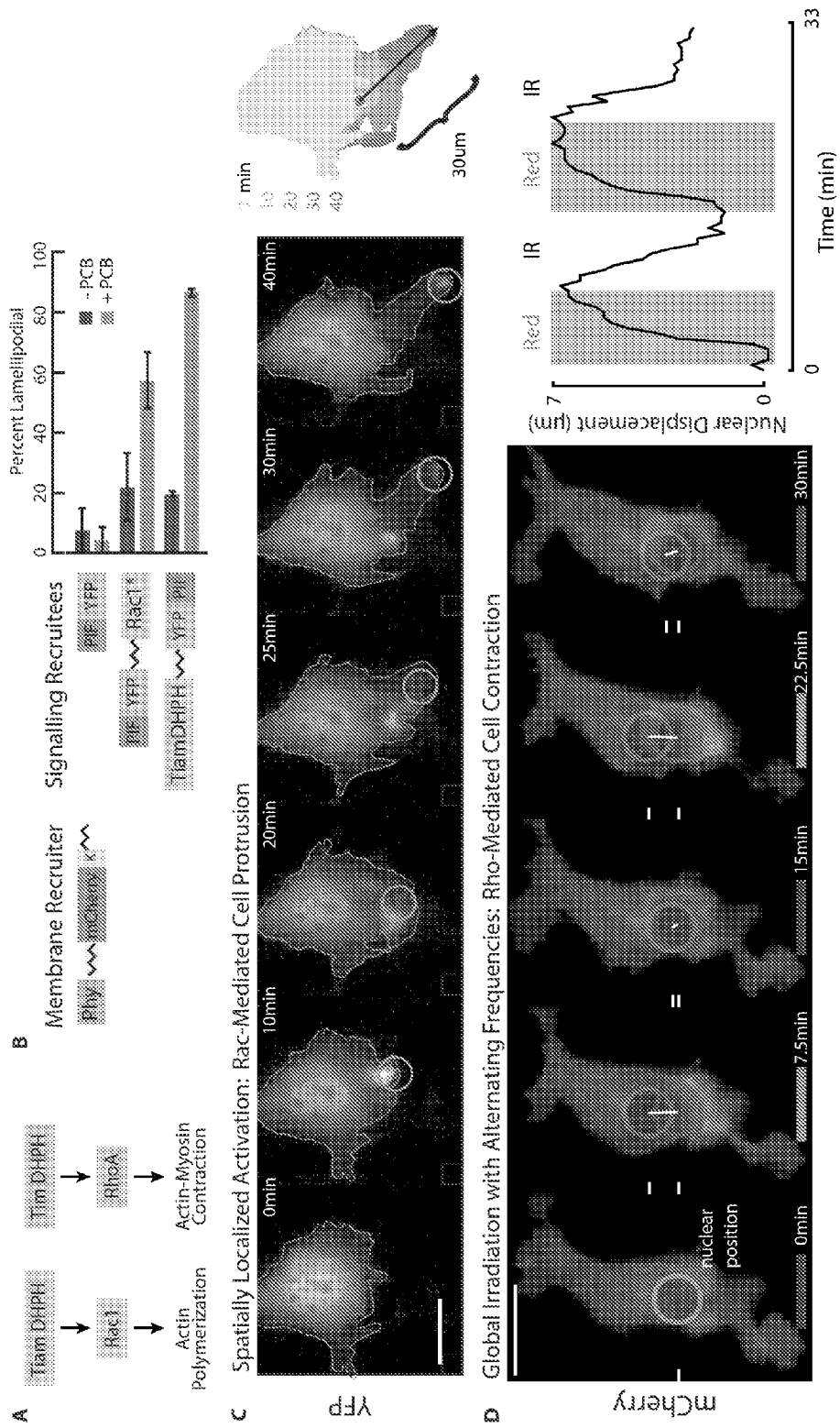
FIG. 11: Rho-family G-protein signalling can be controlled by the light-activated translocation system. (a) The catalytic DH-PH domains of RhoGEFs Tiam and Tim activate their respective G-proteins Rac1 and RhoA which in turn act through effector proteins to modify the actin cytoskeleton. (b) Recruitee constructs with constitutive Rac1(Q61L, no caax) or Tiam DH-PH domains were assayed for their ability to induce lamellipodia in NIH3T3 by exposing serum-depleted cells transfected with the indicated constructs to red (650 nm) light and counting the percentage of cells that produced lamellipodia within 20 min under live microscopy. Error bars s.e.m., (n=2, avg. 30 cells) (c) Local induction and 'extrusion' of lamellipodia in live NIH3T3 cells was demonstrated by globally irradiating the whole sample with a infrared (750 nm) light source while focusing a red (650 nm) laser onto a small portion of the cell as in 2a and slowly extending this red-targeted region from the cell body. Superimposed out-lines of the cell show directed extension 30 μm along the line of light movement. (d) Periodic membrane recruitment of Tim DHPH by alternating global exposure to red and infrared light causes rhythmic contraction of a NIH3T3 cell. The nuclear position was measured by fitting a circular mask by hand to the nucleus and recording the centroid. The nuclear displacement is plotted against time to show the tight correlation of contraction with red light exposure. Scale bars 20 μm.

Most constructs were assembled whole by two-step overlap PCR and subcloned into the mammalian vector pcDNA3 or a modified version with a truncated SV40 promoter (10-fold lower expression relative to CMV). Unique cut-sites flanked all fused domains such that some constructs were assembled by replacing signalling domains by standard subcloning.

pAL113: p CMV-PhyBNT(Y276H)-10aaLinker-mCFP-HrasCT
pAL161: pCMV-PhyB(1-450)-10aaLinker-mCherry-Kras4BCT; FIG. 8c
pAL117: pCMV-PhyB(1-650)-10aaLinker-mCherry-Kras4BCT; FIG. 8c
pAL148: pCMV-PhyB(1-650)-Gal4DD-10aaLinker-mCherry-Kras4BCT; FIG. 8c
pAL149: pCMV-PhyB(1-908)-10aaLinker-mCherry-Kras4BCT; All Figs
pAL162: pCMV-PhyBFL-10aaLinker-mCherry-Kras4BCT; FIG. 8c
pAL140: pCMV-PhyA(1-650)-10aaLinker-mCherry-Kras4BCT; FIG. 8c
pAL139: pCMV-mYFP-Fhy1CT; FIG. 8c
pAL138: pCMV-PIF3APA-mYFP; FIG. 8c
pAL130: pCMV-PIF3NT-mYFP; FIG. 8c
pAL100: pCMV-PIF3APB-mYFP; FIG. 8c
pAL101: pCMV-PIF6APB-mYFP; FIG. 8c, 11b
pAL175: pASV40-mYFP-PIF6APB; FIG. 9, 10
pAL105: pCMV-PIF6APB-mYFP-20aaLinker-Rac1(Q61L)ΔCT; FIG. 11b
pAL167: pCMV-TiamDHPH-20aaLinker-mYFP-PIF6APB; FIG. 11b
pAL188: pASV40-TiamDHPH-20aaLinker-mYFP-PIF6APB; FIG. 11c
pAL190: pASV40-TimDHPH-20aaLinker-mYFP-PIF6APB; FIG. 11d Phytochrome, PIF Domains:

PhyB-CBD (PhyB450NT), PhyB-NT (PhyB650NT), PhyB-908NT, and PhyB-FL domains were amplified by PCR from vector PhyBFL-GBD; this vector contains full-length phyB [Entrez Gene ID: 816394] cDNA from *Arabidopsis thaliana*. PhyA-NT (1-650) was cloned from previously subcloned cDNA. PIF3NT, PIF3APA (aa120-210), PIF3APB (PIF3-100NT) and PIF6APB (PIF6-100NT) domains were amplified by PCR from vectors PIF3-GAD and PIF6APB, respectively; these vectors contain subsequences of the PIF3 [Entrez Gene ID: 837479] and PIF6 [Entrez Gene ID: 825382] genes from *Arabidopsis thaliana*. All three vectors were gifts from Peter Quail. *Arabidopsis* Fhy1CT(117-202) [Entrez Gene ID: 5007942] was amplified from *Arabidopsis thaliana* cDNA.

Linker Domains

The linker domains used are standard polyglycine-serine flexible linkers and were made by oligo annealing: 10aa-linker: DSAGSAGSAG [gat agt gct ggt agt gct ggt agt gct ggt], 20aa-linker: SAGGSAGGSAGGSAGGSAGG [agt gct ggt ggt agt gct ggt ggt agt gct ggt ggt agt gct ggt ggt agt gct ggt] (SEQ ID NOS:11, 10, 13 and 12) Dimerization domain The Gal4 dimerization domain$_1$ (residues 50-106) was cloned from a *Saccharomyces cerevisiae* cDNA library.

Localization Domains

Small C-terminal localization tags were created by oligo annealing: Hras [Entrez Gene ID: 3265] palmitoylation CaaX sequence (GCMSCKCVLS), [ggc tgc atg agc tgc aag tgt gtg ctc tcc], Kras4B [Entrez Gene ID: 3845] polybasic CaaX terminus (SKTKCVIM) [ggt aaa aag aag aaa aag aag tca aag aca aag tgt gta att atg] (SEQ ID NOS:14-17)

Fluorescent Proteins mCFP and mYFP (ECFP and EYFP with monomerizing A206K mutation) were amplified by PCR from Invitrogen vectors. mCherry was amplified by PCR from vector supplied by Rogen Tsien.

Rho G-Proteins and GEFs

Rac1-Q61L, without its C-terminal CaaX motifs was cloned by PCR from a CFP-linked vector that was a gift of Tobias Meyer. These were produced by making Q61L activating point mutants in the wild-type sequence of Rac1 [Entrez Gene ID: 5879]. DHPH domains from human RhoGEFs Tiam [Entrez Gene ID: 7074], and Tim [Entrez Gene ID: 7984] were amplified by PCR from vectors carrying previously subcloned copies of these cDNAs.

Mammalian Promoters

The standard CMV promoter from the pcDNA3 vector was used in most constructs. In some plasmids a truncated sv40 promoter was used instead to lower expression levels of recruitee constructs in transiently transfected cells (10-fold lower expression than CMV).

Phycocyanobilin (PCB) Purification.

50 g of dried Spirulina lysate (Seltzer) was resuspended in 1.5 L doubly distilled water (30 mL/g pellet), shaken for 10 minutes, then spun at 8000 rpm for 1 hour. The dark green pellet was discarded and the cyan supernatant was treated with 15 g TCA (1% w/v) to precipitate soluble protein. This solution was stirred at 4° C. for an hour then spun at 8000 rpm for 10 minutes. The pellet was collected and washed three times with 1.5 L methanol to remove free tetrapyrroles and spun at 8000 rpm for 10 minutes (until supernatant was clear). The pellet was collected and subjected to methanolysis in 500 mL methanol by refluxing at 70° C. for eight hours, great care was taken from this point on to shield the free PCB-containing mixture from direct light by wrapping glassware in aluminum foil or by using a green safelight in a darkroom. The remaining pellet was subjected to a second, identical methanolysis for a second pool that was further handled in parallel with the first. Each methanol extraction was dried using a roto-evaporator and resuspended in doubly distilled water. This was extracted with 250 mL chloroform and dried with a roto-evaporator to a residue. The residue was resuspended in 5 mL DMSO, and this final solution's PCB concentration was quantified by spectroscopy and stored at −80° C.

Cell Culture and Transfections.

NIH 3T3 cells were obtained from ATCC and maintained in DMEM supplemented with 10% (v/v) BCS and antimicrobials at 37° C. in a humidified, CO2-controlled (5%) incubator. For experiments, 150,000 3T3 cells were plated on poly-d-lysine coated glass-bottomed petri dishes (Mattek) at least 12 hours before transfection. Transfections were performed with Lipofectamine 2000 (Invitrogen) at a 3:1 µL/µg ratio of reagent to DNA mixed in Optimem for 25 minutes and added directly to cells for five hours before washing reagent out with serum-containing media. Microscopic observations took place at least sixteen hours post-transfection. Serum starvation was performed where indicated by a stepwise replacement of serum-containing media by DMEM supplemented with 0.2% (w/v) fatty-acid free BSA over an hour, followed by five hours of starvation. PCB was added to cells at least half an hour before experiments by first diluting DMSO stock in DMEM and then adding to cells for a final concentration of 2.504. The weakly fluorescent PCB containing media was swapped immediately before imaging with HBSS supplemented by 0.2% fatty-acid free BSA.

Global Recruitment Assays.

Global recruitment assays were performed at 37° C. on a spinning disk confocal microscope consisting of a Nikon TE2000-U inverted microscope surrounded by a temperature-control chamber, equipped with a Yokogawa CSU22 confocal scanning unit (Solamere Technology Group) using Ar and Ar/Kr laser lines 568 nm, 488 nm. Images were captured with a Photometrics Cascade II EMCCD camera. Cells were exposed to activating or deactivating wavelengths obtained by filtering brightfield light with either a 650 nm 20 nm-bandpass filter (Edmund Optics) or an IR long-pass RG9 glass filter (Newport). Total photon fluence was measured at the sample plane by using a portable calibrated fiber-optic spectroradiometer (EPP2000C, Stellarnet Inc). To measure kinetics of recruitment and release, cells were exposed to fixed periods of red or infrared light, returned to fully-recruited or fully-released equilibrium by exposure to 10 s of the opposite wavelength of light, then exposed again for a longer fixed period of the original wavelength in a loop. Such iterative measurements helped to eliminate the strong activating perturbations induced by the imaging light itself.

Localized Recruitment and Signal Induction.

Localized recruitment assays were performed at 37° C. using total internal reflectance (TIRF) microscopy on a Nikon TE2000E inverted microscope surrounded by a temperature-control chamber, equipped with a Nikon laser TIRF illuminator (Nikon 60× Apochrom 1.49NA). Ar laser lines 488 nm, and 514 nm and solid state 561 nm lasers were used through a LEP MAC5000 shutter system. Images were collected with a Photometrics Cascade II EMCCD camera. Local induction was performed with a MicroPoint microscope laser system (Photonic Instruments) using a pulse UV-pumped Rhodamine 650 nm dye cell laser. The illumination point was made parfocal with microscope optics by test-ablation of a metal-sputtered glass slide. To locally recruit fluorescently tagged signalling factors, continuous 20 Hz pulses of the 650 nm light at low intensity were centered on a patch of plasma membrane while simultaneously irradiating the whole cell with inhibitory IR light from a brightfield source at maximal intensity filtered by an RG9 IR long-pass glass filter (Newport).

Patterned Membrane Recruitment

Recruitment of YFP-tagged APB to patterned regions of the cell membrane was performed at room temperature using total internal reflectance (TIRF) microscopy on a Nikon TE2000E inverted microscope equipped with a Nikon laser TIRF illuminator (Nikon 60× Apochrom 1.49NA). Ar laser lines 488 nm, and 514 nm and solid state 561 nm lasers were used and emission light filtered by a Sutter Lambda 10-3 Filter Wheel. Images were collected with a Photometrics Cascade II EMCCD camera. To produce patterned Red/IR profiles at the cell surface, alternating 650 nm and 750 nm light was produced using 20 nm bandpass filters (Chroma) with a broad-spectrum arclamp in a Lambda DG-4 source.

These wavelengths were patterned by use of a commercial digital micromirror device brought into a conjugate focal plane with the sample. (Mosaic Digital Diaphragm, Photonic Instruments) The illumination frequencies were switched at the maximum update speed for the device, which was roughly 8 Hz. Illumination, acquisition and light patterning of the glider motif were orchestrated by a custom script written in Metamorph.

Morphological Induction Assays.

Morphology induction assays were performed by exposing cotransfected, PCB-preincubated (30 min) or PCB-free control cells to red light while observing on a Nikon TE2000E inverted microscope in widefield with a 514/561 dichroic mirror and YFP and mCherry channel emission light filtered by a Sutter Lambda 10-3 Filter Wheel. Images were collected with a Photometrics Cascade II EMCCD camera. The constructs were scored by counting the percentage of cotransfected cells exhibiting lamellipodia within the twenty-minute observation window.

Supplemental Calculation

Membrane Capture Time Constant for Perfect Spherical Absorber

An approximate time constant for capture of molecules diffusing in a cell with diffusion constant D to a perfectly absorbing spherical membrane (radius R) can be easily calculated by solving the poisson equation for the "mean-first-capture-time field". Mean time equation for a particle encountering a non-attracting boundary for the first time by diffusion (diffusion constant D):

$$D\Delta W + 1 = 0$$

W is mean time to encounter (shown by electrostatic analogy). Solving this equation for the inside of a spherical cell of radius R yields a solution of the form:

$$B - A/r - r^2/(6D)$$

Boundary conditions (mean-capture-time at r=R is zero, continuity requires derivative must be zero at origin) fix constants for a solution:

$$(R^2 - r^2)/(6D)$$

Averaging this value over the inside of the spherical cell yields an approximation for the time constant for membrane capture:

$$R^2/(15D)$$

For typical cell values: (20 μm cell diameter, 30 $\mu m^2 s^{-1}$ D for cytoplasmic GFP) this equaled 0.22 seconds. Given that this calculation assumes capture at the first membrane-encounter it serves as a lower bound.

Example 2

Regulation of Association by Light Exposure

FIG. 3A shows a schematic of the phytochrome-pif protein-protein interaction. This interaction can be verified to function in any cell with a well defined cytoplasm and plasma membrane. The phytochrome domain is constitutively localized to the plasma membrane while the PIF domain is cytoplasmic. Induction of association following the "Global Recruitment Assay" depletes the cytoplasm of the soluble PIF domain if the interaction is functional. FIG. 3B shows this transition schematically, FIG. 3C shows one of many examples of near total cytoplasmic depletion, demonstrating association under red light exposure, none under infrared light exposure.

Example 3

Temporal Control of Association

By applying the same procedure as in the previous Example 1, but with a temporally controlled series of pulses of red and infrared light, one can cause an oscillatory association of the two proteins. FIG. 4 shows timecourse snapshots of an oscillatory membrane recruitment of YFP.

Example 4

Spatial Control of Association

Localized Recruitment.

Localized recruitment assays were performed at 37° C. using total internal reflectance (TIRF) microscopy on a Nikon TE2000E inverted microscope surrounded by a temperature-control chamber, equipped with a Nikon laser TIRF illuminator. Ar and Ar/Kr laser lines 561 nm, 488 nm, and 514 nm were used through a LEP MAC5000 shutter system. Images were collected with a Photometrics Cascade II EMCCD camera. Local induction was performed with a MicroPoint microscope laser system (Photonic Instruments) using a pulse UV-pumped Rhodamine 650 nm dye cell laser. The illumination point was made parfocal with microscope optics by test-ablation of a metal-sputtered glass slide. To locally recruit fluorescently tagged signalling factors, continuous 20 Hz pulses of the 650 nm light at minimal intensity were centered on a patch of plasma membrane while simultaneously irradiated the whole cell with inhibitory IR light from a brightfield source at maximal intensity filtered by an RG9 IR long-pass glass filter (Newport).

The above protocol was followed to localize YFP tagged by PIF6APB to the plasma membrane dynamically. FIG. 5A shows a schematic of the protocol, while FIG. 5B shows several frames from a timecourse showing a moving point of localized membrane-recruited YFP.

Example 5

Recruitment of Active Signalling Molecule to Subcellular Compartment

Morphological Induction Assays.

Morphology induction assays were performed by exposing transfected, PCB-preincubated cells to light from either 650 nm (B5b-436-30 Roithner Lasertechnik) or 750 nm (LED750-03AU Roithner Lasertechnik) LEDs for an hour at 37° C. in a humidified, CO2-controlled (5%) incubator. Cells were then immediately fixed for 10 minutes with 4% (v/v) EM-grade formaldehyde in cytoskeleton buffer (10 mM MES/pH 6.1, 138 mM KC1, 3 mM MgCl, 2 mM EGTA, 0.32M sucrose). Cells were washed twice with PBS and either imaged immediately using standard epifluorescent microscopy or stored at 4° C. for no more than a week before microscopic analysis. Percentage of transfected cells possessing morphological phenotype (lamellipodia, filopodia) in each case were scored manually.

The above morphological induction assay was used to test if membrane recruitment of the signalling factor TiamDHPH allowed it to activate its membrane-localized partner Rac and induce lamellipodia. FIG. 6 shows the result from one IR vs. Red induction, clearly the Red exposed cells have had lamellipodia formation induced in them, while infrared exposed cells are quiescent.

Localized induction of signalling with this protein construct was then tested by performing the same protocol as in example 3 "Localized Recruitment". FIG. 7A shows the schematic of this process, while FIG. 7B shows snapshots from a timecourse demonstrating localized induction of a lamellipodia on one side of the side where Red light was shone as a point source (arrow in figure). This demonstrates the feasibility of localized induction of signalling cascades at micrometer resolution.

Example 6

Design of a Modified Light-Control System (GELI) that Includes Robust Yet Reversible Binding As detailed below, we modified the interaction system to enable its spatiotemporal control in experiments with live mammalian cells. We first confirmed that PhyB could covalently bind externally supplied PCB chromophore in mammalian cells by utilizing a PhyB mutant (Y276H) that fluoresces at far-red frequencies in the PCB-coupled state only. NIH3T3 cells transfected with this construct show fluorescence after only 30 min of exposure to 5 μM PCB, confirming rapid autoligation at physiological conditions. (data not shown) Multiple potential phytochrome-PIF pairs were screened by a fluorescence translocation assay in NIH3T3 cells with confocal microscopy. We measured the red-light induced translocation of Yellow Fluorescent Protein (YFP) fused to PIF domains to coexpressed phytochrome domains fused through a flexible linker to mCherry and localized to the plasma membrane by a C-terminal polybasic, prenylation sequence from Kras. (FIG. 8b). Of all previously reported PIF domains only the N-terminus of PIF6 is strong enough to cause significant translocation of YFP to the membrane. (FIG. 8c) However, its interaction with the PhyB photosensory core (residues 1-650) was found to be irreversible in infra-red light.

In contrast, another PhyB construct which contained residues 1-908 of Phy B (1-908), including the tandem C-terminal PAS domains was found interact in a fully reversible manner with PIF6. By testing various PhyB contructs, we determined that the PAS domains conferred rapid photo-reversibility under infra-red light, underlining the importance of these domains for reversible signalling. We refer to the modified PhyB-PIF6 interaction system, which is both robust enough to result in significant and detectable interaction in vivo and is also fully reversible, as the genetically-encoded lightswitch interaction module GELI.

Example 7

Precise and Reversible Spatiotemporal Control of Protein Interactions Using the GELI System This example demonstrated how the GELI system achieved precise and reversible spatiotemporal control of protein interactions with spatial resolution in the scale of 1-10 micrometers and time resolution on the order of a second.

Using this optimized GELI we observed rapid translocation to the plasma membrane under dilute red light (650 nm 20 μmol m$^{-2}$ s$^{-1}$) and from the membrane under infra-red light (>750 nm 300 μmol m$^{-2}$ s$^{-1}$). (FIG. 9a) (These photon fluxes were tiny compared to those typical for GFP excitation: 40 mmol m$^{-2}$ s$^{-1}$ from an arc-lamp or 10$^4$ mol m$^{-2}$ s$^{-1}$ from an argon laser). Kinetic measurements of the GELI-induced cytoplasmic depletion of YFP under maximum illumination yielded translocation time constants of 1.3±0.1 s (s.d. n=3) for membrane recruitment and 4±1 s (s.d. n=3) for membrane release (FIG. 9a), demonstrating second-timescale control. These rates were an order of magnitude faster than previous chemically-induced translocation systems and were very near the physical limits for whole-cell diffusion. The GELI-induced translocation proved very robust—it could be cycled over a hundred times by alternating red and infrared illumination with no measurable decrease in recruitment ratios over time, despite many cycles of imaging at photon fluxes far higher than those phytochromes are exposed to in natural lighting conditions. (FIG. 9b)

The rapid forward and reverse kinetics of GELI allow for fine spatial control of membrane recruitment by simultaneously exposing cells to patterned light at the two antagonizing wavelengths. In NIH3T3 cells coexpressing the above YFP-recruitment pair, a nitrogen dye cell laser was used to deliver pulses of "activating" red light (650 nm, 20 Hz) to a focused point on the sample plane, while the whole sample was bathed in continuous "inactivating" infrared light obtained by filtering the microscope brightfield source (>750 nm). (FIG. 10a) When the cell membrane is imaged by total internal reflectance (TIRF) microscopy we observed a sharp spot of membrane-localized YFP several microns in diameter around the irradiated point. (FIG. 10c) The rapid 'off' kinetics of GELI trapped the membrane-recruited YFP pool to this spot, since any YFP diffusing away was dissociated from the membrane by the surrounding infrared light. The observed spot of recruited YFP could be rapidly relocated across the cell by repositioning the point of incident light.

Figure 10:
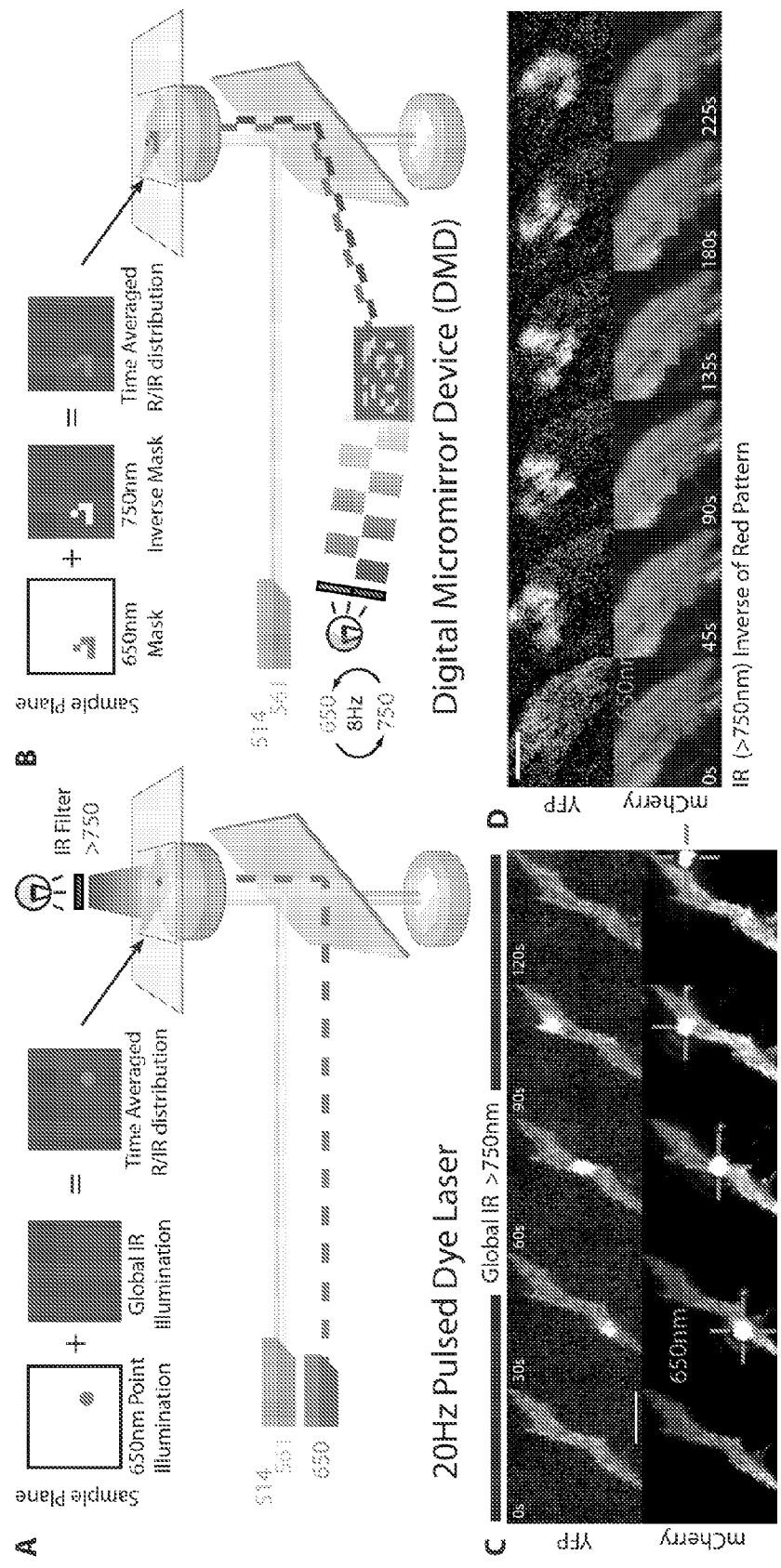
FIG. 10: Recruitment to the plasma membrane can be controlled spatially by simultaneously irradiating cells with patterned red and infra-red light. (a) A nitrogen dye cell laser exciting a 650 nm rhodamine dye was focused onto the sample plane of the microscope at 20 Hz while IR-filtered white light continuously bathed the entire sample. (b) A digital micromirror device focused onto the sample plane was used to send high-resolution patterns of alternating 650 nm/750 nm light from a DG-4 source into the microscope under software control at a 8 Hz switching frequency. This results in time-averaged complementary red and infra-red distributions on the sample plane. (c) TIRF imaging of localized membrane recruitment by a point source as in a shows highly localized YFP recruitment. The recruited YFP spot's diameter is roughly 3 µm and can be quickly moved by repositioning the laser. The final frame shows that the YFP spot is not merely bleed-through of the excitatory laser light, but genuine local fluorescent protein recruitment. (d) TIRF movies of structured membrane recruitment by rapidly oscillating inverted masks of red and infrared light by a digital micromirror device as in b were collected, revealing a faithful reproduction in the recruited YFP distribution of a movie of the cellular automaton 'game-of-life glider' that was projected. Scale bars 20 µm.

We further tested a second, more versatile method of controlling the distribution of both light frequencies on the cell membrane by using a digital micromirror array to project patterned light onto the sample plane of the microscope at micron resolutions. By alternately irradiating the sample with 650 nm light reflected from an array pattern and 750 nm light reflected from that pattern's inverse, we "painted" high-resolution inverse distributions of Pfr and Pr phytochrome on the membrane of the cell. (FIG. 10b) Indeed, even at modest switching rates (8 Hz), we could faithfully project a simple pixel-based movie into the membrane-recruited YFP distribution of a NIH3T3 cell. TIRF imaging revealed fine features at five microns, demonstrating an unprecedented degree of control over protein localization in living cells. (FIG. 10d).

We then chose to focus on spatiotemporal control of the Rho-family GTPase Rac, given its central role in the dynamic spatial regulation of the actin cytoskeleton at the leading edge in motile cells. We also chose to apply GELI to a membrane recruitment system because many signalling proteins are, at least in part, activated by interactions that relocalize them to the membrane. For example, chemically induced can generate global morphological changes. We found that GELI-induced membrane translocation of the rho- and ras-family small G-proteins or the guanine nucleotide exchange factors (GEFs) that activate them could generate global morphological changes similar to that obtained in chemically-induced systems described previously, but with much higher spatial and temporal resolution. (FIG. 11a).

Two types of gated-recruitment constructs were made, with either cytoplasmic Rac1 (a constitutively active Q61L mutant lacking its native prenylation sequence) or the isolated catalytic module (the DH-PH domain) of the Rac GEF Tiam. These were tested for activity by first observing the global morphological changes that occurred in transfected, serum-depleted NIH3T3 cells when the entire field is exposed to red light. Global Rac1(Q61L) recruitment caused a moderate increase in lamellipodial activity in depleted cells, while recruitment of the upstream Tiam DHPH domain caused a pronounced ruffling phenotype within minutes in the majority (>80%) of cotransfected cells, compared to YFP-only recruitment or control cells lacking the PCB chromophore. (FIG. 11b). This potent effect of recruiting the Tiam GEF activity to the membrane was similar to that observed using chemical dimerizers.

Given the strong global morphological effects of Tiam DH-PH domain membrane translocation, we then tested the effects of spatially localized light-activated translocation. Red laser stimulation was used for localized recruitment of the Tiam DH-PH domain in serum-depleted NIH3T3 cells (within a background of global repression by infrared light), resulting in a rapid, highly-localized lamellipodial 'bloom'. By slowly extending the point of activating light away from the cell, we could "draw out" an extended process up to 30 μm from the main body of the cell that was stable after the light had been withdrawn. The use of the GELI system thus created a 'morphological lithography' of light-sculpted cell geometries and intercellular connections. (FIG. 11c). We further tested a second RhoGEF DH-PH domain from Tim which specifically activates RhoA. Periodic recruitment of the Tim DH-PH construct under alternating global red and infrared irradiation induced a periodic contraction of the cell that was tightly correlated with recruitment. (FIG. 11d).

Example 8

Validation in Yeast

The phytochrome recruitment construct used in previous demonstrations, a single polypeptide consisting of PhyB1-908, a 20AA flexible linker, RFP fluorophore, and a Kras CAAX C-terminal plasma-membrane localization tag were introduced via standard protocols as a stable integrant into the yeast (saccharomyces cerevisiae) genome under the control of a strong, constitutive Adhl promoter. The YFP-pif6apb construct was similarly introduced by standard protocols as a genomic integrant under the control of a galactose-sensitive Gall promoter, allowing the levels of this phytochrome interacting protein to be varied by varying the external concentration of galactose in the growth media.

Figure 12:
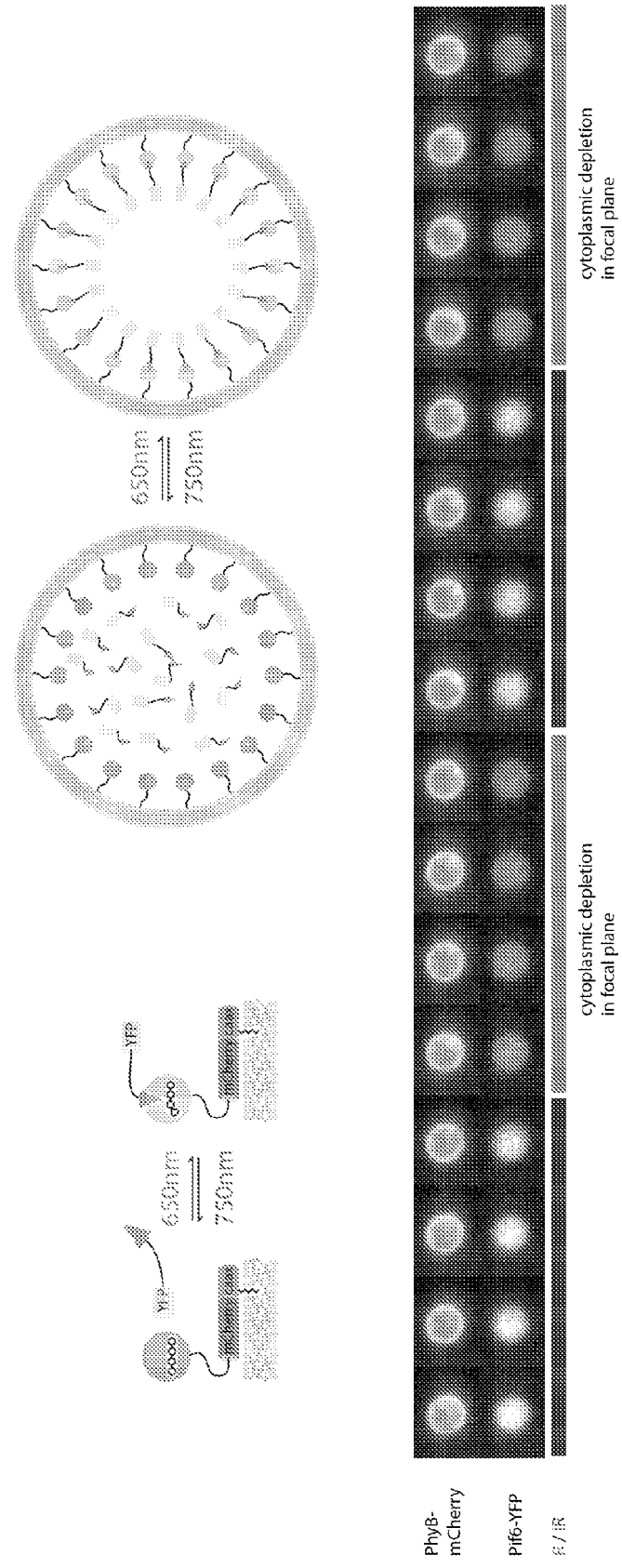
FIG. 12. Validation of systems in yeast. (a) Schematic of experimental system used showing membrane recruitment in response to red-light stimulation and membrane dissociation in response to infrared light stimulation. (b) Timecourse showing (top) the mCherry labelled phytochrome recruiter on plasma membrane and (bottom) the cytoplasmic PIF6-tagged YFP oscillating in concentration in the imaged slice in response to varying red and infrared light exposure.

The yeast cells stably expressing these constructs were exposed to 0.2% to 2% (weight volume) galactose overnight, and then perturbed and imaged as in [0142] but using widefield fluorescence imaging instead of TIRF. By imaging a focal slice of the yeast cells, we could see visible cytoplasmic depletion and restoration of YFP levels indicating sizable, reversible and rapid membrane translocation, as shown in FIG. 12.

Although the foregoing invention has been described in detail for purposes of clarity of understanding, it can be obvious that certain modifications can be practiced within the scope of the appended claims. All publications, documents, accession numbers and the like cited above are hereby incorporated by reference in their entirety for all purposes to the same extent as if each were so individually denoted. If more than one version of sequence is associated with the same accession number at different times, reference to that accession number means the version associated with it at the time of filing the present application dating back to any priority application that also includes that accession number. Unless otherwise apparent from the context, any step, feature, element or embodiment can be used in combination with any other.

What is claimed is:

1. A method of spatially and/or temporally regulating an interaction between a first protein sequence and a second protein sequence within a cell by light, comprising:
    a) providing in the cell a first protein construct which comprises the first protein sequence and a phytochrome domain (PHD), wherein the phytochrome domain:
        (i) can reversibly convert from a red-light absorbing conformer (Pr state) to a far-red light-absorbing conformer (Pfr state) upon exposure to red light, and
        (ii) can reversibly convert from the Pfr state to the Pr state upon exposure to infra-red light;
    b) providing in the cell a second protein construct which comprises the second protein sequence and a phytochrome domain-interacting peptide (PIP) that can bind selectively to the Pfr state, but not to the Pr state, of the phytochrome domain; and
    c) regulating the interaction between the first protein construct and the second protein construct by regulating cell exposure to red light and/or infra-red light, and
    d) detecting a change in the interaction between the first protein construct and the second protein construct within the cell, wherein:
        (i) the PHD comprises a partial fragment of PhyB from *Arabidopsis thaliana*, and the PIP comprises the APB domain of PIF6; or
        (ii) the first protein construct or second protein construct can be optically detected, and the change in interaction is detected by optically detecting its spatial distribution; or
        (iii) the change in interaction can be detected within one minute of exposure to regulatory red or infra-red light; or
        (iv) a portion of the cell is exposed to regulatory red or infra-red light and the change in interaction is spatially localized within a few microns of the exposed portion.

2. The method of claim 1, wherein one of the protein constructs comprises a sub cellular localization tag (SLT), whereby the protein construct is localized to a sub cellular compartment.

3. The method of claim 2, wherein the other protein construct comprises a detectable label, whereby interaction between both protein constructs upon exposure to red light results in recruitment of the detectable label to said sub cellular compartment.

4. The method of claim 3, wherein the label can be optically detected.

5. The method of claim 1, wherein the phytochrome domain is initially converted to (i) the Pr state, thereby disallowing the interaction between the first protein construct and the second protein construct; or (ii) the Pfr state, thereby allowing the interaction between the first protein construct and the second protein construct.

6. The method of claim 5, wherein the phytochrome domain is converted to (i) the Pr state by exposing the cell to infra-red light, or (ii) the Pr state by exposing the cell to red light.

7. The method of claim 6, wherein the phytochrome domain:
    (i) if initially converted to the Pr state, is subsequently converted to the Pfr state, thereby inducing any interaction between the first protein construct and second protein construct; or
    (ii) if initially converted to the Pfr state, is subsequently converted to the Pr state, thereby discontinuing any interaction between the first protein construct and second protein construct.

8. The method of claim 7, wherein phytochrome domain is subsequently converted to the Pfr state by exposing the cell to red light, or to the Pr state by exposing the cell to infrared light.

9. The method of claim 1, wherein neither the first protein sequence nor the second protein sequence is a transcriptional regulator.

10. The method of claim 1, wherein the first protein sequence or second protein sequence is a signaling polypeptide.

11. The method of claim 1, wherein the red light has a wavelength of about 650 nm.

12. The method of claim 1, wherein the infra-red light has a wavelength of about 730 nm.

13. The method of claim 1, wherein the phytochrome domain is derived from *Arabidopsis thaliana* PhyB.

14. The method of claim 13, wherein the PHD includes the chromophore-binding domain and C-terminal tandem PAS domains of PhyB.

15. The method of claim 1, wherein the PIP is derived from the activated phytochrome B-binding domain (APB) of PIF6.

16. The method of claim 1, wherein the cell is a yeast, insect, avian or mammalian cell.

17. An isolated or recombinant cell, comprising a first and a second protein construct, and/or one or more nucleic acids encoding said first and second protein constructs, wherein:
    (a) the first protein construct comprises a first protein sequence of interest and an activated phytochrome B-binding domain (APB) of PIF6; and
    (b) the second protein construct comprises a second protein sequence of interest and a phytochrome domain from PhyB of *A. thaliana*, wherein the phytochrome domain:
        (i) can convert in a fully photo-reversible manner from a red-light absorbing conformer (Pr state) to a far-red light-absorbing conformer (Pfr state) upon exposure to red light,
        (ii) can convert in a fully photo-reversible manner from the Pfr state to the Pr state upon exposure to infra-red light, and
        (iii) lacks the kinase domain of the full-length phytochrome, and comprises the tandem C-terminal PAS domains.

18. The cell of claim 17, wherein the cell is a mammalian cell.

19. A kit comprising a first and a second protein construct, and/or one or more nucleic acids encoding said first and second protein constructs, wherein:
    (a) the first protein construct comprises a first protein sequence of interest and an activated phytochrome B-binding domain (APB) of PIF6; and
    (b) the second protein construct comprises a second protein sequence of interest and a phytochrome domain from PhyB of *A. thaliana*, wherein the phytochrome domain:
        (i) can convert in a fully photo-reversible manner from a red-light absorbing conformer (Pr state) to a far-red light-absorbing conformer (Pfr state) upon exposure to red light,
        (ii) can convert in a fully photo-reversible manner from the Pfr state to the Pr state upon exposure to infra-red light, and
        (iii) lacks the kinase domain of the full-length phytochrome, and comprises the tandem C-terminal PAS domains.

20. The kit of claim 19, further comprising a chromophore.

* * * * *

UNITED STATES PATENT AND TRADEMARK OFFICE
CERTIFICATE OF CORRECTION

PATENT NO. : 8,828,658 B2  
APPLICATION NO. : 12/993702  
DATED : September 9, 2014  
INVENTOR(S) : Christopher A. Voigt et al.

It is certified that error appears in the above-identified patent and that said Letters Patent is hereby corrected as shown below:

Column 1, Lines 12-14: Delete "Research was done with the help of Federal Grant Number NIH/PN2EY016546 and NSF Graduate Fellowship No. 2005030582. The United States Government has certain rights in the invention." and Insert --This invention was made with government support under grant no. EY016546, awarded by the National Institutes of Health. The government has certain rights in the invention.--

Signed and Sealed this  
Seventh Day of June, 2016

Michelle K. Lee  
*Director of the United States Patent and Trademark Office*

SEQUENCE LISTING

```
<160> NUMBER OF SEQ ID NOS: 19

<210> SEQ ID NO 1
<211> LENGTH: 1122
<212> TYPE: PRT
<213> ORGANISM: Arabidopsis thaliana

<400> SEQUENCE: 1

Met Ser Gly Ser Arg Pro Thr Gln Ser Ser Glu Gly Ser Arg Arg Ser
1               5                   10                  15

Arg His Ser Ala Arg Ile Ile Ala Gln Thr Thr Val Asp Ala Lys Leu
            20                  25                  30

His Ala Asp Phe Glu Glu Ser Gly Ser Ser Phe Asp Tyr Ser Thr Ser
        35                  40                  45

Val Arg Val Thr Gly Pro Val Val Glu Asn Gln Pro Pro Arg Ser Asp
    50                  55                  60

Lys Val Thr Thr Thr Tyr Leu His His Ile Gln Lys Gly Lys Leu Ile
65                  70                  75                  80

Gln Pro Phe Gly Cys Leu Leu Ala Leu Asp Glu Lys Thr Phe Lys Val
                85                  90                  95

Ile Ala Tyr Ser Glu Asn Ala Ser Glu Leu Leu Thr Met Ala Ser His
            100                 105                 110

Ala Val Pro Ser Val Gly Glu His Pro Val Leu Gly Ile Gly Thr Asp
        115                 120                 125

Ile Arg Ser Leu Phe Thr Ala Pro Ser Ala Ser Ala Leu Gln Lys Ala
    130                 135                 140

Leu Gly Phe Gly Asp Val Ser Leu Leu Asn Pro Ile Leu Val His Cys
```

```
                145                 150                 155                 160
Arg Thr Ser Ala Lys Pro Phe Tyr Ala Ile Ile His Arg Val Thr Gly
                165                 170                 175

Ser Ile Ile Ile Asp Phe Glu Pro Val Lys Pro Tyr Glu Val Pro Met
                180                 185                 190

Thr Ala Ala Gly Ala Leu Gln Ser Tyr Lys Leu Ala Ala Lys Ala Ile
                195                 200                 205

Thr Arg Leu Gln Ser Leu Pro Ser Gly Ser Met Glu Arg Leu Cys Asp
210                 215                 220

Thr Met Val Gln Glu Val Phe Glu Leu Thr Gly Tyr Asp Arg Val Met
225                 230                 235                 240

Ala Tyr Lys Phe His Glu Asp His Gly Glu Val Val Ser Glu Val
                245                 250                 255

Thr Lys Pro Gly Leu Glu Pro Tyr Leu Gly Leu His Tyr Pro Ala Thr
                260                 265                 270

Asp Ile Pro Gln Ala Ala Arg Phe Leu Phe Met Lys Asn Lys Val Arg
                275                 280                 285

Met Ile Val Asp Cys Asn Ala Lys His Ala Arg Val Leu Gln Asp Glu
                290                 295                 300

Lys Leu Ser Phe Asp Leu Thr Leu Cys Gly Ser Thr Leu Arg Ala Pro
305                 310                 315                 320

His Ser Cys His Leu Gln Tyr Met Ala Asn Met Asp Ser Ile Ala Ser
                325                 330                 335

Leu Val Met Ala Val Val Val Asn Glu Glu Asp Gly Glu Gly Asp Ala
                340                 345                 350

Pro Asp Ala Thr Thr Gln Pro Gln Lys Arg Lys Arg Leu Trp Gly Leu
                355                 360                 365

Val Val Cys His Asn Thr Thr Pro Arg Phe Val Pro Phe Pro Leu Arg
                370                 375                 380

Tyr Ala Cys Glu Phe Leu Ala Gln Val Phe Ala Ile His Val Asn Lys
385                 390                 395                 400

Glu Val Glu Leu Asp Asn Gln Met Val Glu Lys Asn Ile Leu Arg Thr
                405                 410                 415

Gln Thr Leu Leu Cys Asp Met Leu Met Arg Asp Ala Pro Leu Gly Ile
                420                 425                 430

Val Ser Gln Ser Pro Asn Ile Met Asp Leu Val Lys Cys Asp Gly Ala
                435                 440                 445

Ala Leu Leu Tyr Lys Asp Lys Ile Trp Lys Leu Gly Thr Thr Pro Ser
450                 455                 460

Glu Phe His Leu Gln Glu Ile Ala Ser Trp Leu Cys Glu Tyr His Met
465                 470                 475                 480

Asp Ser Thr Gly Leu Ser Thr Asp Ser Leu His Asp Ala Gly Phe Pro
                485                 490                 495

Arg Ala Leu Ser Leu Gly Asp Ser Val Cys Gly Met Ala Ala Val Arg
                500                 505                 510

Ile Ser Ser Lys Asp Met Ile Phe Trp Phe Arg Ser His Thr Ala Gly
                515                 520                 525

Glu Val Arg Trp Gly Gly Ala Lys His Asp Pro Asp Asp Arg Asp Asp
                530                 535                 540

Ala Arg Arg Met His Pro Arg Ser Ser Phe Lys Ala Phe Leu Glu Val
545                 550                 555                 560

Val Lys Thr Arg Ser Leu Pro Trp Lys Asp Tyr Glu Met Asp Ala Ile
                565                 570                 575
```

```
His Ser Leu Gln Leu Ile Leu Arg Asn Ala Phe Lys Asp Ser Glu Thr
            580                 585                 590

Thr Asp Val Asn Thr Lys Val Ile Tyr Ser Lys Leu Asn Asp Leu Lys
            595                 600                 605

Ile Asp Gly Ile Gln Glu Leu Glu Ala Val Thr Ser Glu Met Val Arg
610                 615                 620

Leu Ile Glu Thr Ala Thr Val Pro Ile Leu Ala Val Asp Ser Asp Gly
625                 630                 635                 640

Leu Val Asn Gly Trp Asn Thr Lys Ile Ala Glu Leu Thr Gly Leu Ser
            645                 650                 655

Val Asp Glu Ala Ile Gly Lys His Phe Leu Thr Leu Val Glu Asp Ser
            660                 665                 670

Ser Val Glu Ile Val Lys Arg Met Leu Glu Asn Ala Leu Glu Gly Thr
            675                 680                 685

Glu Glu Gln Asn Val Gln Phe Glu Ile Lys Thr His Leu Ser Arg Ala
            690                 695                 700

Asp Ala Gly Pro Ile Ser Leu Val Val Asn Ala Cys Ala Ser Arg Asp
705                 710                 715                 720

Leu His Glu Asn Val Val Gly Val Cys Phe Val Ala His Asp Leu Thr
            725                 730                 735

Gly Gln Lys Thr Val Met Asp Lys Phe Thr Arg Ile Glu Gly Asp Tyr
            740                 745                 750

Lys Ala Ile Ile Gln Asn Pro Asn Pro Leu Ile Pro Pro Ile Phe Gly
            755                 760                 765

Thr Asp Glu Phe Gly Trp Cys Thr Glu Trp Asn Pro Ala Met Ser Lys
770                 775                 780

Leu Thr Gly Leu Lys Arg Glu Glu Val Ile Asp Lys Met Leu Leu Gly
785                 790                 795                 800

Glu Val Phe Gly Thr Gln Lys Ser Cys Cys Arg Leu Lys Asn Gln Glu
            805                 810                 815

Ala Phe Val Asn Leu Gly Ile Val Leu Asn Asn Ala Val Thr Ser Gln
            820                 825                 830

Asp Pro Glu Lys Val Ser Phe Ala Phe Phe Thr Arg Gly Gly Lys Tyr
            835                 840                 845

Val Glu Cys Leu Leu Cys Val Ser Lys Lys Leu Asp Arg Glu Gly Val
            850                 855                 860

Val Thr Gly Val Phe Cys Phe Leu Gln Leu Ala Ser His Glu Leu Gln
865                 870                 875                 880

Gln Ala Leu His Val Gln Arg Leu Ala Glu Arg Thr Ala Val Lys Arg
            885                 890                 895

Leu Lys Ala Leu Ala Tyr Ile Lys Arg Gln Ile Arg Asn Pro Leu Ser
            900                 905                 910

Gly Ile Met Phe Thr Arg Lys Met Ile Glu Gly Thr Glu Leu Gly Pro
            915                 920                 925

Glu Gln Arg Arg Ile Leu Gln Thr Ser Ala Leu Cys Gln Lys Gln Leu
            930                 935                 940

Ser Lys Ile Leu Asp Asp Ser Asp Leu Glu Ser Ile Ile Glu Gly Cys
945                 950                 955                 960

Leu Asp Leu Glu Met Lys Glu Phe Thr Leu Asn Glu Val Leu Thr Ala
            965                 970                 975

Ser Thr Ser Gln Val Met Met Lys Ser Asn Gly Lys Ser Val Arg Ile
            980                 985                 990
```

```
Thr Asn Glu Thr Gly Glu Glu Val Met Ser Asp Thr Leu Tyr Gly Asp
        995                 1000                1005

Ser Ile Arg Leu Gln Gln Val Leu Ala Asp Phe Met Leu Met Ala
    1010                1015                1020

Val Asn Phe Thr Pro Ser Gly Gly Gln Leu Thr Val Ser Ala Ser
1025                1030                1035

Leu Arg Lys Asp Gln Leu Gly Arg Ser Val His Leu Ala Asn Leu
1040                1045                1050

Glu Ile Arg Leu Thr His Thr Gly Ala Gly Ile Pro Glu Phe Leu
1055                1060                1065

Leu Asn Gln Met Phe Gly Thr Glu Glu Asp Val Ser Glu Glu Gly
1070                1075                1080

Leu Ser Leu Met Val Ser Arg Lys Leu Val Lys Leu Met Asn Gly
1085                1090                1095

Asp Val Gln Tyr Leu Arg Gln Ala Gly Lys Ser Ser Phe Ile Ile
1100                1105                1110

Thr Ala Glu Leu Ala Ala Ala Asn Lys
1115                1120

<210> SEQ ID NO 2
<211> LENGTH: 1172
<212> TYPE: PRT
<213> ORGANISM: Arabidopsis thaliana

<400> SEQUENCE: 2

Met Val Ser Gly Val Gly Gly Ser Gly Gly Gly Arg Gly Gly Gly Arg
1               5                   10                  15

Gly Gly Glu Glu Glu Pro Ser Ser Ser His Thr Pro Asn Asn Arg Arg
            20                  25                  30

Gly Gly Glu Gln Ala Gln Ser Ser Gly Thr Lys Ser Leu Arg Pro Arg
        35                  40                  45

Ser Asn Thr Glu Ser Met Ser Lys Ala Ile Gln Gln Tyr Thr Val Asp
    50                  55                  60

Ala Arg Leu His Ala Val Phe Glu Gln Ser Gly Glu Ser Gly Lys Ser
65                  70                  75                  80

Phe Asp Tyr Ser Gln Ser Leu Lys Thr Thr Thr Tyr Gly Ser Ser Val
                85                  90                  95

Pro Glu Gln Gln Ile Thr Ala Tyr Leu Ser Arg Ile Gln Arg Gly Gly
            100                 105                 110

Tyr Ile Gln Pro Phe Gly Cys Met Ile Ala Val Asp Glu Ser Ser Phe
        115                 120                 125

Arg Ile Ile Gly Tyr Ser Glu Asn Ala Arg Glu Met Leu Gly Ile Met
    130                 135                 140

Pro Gln Ser Val Pro Thr Leu Glu Lys Pro Glu Ile Leu Ala Met Gly
145                 150                 155                 160

Thr Asp Val Arg Ser Leu Phe Thr Ser Ser Ser Ile Leu Leu Glu
                165                 170                 175

Arg Ala Phe Val Ala Arg Glu Ile Thr Leu Leu Asn Pro Val Trp Ile
            180                 185                 190

His Ser Lys Asn Thr Gly Lys Pro Phe Tyr Ala Ile Leu His Arg Ile
        195                 200                 205

Asp Val Gly Val Val Ile Asp Leu Glu Pro Ala Arg Thr Glu Asp Pro
    210                 215                 220

Ala Leu Ser Ile Ala Gly Ala Val Gln Ser Gln Lys Leu Ala Val Arg
225                 230                 235                 240
```

```
Ala Ile Ser Gln Leu Gln Ala Leu Pro Gly Gly Asp Ile Lys Leu Leu
            245                 250                 255

Cys Asp Thr Val Val Glu Ser Val Arg Asp Leu Thr Gly Tyr Asp Arg
            260                 265                 270

Val Met Val Tyr Lys Phe His Glu Asp Glu His Gly Glu Val Val Ala
        275                 280                 285

Glu Ser Lys Arg Asp Asp Leu Glu Pro Tyr Ile Gly Leu His Tyr Pro
    290                 295                 300

Ala Thr Asp Ile Pro Gln Ala Ser Arg Phe Leu Phe Lys Gln Asn Arg
305                 310                 315                 320

Val Arg Met Ile Val Asp Cys Asn Ala Thr Pro Val Leu Val Val Gln
                325                 330                 335

Asp Asp Arg Leu Thr Gln Ser Met Cys Leu Val Gly Ser Thr Leu Arg
            340                 345                 350

Ala Pro His Gly Cys His Ser Gln Tyr Met Ala Asn Met Gly Ser Ile
        355                 360                 365

Ala Ser Leu Ala Met Ala Val Ile Ile Asn Gly Asn Glu Asp Asp Gly
    370                 375                 380

Ser Asn Val Ala Ser Gly Arg Ser Ser Met Arg Leu Trp Gly Leu Val
385                 390                 395                 400

Val Cys His His Thr Ser Ser Arg Cys Ile Pro Phe Pro Leu Arg Tyr
                405                 410                 415

Ala Cys Glu Phe Leu Met Gln Ala Phe Gly Leu Gln Leu Asn Met Glu
            420                 425                 430

Leu Gln Leu Ala Leu Gln Met Ser Glu Lys Arg Val Leu Arg Thr Gln
        435                 440                 445

Thr Leu Leu Cys Asp Met Leu Leu Arg Asp Ser Pro Ala Gly Ile Val
450                 455                 460

Thr Gln Ser Pro Ser Ile Met Asp Leu Val Lys Cys Asp Gly Ala Ala
465                 470                 475                 480

Phe Leu Tyr His Gly Lys Tyr Tyr Pro Leu Gly Val Ala Pro Ser Glu
            485                 490                 495

Val Gln Ile Lys Asp Val Val Glu Trp Leu Leu Ala Asn His Ala Asp
            500                 505                 510

Ser Thr Gly Leu Ser Thr Asp Ser Leu Gly Asp Ala Gly Tyr Pro Gly
        515                 520                 525

Ala Ala Ala Leu Gly Asp Ala Val Cys Gly Met Ala Val Ala Tyr Ile
    530                 535                 540

Thr Lys Arg Asp Phe Leu Phe Trp Phe Arg Ser His Thr Ala Lys Glu
545                 550                 555                 560

Ile Lys Trp Gly Gly Ala Lys His His Pro Glu Asp Lys Asp Asp Gly
                565                 570                 575

Gln Arg Met His Pro Arg Ser Ser Phe Gln Ala Phe Leu Glu Val Val
            580                 585                 590

Lys Ser Arg Ser Gln Pro Trp Glu Thr Ala Glu Met Asp Ala Ile His
        595                 600                 605

Ser Leu Gln Leu Ile Leu Arg Asp Ser Phe Lys Glu Ser Glu Ala Ala
    610                 615                 620

Met Asn Ser Lys Val Val Asp Gly Val Val Gln Pro Cys Arg Asp Met
625                 630                 635                 640

Ala Gly Glu Gln Gly Ile Asp Glu Leu Gly Ala Val Ala Arg Glu Met
            645                 650                 655
```

-continued

```
Val Arg Leu Ile Glu Thr Ala Thr Val Pro Ile Phe Ala Val Asp Ala
        660                 665                 670

Gly Gly Cys Ile Asn Gly Trp Asn Ala Lys Ile Ala Glu Leu Thr Gly
        675                 680                 685

Leu Ser Val Glu Glu Ala Met Gly Lys Ser Leu Val Ser Asp Leu Ile
    690                 695                 700

Tyr Lys Glu Asn Glu Ala Thr Val Asn Lys Leu Leu Ser Arg Ala Leu
705                 710                 715                 720

Arg Gly Asp Glu Glu Lys Asn Val Glu Val Lys Leu Lys Thr Phe Ser
                725                 730                 735

Pro Glu Leu Gln Gly Lys Ala Val Phe Val Val Asn Ala Cys Ser
            740                 745                 750

Ser Lys Asp Tyr Leu Asn Asn Ile Val Gly Val Cys Phe Val Gly Gln
        755                 760                 765

Asp Val Thr Ser Gln Lys Ile Val Met Asp Lys Phe Ile Asn Ile Gln
        770                 775                 780

Gly Asp Tyr Lys Ala Ile Val His Ser Pro Asn Pro Leu Ile Pro Pro
785                 790                 795                 800

Ile Phe Ala Ala Asp Glu Asn Thr Cys Cys Leu Glu Trp Asn Met Ala
                805                 810                 815

Met Glu Lys Leu Thr Gly Trp Ser Arg Ser Glu Val Ile Gly Lys Met
            820                 825                 830

Ile Val Gly Glu Val Phe Gly Ser Cys Cys Met Leu Lys Gly Pro Asp
        835                 840                 845

Ala Leu Thr Lys Phe Met Ile Val Leu His Asn Ala Ile Gly Gly Gln
    850                 855                 860

Asp Thr Asp Lys Phe Pro Phe Pro Phe Phe Asp Arg Asn Gly Lys Phe
865                 870                 875                 880

Val Gln Ala Leu Leu Thr Ala Asn Lys Arg Val Ser Leu Glu Gly Lys
                885                 890                 895

Val Ile Gly Ala Phe Cys Phe Leu Gln Ile Pro Ser Pro Glu Leu Gln
            900                 905                 910

Gln Ala Leu Ala Val Gln Arg Arg Gln Asp Thr Glu Cys Phe Thr Lys
        915                 920                 925

Ala Lys Glu Leu Ala Tyr Ile Cys Gln Val Ile Lys Asn Pro Leu Ser
    930                 935                 940

Gly Met Arg Phe Ala Asn Ser Leu Leu Glu Ala Thr Asp Leu Asn Glu
945                 950                 955                 960

Asp Gln Lys Gln Leu Leu Glu Thr Ser Val Ser Cys Glu Lys Gln Ile
                965                 970                 975

Ser Arg Ile Val Gly Asp Met Asp Leu Glu Ser Ile Glu Asp Gly Ser
            980                 985                 990

Phe Val Leu Lys Arg Glu Glu Phe  Phe Leu Gly Ser Val  Ile Asn Ala
        995                 1000                1005

Ile Val  Ser Gln Ala Met Phe  Leu Leu Arg Asp Arg  Gly Leu Gln
    1010                 1015                1020

Leu Ile  Arg Asp Ile Pro Glu  Glu Ile Lys Ser Ile  Glu Val Phe
1025                 1030                1035

Gly Asp  Gln Ile Arg Ile Gln  Gln Leu Leu Ala Glu  Phe Leu Leu
1040                 1045                1050

Ser Ile  Ile Arg Tyr Ala Pro  Ser Gln Glu Trp Val  Glu Ile His
1055                 1060                1065

Leu Ser  Gln Leu Ser Lys Gln  Met Ala Asp Gly Phe  Ala Ala Ile
```

```
                      1070              1075                1080
Arg Thr Glu Phe Arg Met Ala Cys Pro Gly Glu Gly Leu Pro Pro
1085                1090                1095

Glu Leu Val Arg Asp Met Phe His Ser Ser Arg Trp Thr Ser Pro
1100                1105                1110

Glu Gly Leu Gly Leu Ser Val Cys Arg Lys Ile Leu Lys Leu Met
1115                1120                1125

Asn Gly Glu Val Gln Tyr Ile Arg Glu Ser Glu Arg Ser Tyr Phe
1130                1135                1140

Leu Ile Ile Leu Glu Leu Pro Val Pro Arg Lys Arg Pro Leu Ser
1145                1150                1155

Thr Ala Ser Gly Ser Gly Asp Met Met Leu Met Met Pro Tyr
1160                1165                1170

<210> SEQ ID NO 3
<211> LENGTH: 1111
<212> TYPE: PRT
<213> ORGANISM: Arabidopsis thaliana

<400> SEQUENCE: 3

Met Ser Ser Asn Thr Ser Arg Ser Cys Ser Thr Arg Ser Arg Gln Asn
1               5                   10                  15

Ser Arg Val Ser Ser Gln Val Leu Val Asp Ala Lys Leu His Gly Asn
                20                  25                  30

Phe Glu Glu Ser Glu Arg Leu Phe Asp Tyr Ser Ala Ser Ile Asn Leu
            35                  40                  45

Asn Met Pro Ser Ser Ser Cys Glu Ile Pro Ser Ser Ala Val Ser Thr
        50                  55                  60

Tyr Leu Gln Lys Ile Gln Arg Gly Met Leu Ile Gln Pro Phe Gly Cys
65                  70                  75                  80

Leu Ile Val Val Asp Glu Lys Asn Leu Lys Val Ile Ala Phe Ser Glu
                85                  90                  95

Asn Thr Gln Glu Met Leu Gly Leu Ile Pro His Thr Val Pro Ser Met
            100                 105                 110

Glu Gln Arg Glu Ala Leu Thr Ile Gly Thr Asp Val Lys Ser Leu Phe
        115                 120                 125

Leu Ser Pro Gly Cys Ser Ala Leu Glu Lys Ala Val Asp Phe Gly Glu
    130                 135                 140

Ile Ser Ile Leu Asn Pro Ile Thr Leu His Cys Arg Ser Ser Ser Lys
145                 150                 155                 160

Pro Phe Tyr Ala Ile Leu His Arg Ile Glu Glu Gly Leu Val Ile Asp
                165                 170                 175

Leu Glu Pro Val Ser Pro Asp Glu Val Pro Val Thr Ala Ala Gly Ala
            180                 185                 190

Leu Arg Ser Tyr Lys Leu Ala Ala Lys Ser Ile Ser Arg Leu Gln Ala
        195                 200                 205

Leu Pro Ser Gly Asn Met Leu Leu Cys Asp Ala Leu Val Lys Glu
    210                 215                 220

Val Ser Glu Leu Thr Gly Tyr Asp Arg Val Met Val Tyr Lys Phe His
225                 230                 235                 240

Glu Asp Gly His Gly Glu Val Ile Ala Glu Cys Cys Arg Glu Asp Met
                245                 250                 255

Glu Pro Tyr Leu Gly Leu His Tyr Ser Ala Thr Asp Ile Pro Gln Ala
            260                 265                 270
```

-continued

```
Ser Arg Phe Leu Phe Met Arg Asn Lys Val Arg Met Ile Cys Asp Cys
            275                 280                 285
Ser Ala Val Pro Val Lys Val Val Gln Asp Lys Ser Leu Ser Gln Pro
290                 295                 300
Ile Ser Leu Ser Gly Ser Thr Leu Arg Ala Pro His Gly Cys His Ala
305                 310                 315                 320
Gln Tyr Met Ser Asn Met Gly Ser Val Ala Ser Leu Val Met Ser Val
                325                 330                 335
Thr Ile Asn Gly Ser Asp Ser Asp Glu Met Asn Arg Asp Leu Gln Thr
                340                 345                 350
Gly Arg His Leu Trp Gly Leu Val Val Cys His His Ala Ser Pro Arg
            355                 360                 365
Phe Val Pro Phe Pro Leu Arg Tyr Ala Cys Glu Phe Leu Thr Gln Val
370                 375                 380
Phe Gly Val Gln Ile Asn Lys Glu Ala Glu Ser Ala Val Leu Leu Lys
385                 390                 395                 400
Glu Lys Arg Ile Leu Gln Thr Gln Ser Val Leu Cys Asp Met Leu Phe
                405                 410                 415
Arg Asn Ala Pro Ile Gly Ile Val Thr Gln Ser Pro Asn Ile Met Asp
            420                 425                 430
Leu Val Lys Cys Asp Gly Ala Ala Leu Tyr Tyr Arg Asp Asn Leu Trp
            435                 440                 445
Ser Leu Gly Val Thr Pro Thr Glu Thr Gln Ile Arg Asp Leu Ile Asp
            450                 455                 460
Trp Val Leu Lys Ser His Gly Gly Asn Thr Gly Phe Thr Thr Glu Ser
465                 470                 475                 480
Leu Met Glu Ser Gly Tyr Pro Asp Ala Ser Val Leu Gly Glu Ser Ile
                485                 490                 495
Cys Gly Met Ala Ala Val Tyr Ile Ser Glu Lys Asp Phe Leu Phe Trp
            500                 505                 510
Phe Arg Ser Ser Thr Ala Lys Gln Ile Lys Trp Gly Gly Ala Arg His
            515                 520                 525
Asp Pro Asn Asp Arg Asp Gly Lys Arg Met His Pro Arg Ser Ser Phe
530                 535                 540
Lys Ala Phe Met Glu Ile Val Arg Trp Lys Ser Val Pro Trp Asp Asp
545                 550                 555                 560
Met Glu Met Asp Ala Ile Asn Ser Leu Gln Leu Ile Leu Lys Gly Ser
                565                 570                 575
Leu Gln Glu Glu His Ser Lys Thr Val Val Asp Val Pro Leu Val Asp
            580                 585                 590
Asn Arg Val Gln Lys Val Asp Glu Leu Cys Val Ile Val Asn Glu Met
            595                 600                 605
Val Arg Leu Ile Asp Thr Ala Ala Val Pro Ile Phe Ala Val Asp Ala
            610                 615                 620
Ser Gly Val Ile Asn Gly Trp Asn Ser Lys Ala Ala Glu Val Thr Gly
625                 630                 635                 640
Leu Ala Val Glu Gln Ala Ile Gly Lys Pro Val Ser Asp Leu Val Glu
                645                 650                 655
Asp Asp Ser Val Glu Thr Val Lys Asn Met Leu Ala Leu Ala Leu Glu
            660                 665                 670
Gly Ser Glu Glu Arg Gly Ala Glu Ile Arg Ile Arg Ala Phe Gly Pro
            675                 680                 685
Lys Arg Lys Ser Ser Pro Val Glu Leu Val Val Asn Thr Cys Cys Ser
```

```
                    690                 695                 700
Arg Asp Met Thr Asn Asn Val Leu Gly Val Cys Phe Ile Gly Gln Asp
705                 710                 715                 720

Val Thr Gly Gln Lys Thr Leu Thr Glu Asn Tyr Ser Arg Val Lys Gly
                725                 730                 735

Asp Tyr Ala Arg Ile Met Trp Ser Pro Ser Thr Leu Ile Pro Pro Ile
                740                 745                 750

Phe Ile Thr Asn Glu Asn Gly Val Cys Ser Glu Trp Asn Asn Ala Met
                755                 760                 765

Gln Lys Leu Ser Gly Ile Lys Arg Glu Glu Val Val Asn Lys Ile Leu
                770                 775                 780

Leu Gly Glu Val Phe Thr Thr Asp Tyr Gly Cys Cys Leu Lys Asp
785                 790                 795                 800

His Asp Thr Leu Thr Lys Leu Arg Ile Gly Phe Asn Ala Val Ile Ser
                805                 810                 815

Gly Gln Lys Asn Ile Glu Lys Leu Leu Phe Gly Phe Tyr His Arg Asp
                820                 825                 830

Gly Ser Phe Ile Glu Ala Leu Leu Ser Ala Asn Lys Arg Thr Asp Ile
                835                 840                 845

Glu Gly Lys Val Thr Gly Val Leu Cys Phe Leu Gln Val Pro Ser Pro
                850                 855                 860

Glu Leu Gln Tyr Ala Leu Gln Val Gln Gln Ile Ser Glu His Ala Ile
865                 870                 875                 880

Ala Cys Ala Leu Asn Lys Leu Ala Tyr Leu Arg His Glu Val Lys Asp
                885                 890                 895

Pro Glu Lys Ala Ile Ser Phe Leu Gln Asp Leu Leu His Ser Ser Gly
                900                 905                 910

Leu Ser Glu Asp Gln Lys Arg Leu Leu Arg Thr Ser Val Leu Cys Arg
                915                 920                 925

Glu Gln Leu Ala Lys Val Ile Ser Asp Ser Asp Ile Glu Gly Ile Glu
                930                 935                 940

Glu Gly Tyr Val Glu Leu Asp Cys Ser Glu Phe Gly Leu Gln Glu Ser
945                 950                 955                 960

Leu Glu Ala Val Val Lys Gln Val Met Glu Leu Ser Ile Glu Arg Lys
                965                 970                 975

Val Gln Ile Ser Cys Asp Tyr Pro Gln Glu Val Ser Ser Met Arg Leu
                980                 985                 990

Tyr Gly Asp Asn Leu Arg Leu Gln  Gln Ile Leu Ser Glu  Thr Leu Leu
                995                 1000                1005

Ser Ser  Ile Arg Phe Thr Pro  Ala Leu Arg Gly Leu  Cys Val Ser
    1010                1015                1020

Phe Lys  Val Ile Ala Arg Ile  Glu Ala Ile Gly Lys  Arg Met Lys
1025                1030                1035

Arg Val  Glu Leu Glu Phe Arg  Ile Ile His Pro Ala  Pro Gly Leu
1040                1045                1050

Pro Glu  Asp Leu Val Arg Glu  Met Phe Gln Pro Leu  Arg Lys Gly
1055                1060                1065

Thr Ser  Arg Glu Gly Leu Gly  Leu His Ile Thr Gln  Lys Leu Val
1070                1075                1080

Lys Leu  Met Glu Arg Gly Thr  Leu Arg Tyr Leu Arg  Glu Ser Glu
1085                1090                1095

Met Ser  Ala Phe Val Ile Leu  Thr Glu Phe Pro Leu  Ile
1100                1105                1110
```

<210> SEQ ID NO 4
<211> LENGTH: 1164
<212> TYPE: PRT
<213> ORGANISM: Arabidopsis thaliana

<400> SEQUENCE: 4

```
Met Val Ser Gly Gly Ser Lys Thr Ser Gly Glu Ala Ala Ser
1               5                   10                  15

Ser Gly His Arg Arg Ser Arg His Thr Ser Ala Ala Glu Gln Ala Gln
                20                  25                  30

Ser Ser Ala Asn Lys Ala Leu Arg Ser Gln Asn Gln Gln Pro Gln Asn
            35                  40                  45

His Gly Gly Gly Thr Glu Ser Thr Asn Lys Ala Ile Gln Gln Tyr Thr
        50                  55                  60

Val Asp Ala Arg Leu His Ala Val Phe Glu Gln Ser Gly Glu Ser Gly
65                  70                  75                  80

Lys Ser Phe Asp Tyr Ser Gln Ser Leu Lys Thr Ala Pro Tyr Asp Ser
                85                  90                  95

Ser Val Pro Glu Gln Gln Ile Thr Ala Tyr Leu Ser Arg Ile Gln Arg
            100                 105                 110

Gly Gly Tyr Thr Gln Pro Phe Gly Cys Leu Ile Ala Val Glu Glu Ser
        115                 120                 125

Thr Phe Thr Ile Ile Gly Tyr Ser Glu Asn Ala Arg Glu Met Leu Gly
    130                 135                 140

Leu Met Ser Gln Ser Val Pro Ser Ile Glu Asp Lys Ser Glu Val Leu
145                 150                 155                 160

Thr Ile Gly Thr Asp Leu Arg Ser Leu Phe Lys Ser Ser Ser Tyr Leu
                165                 170                 175

Leu Leu Glu Arg Ala Phe Val Ala Arg Glu Ile Thr Leu Leu Asn Pro
            180                 185                 190

Ile Trp Ile His Ser Asn Asn Thr Gly Lys Pro Phe Tyr Ala Ile Leu
        195                 200                 205

His Arg Val Asp Val Gly Ile Leu Ile Asp Leu Glu Pro Ala Arg Thr
    210                 215                 220

Glu Asp Pro Ala Leu Ser Ile Ala Gly Ala Val Gln Ser Gln Lys Leu
225                 230                 235                 240

Ala Val Arg Ala Ile Ser His Leu Gln Ser Leu Pro Ser Gly Asp Ile
                245                 250                 255

Lys Leu Leu Cys Asp Thr Val Val Glu Ser Val Arg Asp Leu Thr Gly
            260                 265                 270

Tyr Asp Arg Val Met Val Tyr Lys Phe His Glu Asp Glu His Gly Glu
        275                 280                 285

Val Val Ala Glu Ser Lys Arg Asn Asp Leu Glu Pro Tyr Ile Gly Leu
    290                 295                 300

His Tyr Pro Ala Thr Asp Ile Pro Gln Ala Ser Arg Phe Leu Phe Lys
305                 310                 315                 320

Gln Asn Arg Val Arg Met Ile Val Asp Cys Tyr Ala Ser Pro Val Arg
                325                 330                 335

Val Val Gln Asp Asp Arg Leu Thr Gln Phe Ile Cys Leu Val Gly Ser
            340                 345                 350

Thr Leu Arg Ala Pro His Gly Cys His Ala Gln Tyr Met Thr Asn Met
        355                 360                 365

Gly Ser Ile Ala Ser Leu Ala Met Ala Val Ile Ile Asn Gly Asn Glu
```

```
            370                 375                 380
Glu Asp Gly Asn Gly Val Asn Thr Gly Gly Arg Asn Ser Met Arg Leu
385                 390                 395                 400

Trp Gly Leu Val Val Cys His His Thr Ser Ala Arg Cys Ile Pro Phe
                405                 410                 415

Pro Leu Arg Tyr Ala Cys Glu Phe Leu Met Gln Ala Phe Gly Leu Gln
            420                 425                 430

Leu Asn Met Glu Leu Gln Leu Ala Leu Gln Val Ser Glu Lys Arg Val
            435                 440                 445

Leu Arg Met Gln Thr Leu Leu Cys Asp Met Leu Leu Arg Asp Ser Pro
450                 455                 460

Ala Gly Ile Val Thr Gln Arg Pro Ser Ile Met Asp Leu Val Lys Cys
465                 470                 475                 480

Asn Gly Ala Ala Phe Leu Tyr Gln Gly Lys Tyr Tyr Pro Leu Gly Val
                485                 490                 495

Thr Pro Thr Asp Ser Gln Ile Asn Asp Ile Val Glu Trp Leu Val Ala
            500                 505                 510

Asn His Ser Asp Ser Thr Gly Leu Ser Thr Asp Ser Leu Gly Asp Ala
            515                 520                 525

Gly Tyr Pro Arg Ala Ala Leu Gly Asp Ala Val Cys Gly Met Ala
            530                 535                 540

Val Ala Cys Ile Thr Lys Arg Asp Phe Leu Phe Trp Phe Arg Ser His
545                 550                 555                 560

Thr Glu Lys Glu Ile Lys Trp Gly Gly Ala Lys His His Pro Glu Asp
                565                 570                 575

Lys Asp Asp Gly Gln Arg Met Asn Pro Arg Ser Ser Phe Gln Thr Phe
            580                 585                 590

Leu Glu Val Val Lys Ser Arg Cys Gln Pro Trp Glu Thr Ala Glu Met
            595                 600                 605

Asp Ala Ile His Ser Leu Gln Leu Ile Leu Arg Asp Ser Phe Lys Glu
610                 615                 620

Ser Glu Ala Met Asp Ser Lys Ala Ala Ala Gly Ala Val Gln Pro
625                 630                 635                 640

His Gly Asp Asp Met Val Gln Gln Gly Met Gln Glu Ile Gly Ala Val
                645                 650                 655

Ala Arg Glu Met Val Arg Leu Ile Glu Thr Ala Thr Val Pro Ile Phe
            660                 665                 670

Ala Val Asp Ile Asp Gly Cys Ile Asn Gly Trp Asn Ala Lys Ile Ala
            675                 680                 685

Glu Leu Thr Gly Leu Ser Val Glu Asp Ala Met Gly Lys Ser Leu Val
690                 695                 700

Arg Glu Leu Ile Tyr Lys Glu Tyr Lys Glu Thr Val Asp Arg Leu Leu
705                 710                 715                 720

Ser Cys Ala Leu Lys Gly Asp Glu Gly Lys Asn Val Glu Val Lys Leu
                725                 730                 735

Lys Thr Phe Gly Ser Glu Leu Gln Gly Lys Ala Met Phe Val Val Val
            740                 745                 750

Asn Ala Cys Ser Ser Lys Asp Tyr Leu Asn Asn Ile Val Gly Val Cys
            755                 760                 765

Phe Val Gly Gln Asp Val Thr Gly His Lys Ile Val Met Asp Lys Phe
770                 775                 780

Ile Asn Ile Gln Gly Asp Tyr Lys Ala Ile Ile His Ser Pro Asn Pro
785                 790                 795                 800
```

Leu Ile Pro Pro Ile Phe Ala Ala Asp Glu Asn Thr Cys Cys Leu Glu
            805                 810                 815

Trp Asn Thr Ala Met Glu Lys Leu Thr Gly Trp Pro Arg Ser Glu Val
            820                 825                 830

Ile Gly Lys Leu Leu Val Arg Glu Val Phe Gly Ser Tyr Cys Arg Leu
            835                 840                 845

Lys Gly Pro Asp Ala Leu Thr Lys Phe Met Ile Val Leu His Asn Ala
        850                 855                 860

Ile Gly Gly Gln Asp Thr Asp Lys Phe Pro Phe Pro Phe Phe Asp Arg
865                 870                 875                 880

Lys Gly Glu Phe Ile Gln Ala Leu Leu Thr Leu Asn Lys Arg Val Ser
            885                 890                 895

Ile Asp Gly Lys Ile Ile Gly Ala Phe Cys Phe Leu Gln Ile Pro Ser
            900                 905                 910

Pro Glu Leu Gln Gln Ala Leu Glu Val Gln Arg Arg Gln Glu Ser Glu
            915                 920                 925

Tyr Phe Ser Arg Arg Lys Glu Leu Ala Tyr Ile Phe Gln Val Ile Lys
            930                 935                 940

Asn Pro Leu Ser Gly Leu Arg Phe Thr Asn Ser Leu Leu Glu Asp Met
945                 950                 955                 960

Asp Leu Asn Glu Asp Gln Lys Gln Leu Leu Glu Thr Ser Val Ser Cys
            965                 970                 975

Glu Lys Gln Ile Ser Lys Ile Val Gly Asp Met Asp Val Lys Ser Ile
            980                 985                 990

Asp Asp Gly Ser Phe Leu Leu Glu Arg Thr Glu Phe Phe Ile Gly Asn
            995                 1000                1005

Val Thr Asn Ala Val Val Ser Gln Val Met Leu Val Val Arg Glu
    1010                1015                1020

Arg Asn Leu Gln Leu Ile Arg Asn Ile Pro Thr Glu Val Lys Ser
1025                1030                1035

Met Ala Val Tyr Gly Asp Gln Ile Arg Leu Gln Gln Val Leu Ala
1040                1045                1050

Glu Phe Leu Leu Ser Ile Val Arg Tyr Ala Pro Met Glu Gly Ser
1055                1060                1065

Val Glu Leu His Leu Cys Pro Thr Leu Asn Gln Met Ala Asp Gly
1070                1075                1080

Phe Ser Ala Val Arg Leu Glu Phe Arg Met Ala Cys Ala Gly Glu
1085                1090                1095

Gly Val Pro Pro Glu Lys Val Gln Asp Met Phe His Ser Ser Arg
1100                1105                1110

Trp Thr Ser Pro Glu Gly Leu Gly Leu Ser Val Cys Arg Lys Ile
1115                1120                1125

Leu Lys Leu Met Asn Gly Gly Val Gln Tyr Ile Arg Glu Phe Glu
1130                1135                1140

Arg Ser Tyr Phe Leu Ile Val Ile Glu Leu Pro Val Pro Leu Met
1145                1150                1155

Met Met Met Pro Ser Ser
1160

<210> SEQ ID NO 5
<211> LENGTH: 1112
<212> TYPE: PRT
<213> ORGANISM: Arabidopsis thaliana

```
<400> SEQUENCE: 5

Met Gly Phe Glu Ser Ser Ser Ala Ala Ser Asn Met Lys Pro Gln
1               5                   10                  15

Pro Gln Lys Ser Asn Thr Ala Gln Tyr Ser Val Asp Ala Ala Leu Phe
            20                  25                  30

Ala Asp Phe Ala Gln Ser Ile Tyr Thr Gly Lys Ser Phe Asn Tyr Ser
                35                  40                  45

Lys Ser Val Ile Ser Pro Pro Asn His Val Pro Asp Glu His Ile Thr
            50                  55                  60

Ala Tyr Leu Ser Asn Ile Gln Arg Gly Gly Leu Val Gln Pro Phe Gly
65                  70                  75                  80

Cys Leu Ile Ala Val Glu Glu Pro Ser Phe Arg Ile Leu Gly Leu Ser
                85                  90                  95

Asp Asn Ser Ser Asp Phe Leu Gly Leu Leu Ser Leu Pro Ser Thr Ser
            100                 105                 110

His Ser Gly Glu Phe Asp Lys Val Lys Gly Leu Ile Gly Ile Asp Ala
                115                 120                 125

Arg Thr Leu Phe Thr Pro Ser Ser Gly Ala Ser Leu Ser Lys Ala Ala
            130                 135                 140

Ser Phe Thr Glu Ile Ser Leu Leu Asn Pro Val Leu His Ser Arg
145                 150                 155                 160

Thr Thr Gln Lys Pro Phe Tyr Ala Ile Leu His Arg Ile Asp Ala Gly
                165                 170                 175

Ile Val Met Asp Leu Glu Pro Ala Lys Ser Gly Asp Pro Ala Leu Thr
            180                 185                 190

Leu Ala Gly Ala Val Gln Ser Gln Lys Leu Ala Val Arg Ala Ile Ser
            195                 200                 205

Arg Leu Gln Ser Leu Pro Gly Gly Asp Ile Gly Ala Leu Cys Asp Thr
210                 215                 220

Val Val Glu Asp Val Gln Arg Leu Thr Gly Tyr Asp Arg Val Met Val
225                 230                 235                 240

Tyr Gln Phe His Glu Asp His Gly Glu Val Val Ser Glu Ile Arg
                245                 250                 255

Arg Ser Asp Leu Glu Pro Tyr Leu Gly Leu His Tyr Pro Ala Thr Asp
            260                 265                 270

Ile Pro Gln Ala Ala Arg Phe Leu Phe Lys Gln Asn Arg Val Arg Met
            275                 280                 285

Ile Cys Asp Cys Asn Ala Thr Pro Val Lys Val Gln Ser Glu Glu
            290                 295                 300

Leu Lys Arg Pro Leu Cys Leu Val Asn Ser Thr Leu Arg Ala Pro His
305                 310                 315                 320

Gly Cys His Thr Gln Tyr Met Ala Asn Met Gly Ser Val Ala Ser Leu
                325                 330                 335

Ala Leu Ala Ile Val Val Lys Gly Lys Asp Ser Ser Lys Leu Trp Gly
            340                 345                 350

Leu Val Val Gly His His Cys Ser Pro Arg Tyr Val Pro Phe Pro Leu
            355                 360                 365

Arg Tyr Ala Cys Glu Phe Leu Met Gln Ala Phe Gly Leu Gln Leu Gln
            370                 375                 380

Met Glu Leu Gln Leu Ala Ser Gln Leu Ala Glu Lys Lys Ala Met Arg
385                 390                 395                 400

Thr Gln Thr Leu Leu Cys Asp Met Leu Leu Arg Asp Thr Val Ser Ala
                405                 410                 415
```

```
Ile Val Thr Gln Ser Pro Gly Ile Met Asp Leu Val Lys Cys Asp Gly
            420                 425                 430

Ala Ala Leu Tyr Tyr Lys Gly Lys Cys Trp Leu Val Gly Val Thr Pro
            435                 440                 445

Asn Glu Ser Gln Val Lys Asp Leu Val Asn Trp Leu Val Glu Asn His
            450                 455                 460

Gly Asp Asp Ser Thr Gly Leu Thr Thr Asp Ser Leu Val Asp Ala Gly
465                 470                 475                 480

Tyr Pro Gly Ala Ile Ser Leu Gly Asp Ala Val Cys Gly Val Ala Ala
                485                 490                 495

Ala Glu Phe Ser Ser Lys Asp Tyr Leu Leu Trp Phe Arg Ser Asn Thr
            500                 505                 510

Ala Ser Ala Ile Lys Trp Gly Ala Lys His His Pro Lys Asp Lys
            515                 520                 525

Asp Asp Ala Gly Arg Met His Pro Arg Ser Ser Phe Thr Ala Phe Leu
            530                 535                 540

Glu Val Ala Lys Ser Arg Ser Leu Pro Trp Glu Ile Ser Glu Ile Asp
545                 550                 555                 560

Ala Ile His Ser Leu Arg Leu Ile Met Arg Glu Ser Phe Thr Ser Ser
            565                 570                 575

Arg Pro Val Leu Ser Gly Asn Gly Val Ala Arg Asp Ala Asn Glu Leu
            580                 585                 590

Thr Ser Phe Val Cys Glu Met Val Arg Val Ile Glu Thr Ala Thr Ala
            595                 600                 605

Pro Ile Phe Gly Val Asp Ser Ser Gly Cys Ile Asn Gly Trp Asn Lys
            610                 615                 620

Lys Thr Ala Glu Met Thr Gly Leu Leu Ala Ser Glu Ala Met Gly Lys
625                 630                 635                 640

Ser Leu Ala Asp Glu Ile Val Gln Glu Ser Arg Ala Ala Leu Glu
                645                 650                 655

Ser Leu Leu Cys Lys Ala Leu Gln Gly Glu Glu Lys Ser Val Met
            660                 665                 670

Leu Lys Leu Arg Lys Phe Gly Gln Asn Asn His Pro Asp Tyr Ser Ser
            675                 680                 685

Asp Val Cys Val Leu Val Asn Ser Cys Thr Ser Arg Asp Tyr Thr Glu
            690                 695                 700

Asn Ile Ile Gly Val Cys Phe Val Gly Gln Asp Ile Thr Ser Glu Lys
705                 710                 715                 720

Ala Ile Thr Asp Arg Phe Ile Arg Leu Gln Gly Asp Tyr Lys Thr Ile
                725                 730                 735

Val Gln Ser Leu Asn Pro Leu Ile Pro Pro Ile Phe Ala Ser Asp Glu
            740                 745                 750

Asn Ala Cys Cys Ser Glu Trp Asn Ala Ala Met Glu Lys Leu Thr Gly
            755                 760                 765

Trp Ser Lys His Glu Val Ile Gly Lys Met Leu Pro Gly Glu Val Phe
            770                 775                 780

Gly Val Phe Cys Lys Val Lys Cys Gln Asp Ser Leu Thr Lys Phe Leu
785                 790                 795                 800

Ile Ser Leu Tyr Gln Gly Ile Ala Gly Asp Asn Val Pro Glu Ser Ser
                805                 810                 815

Leu Val Glu Phe Phe Asn Lys Gly Lys Tyr Ile Glu Ala Ser Leu
            820                 825                 830
```

```
Thr Ala Asn Lys Ser Thr Asn Ile Glu Gly Lys Val Ile Arg Cys Phe
            835                 840                 845

Phe Phe Leu Gln Ile Ile Asn Lys Glu Ser Gly Leu Ser Cys Pro Glu
    850                 855                 860

Leu Lys Glu Ser Ala Gln Ser Leu Asn Glu Leu Thr Tyr Val Arg Gln
865                 870                 875                 880

Glu Ile Lys Asn Pro Leu Asn Gly Ile Arg Phe Ala His Lys Leu Leu
                885                 890                 895

Glu Ser Ser Glu Ile Ser Ala Ser Gln Arg Gln Phe Leu Glu Thr Ser
            900                 905                 910

Asp Ala Cys Glu Lys Gln Ile Thr Thr Ile Ile Glu Ser Thr Asp Leu
            915                 920                 925

Lys Ser Ile Glu Glu Gly Lys Leu Gln Leu Glu Thr Glu Glu Phe Arg
    930                 935                 940

Leu Glu Asn Ile Leu Asp Thr Ile Ile Ser Gln Val Met Ile Ile Leu
945                 950                 955                 960

Arg Glu Arg Asn Ser Gln Leu Arg Val Glu Val Ala Glu Glu Ile Lys
                965                 970                 975

Thr Leu Pro Leu Asn Gly Asp Arg Val Lys Leu Gln Leu Ile Leu Ala
            980                 985                 990

Asp Leu Leu Arg Asn Ile Val Asn His Ala Pro Phe Pro Asn Ser Trp
            995                 1000                1005

Val Gly Ile Ser Ile Ser Pro Gly Gln Glu Leu Ser Arg Asp Asn
    1010                1015                1020

Gly Arg Tyr Ile His Leu Gln Phe Arg Met Ile His Pro Gly Lys
1025                1030                1035

Gly Leu Pro Ser Glu Met Leu Ser Asp Met Phe Glu Thr Arg Asp
1040                1045                1050

Gly Trp Val Thr Pro Asp Gly Leu Gly Leu Lys Leu Ser Arg Lys
1055                1060                1065

Leu Leu Glu Gln Met Asn Gly Arg Val Ser Tyr Val Arg Glu Asp
1070                1075                1080

Glu Arg Cys Phe Phe Gln Val Asp Leu Gln Val Lys Thr Met Leu
1085                1090                1095

Gly Val Glu Ser Arg Gly Thr Glu Gly Ser Ser Ser Ile Lys
1100                1105                1110

<210> SEQ ID NO 6
<211> LENGTH: 524
<212> TYPE: PRT
<213> ORGANISM: Arabidopsis thaliana

<400> SEQUENCE: 6

Met Pro Leu Phe Glu Leu Phe Arg Leu Thr Lys Ala Lys Leu Glu Ser
1               5                   10                  15

Ala Gln Asp Arg Asn Pro Ser Pro Val Asp Glu Val Val Glu Leu
            20                  25                  30

Val Trp Glu Asn Gly Gln Ile Ser Thr Gln Ser Gln Ser Ser Arg Ser
        35                  40                  45

Arg Asn Ile Pro Pro Gln Ala Asn Ser Ser Arg Ala Arg Glu Ile
    50                  55                  60

Gly Asn Gly Ser Lys Thr Thr Met Val Asp Glu Ile Pro Met Ser Val
65                  70                  75                  80

Pro Ser Leu Met Thr Gly Leu Ser Gln Asp Asp Phe Val Pro Trp
                85                  90                  95
```

Leu Asn His His Pro Ser Leu Asp Gly Tyr Cys Ser Asp Phe Leu Arg
            100                 105                 110

Asp Val Ser Ser Pro Val Thr Val Asn Glu Gln Glu Ser Asp Met Ala
            115                 120                 125

Val Asn Gln Thr Ala Phe Pro Leu Phe Gln Arg Arg Lys Asp Gly Asn
            130                 135                 140

Glu Ser Ala Pro Ala Ala Ser Ser Ser Gln Tyr Asn Gly Phe Gln Ser
145                 150                 155                 160

His Ser Leu Tyr Gly Ser Asp Arg Ala Arg Asp Leu Pro Ser Gln Gln
            165                 170                 175

Thr Asn Pro Asp Arg Phe Thr Gln Thr Gln Glu Pro Leu Ile Thr Ser
            180                 185                 190

Asn Lys Pro Ser Leu Val Asn Phe Ser His Phe Leu Arg Pro Ala Thr
            195                 200                 205

Phe Ala Lys Thr Thr Asn Asn Asn Leu His Asp Thr Lys Glu Lys Ser
            210                 215                 220

Pro Gln Ser Pro Pro Asn Val Phe Gln Thr Arg Val Leu Gly Ala Lys
225                 230                 235                 240

Asp Ser Glu Asp Lys Val Leu Asn Glu Ser Val Ala Ser Ala Thr Pro
            245                 250                 255

Lys Asp Asn Gln Lys Ala Cys Leu Ile Ser Glu Asp Ser Cys Arg Lys
            260                 265                 270

Asp Gln Glu Ser Glu Lys Ala Val Val Cys Ser Ser Val Gly Ser Gly
            275                 280                 285

Asn Ser Leu Asp Gly Pro Ser Glu Ser Pro Ser Leu Ser Leu Lys Arg
            290                 295                 300

Lys His Ser Asn Ile Gln Asp Ile Asp Cys His Ser Glu Asp Val Glu
305                 310                 315                 320

Glu Glu Ser Gly Asp Gly Arg Lys Glu Ala Gly Pro Ser Arg Thr Gly
            325                 330                 335

Leu Gly Ser Lys Arg Ser Arg Ser Ala Glu Val His Asn Leu Ser Glu
            340                 345                 350

Arg Arg Arg Arg Asp Arg Ile Asn Glu Lys Met Arg Ala Leu Gln Glu
            355                 360                 365

Leu Ile Pro Asn Cys Asn Lys Val Asp Lys Ala Ser Met Leu Asp Glu
            370                 375                 380

Ala Ile Glu Tyr Leu Lys Ser Leu Gln Leu Gln Val Gln Ile Met Ser
385                 390                 395                 400

Met Ala Ser Gly Tyr Tyr Leu Pro Pro Ala Val Met Phe Pro Pro Gly
            405                 410                 415

Met Gly His Tyr Pro Ala Ala Ala Ala Met Ala Met Gly Met Gly
            420                 425                 430

Met Pro Tyr Ala Met Gly Leu Pro Asp Leu Ser Arg Gly Gly Ser Ser
            435                 440                 445

Val Asn His Gly Pro Gln Phe Gln Val Ser Gly Met Gln Gln Gln Pro
            450                 455                 460

Val Ala Met Gly Ile Pro Arg Val Ser Gly Gly Ile Phe Ala Gly
465                 470                 475                 480

Ser Ser Thr Ile Gly Asn Gly Ser Thr Arg Asp Leu Ser Gly Ser Lys
            485                 490                 495

Asp Gln Thr Thr Thr Asn Asn Asn Ser Asn Leu Lys Pro Ile Lys Arg
            500                 505                 510

Lys Gln Gly Ser Ser Asp Gln Phe Cys Gly Ser Ser
            515                 520

<210> SEQ ID NO 7
<211> LENGTH: 363
<212> TYPE: PRT
<213> ORGANISM: Arabidopsis thaliana

<400> SEQUENCE: 7

Met Met Phe Leu Pro Thr Asp Tyr Cys Cys Arg Leu Ser Asp Gln Glu
1               5                   10                  15

Tyr Met Glu Leu Val Phe Glu Asn Gly Gln Ile Leu Ala Lys Gly Gln
            20                  25                  30

Arg Ser Asn Val Ser Leu His Asn Gln Arg Thr Lys Ser Ile Met Asp
        35                  40                  45

Leu Tyr Glu Ala Glu Tyr Asn Glu Asp Phe Met Lys Ser Ile Ile His
    50                  55                  60

Gly Gly Gly Gly Ala Ile Thr Asn Leu Gly Asp Thr Gln Val Val Pro
65                  70                  75                  80

Gln Ser His Val Ala Ala Ala His Glu Thr Asn Met Leu Glu Ser Asn
                85                  90                  95

Lys His Val Asp Asp Ser Glu Thr Leu Lys Ala Ser Ser Lys Arg
            100                 105                 110

Met Met Val Asp Tyr His Asn Arg Lys Lys Ile Lys Phe Ile Pro Pro
        115                 120                 125

Asp Glu Gln Ser Val Val Ala Asp Arg Ser Phe Lys Leu Gly Phe Asp
    130                 135                 140

Thr Ser Val Gly Phe Thr Glu Asp Ser Glu Gly Ser Met Tyr Leu
145                 150                 155                 160

Ser Ser Ser Leu Asp Asp Glu Ser Asp Ala Arg Pro Gln Val Pro
                165                 170                 175

Ala Arg Thr Arg Lys Ala Leu Val Lys Arg Lys Arg Asn Ala Glu Ala
        180                 185                 190

Tyr Asn Ser Pro Glu Arg Asn Gln Arg Asn Asp Ile Asn Lys Lys Met
    195                 200                 205

Arg Thr Leu Gln Asn Leu Leu Pro Asn Ser His Lys Asp Asp Asn Glu
210                 215                 220

Ser Met Leu Asp Glu Ala Ile Asn Tyr Met Thr Asn Leu Gln Leu Gln
225                 230                 235                 240

Val Gln Met Met Thr Met Gly Asn Arg Phe Val Thr Pro Ser Met Met
                245                 250                 255

Met Pro Leu Gly Pro Asn Tyr Ser Gln Met Gly Leu Ala Met Gly Val
            260                 265                 270

Gly Met Gln Met Gly Glu Gln Gln Phe Leu Pro Ala His Val Leu Gly
        275                 280                 285

Ala Gly Leu Pro Gly Ile Asn Asp Ser Ala Asp Met Leu Arg Phe Leu
    290                 295                 300

Asn His Pro Gly Leu Met Pro Met Gln Asn Ser Ala Pro Phe Ile Pro
305                 310                 315                 320

Thr Glu Asn Cys Ser Pro Gln Ser Val Pro Pro Ser Cys Ala Ala Phe
                325                 330                 335

Pro Asn Gln Ile Pro Asn Pro Asn Ser Leu Ser Asn Leu Asp Gly Ala
            340                 345                 350

Thr Leu His Lys Lys Ser Arg Lys Thr Asn Arg
        355                 360

```
<210> SEQ ID NO 8
<211> LENGTH: 430
<212> TYPE: PRT
<213> ORGANISM: Arabidopsis thaliana

<400> SEQUENCE: 8

Met Glu His Gln Gly Trp Ser Phe Glu Glu Asn Tyr Ser Leu Ser Thr
1               5                   10                  15

Asn Arg Arg Ser Ile Arg Pro Gln Asp Glu Leu Val Glu Leu Leu Trp
            20                  25                  30

Arg Asp Gly Gln Val Val Leu Gln Ser Gln Thr His Arg Glu Gln Thr
        35                  40                  45

Gln Thr Gln Lys Gln Asp His His Glu Glu Ala Leu Arg Ser Ser Thr
    50                  55                  60

Phe Leu Glu Asp Gln Glu Thr Val Ser Trp Ile Gln Tyr Pro Pro Asp
65                  70                  75                  80

Glu Asp Pro Phe Glu Pro Asp Asp Phe Ser Ser His Phe Phe Ser Thr
                85                  90                  95

Met Asp Pro Leu Gln Arg Pro Thr Ser Glu Thr Val Lys Pro Lys Ser
            100                 105                 110

Ser Pro Glu Pro Pro Gln Val Met Val Lys Pro Lys Ala Cys Pro Asp
        115                 120                 125

Pro Pro Pro Gln Val Met Pro Pro Lys Phe Arg Leu Thr Asn Ser
    130                 135                 140

Ser Ser Gly Ile Arg Glu Thr Glu Met Glu Gln Tyr Ser Val Thr Thr
145                 150                 155                 160

Val Gly Pro Ser His Cys Gly Ser Asn Pro Ser Gln Asn Asp Leu Asp
                165                 170                 175

Val Ser Met Ser His Asp Arg Ser Lys Asn Ile Glu Glu Lys Leu Asn
            180                 185                 190

Pro Asn Ala Ser Ser Ser Ser Gly Gly Ser Ser Gly Cys Ser Phe Gly
        195                 200                 205

Lys Asp Ile Lys Glu Met Ala Ser Gly Arg Cys Ile Thr Thr Asp Arg
    210                 215                 220

Lys Arg Lys Arg Ile Asn His Thr Asp Glu Ser Val Ser Leu Ser Asp
225                 230                 235                 240

Ala Ile Gly Asn Lys Ser Asn Gln Arg Ser Gly Ser Asn Arg Arg Ser
                245                 250                 255

Arg Ala Ala Glu Val His Asn Leu Ser Glu Arg Arg Arg Arg Asp Arg
            260                 265                 270

Ile Asn Glu Arg Met Lys Ala Leu Gln Glu Leu Ile Pro His Cys Ser
        275                 280                 285

Lys Thr Asp Lys Ala Ser Ile Leu Asp Glu Ala Ile Asp Tyr Leu Lys
    290                 295                 300

Ser Leu Gln Leu Gln Leu Gln Val Met Trp Met Gly Ser Gly Met Ala
305                 310                 315                 320

Ala Ala Ala Ala Ser Ala Pro Met Met Phe Pro Gly Val Gln Pro Gln
                325                 330                 335

Gln Phe Ile Arg Gln Ile Gln Ser Pro Val Gln Leu Pro Arg Phe Pro
            340                 345                 350

Val Met Asp Gln Ser Ala Ile Gln Asn Asn Pro Gly Leu Val Cys Gln
        355                 360                 365

Asn Pro Val Gln Asn Gln Ile Ile Ser Asp Arg Phe Ala Arg Tyr Ile
```

```
               370                 375                 380
Gly Gly Phe Pro His Met Gln Ala Ala Thr Gln Met Gln Pro Met Glu
385                 390                 395                 400

Met Leu Arg Phe Ser Ser Pro Ala Gly Gln Gln Ser Gln Gln Pro Ser
                405                 410                 415

Ser Val Pro Thr Lys Thr Thr Asp Gly Ser Arg Leu Asp His
            420                 425                 430

<210> SEQ ID NO 9
<211> LENGTH: 416
<212> TYPE: PRT
<213> ORGANISM: Arabidopsis thaliana

<400> SEQUENCE: 9

Met Glu Ala Lys Pro Leu Ala Ser Ser Ser Glu Pro Asn Met Ile
1               5                   10                  15

Ser Pro Ser Ser Asn Ile Lys Pro Lys Leu Lys Asp Glu Asp Tyr Met
                20                  25                  30

Glu Leu Val Cys Glu Asn Gly Gln Ile Leu Ala Lys Ile Arg Arg Pro
            35                  40                  45

Lys Asn Asn Gly Ser Phe Gln Lys Gln Arg Arg Gln Ser Leu Leu Asp
50                  55                  60

Leu Tyr Glu Thr Glu Tyr Ser Glu Gly Phe Lys Lys Asn Ile Lys Ile
65                  70                  75                  80

Leu Gly Asp Thr Gln Val Val Pro Val Ser Gln Ser Lys Pro Gln Gln
                85                  90                  95

Asp Lys Glu Thr Asn Glu Gln Met Asn Asn Lys Lys Lys Leu Lys
            100                 105                 110

Ser Ser Lys Ile Glu Phe Glu Arg Asn Val Ser Lys Ser Asn Lys Cys
            115                 120                 125

Val Glu Ser Ser Thr Leu Ile Asp Val Ser Ala Lys Gly Pro Lys Asn
130                 135                 140

Val Glu Val Thr Thr Ala Pro Pro Asp Glu Gln Ser Ala Ala Val Gly
145                 150                 155                 160

Arg Ser Thr Glu Leu Tyr Phe Ala Ser Ser Lys Phe Ser Arg Gly
                165                 170                 175

Thr Ser Arg Asp Leu Ser Cys Cys Ser Leu Lys Arg Lys Tyr Gly Asp
            180                 185                 190

Ile Glu Glu Glu Ser Thr Tyr Leu Ser Asn Asn Ser Asp Asp Glu
            195                 200                 205

Ser Asp Asp Ala Lys Thr Gln Val His Ala Arg Thr Arg Lys Pro Val
210                 215                 220

Thr Lys Arg Lys Arg Ser Thr Glu Val His Lys Leu Tyr Glu Arg Lys
225                 230                 235                 240

Arg Arg Asp Glu Phe Asn Lys Lys Met Arg Ala Leu Gln Asp Leu Leu
                245                 250                 255

Pro Asn Cys Tyr Lys Asp Asp Lys Ala Ser Leu Leu Asp Glu Ala Ile
            260                 265                 270

Lys Tyr Met Arg Thr Leu Gln Leu Gln Val Gln Met Met Ser Met Gly
            275                 280                 285

Asn Gly Leu Ile Arg Pro Pro Thr Met Leu Pro Met Gly His Tyr Ser
290                 295                 300

Pro Met Gly Leu Gly Met His Met Gly Ala Ala Thr Pro Thr Ser
305                 310                 315                 320
```

```
Ile Pro Gln Phe Leu Pro Met Asn Val Gln Ala Thr Gly Phe Pro Gly
                325                 330                 335

Met Asn Asn Ala Pro Pro Gln Met Leu Ser Phe Leu Asn His Pro Ser
            340                 345                 350

Gly Leu Ile Pro Asn Thr Pro Ile Phe Ser Pro Leu Glu Asn Cys Ser
        355                 360                 365

Gln Pro Phe Val Val Pro Ser Cys Val Ser Gln Thr Gln Ala Thr Ser
    370                 375                 380

Phe Thr Gln Phe Pro Lys Ser Ala Ser Ala Ser Asn Leu Glu Asp Ala
385                 390                 395                 400

Met Gln Tyr Arg Gly Ser Asn Gly Phe Ser Tyr Tyr Arg Ser Pro Asn
                405                 410                 415

<210> SEQ ID NO 10
<211> LENGTH: 30
<212> TYPE: DNA
<213> ORGANISM: Artificial
<220> FEATURE:
<223> OTHER INFORMATION: Synthetic DNA linker sequence

<400> SEQUENCE: 10
gatagtgctg gtagtgctgg tagtgctggt                                        30

<210> SEQ ID NO 11
<211> LENGTH: 10
<212> TYPE: PRT
<213> ORGANISM: Artificial
<220> FEATURE:
<223> OTHER INFORMATION: Synthetic polypeptide linker sequence

<400> SEQUENCE: 11

Asp Ser Ala Gly Ser Ala Gly Ser Ala Gly
1               5                   10

<210> SEQ ID NO 12
<211> LENGTH: 60
<212> TYPE: DNA
<213> ORGANISM: Artificial
<220> FEATURE:
<223> OTHER INFORMATION: Synthetic DNA linker sequence

<400> SEQUENCE: 12
agtgctggtg gtagtgctgg tggtagtgct ggtggtagtg ctggtggtag tgctggtggt        60

<210> SEQ ID NO 13
<211> LENGTH: 20
<212> TYPE: PRT
<213> ORGANISM: Artificial
<220> FEATURE:
<223> OTHER INFORMATION: Synthetic polypeptide linker sequence

<400> SEQUENCE: 13

Ser Ala Gly Gly Ser Ala Gly Gly Ser Ala Gly Gly Ser Ala Gly Gly
1               5                   10                  15

Ser Ala Gly Gly
            20

<210> SEQ ID NO 14
<211> LENGTH: 10
<212> TYPE: PRT
<213> ORGANISM: Artificial
<220> FEATURE:
<223> OTHER INFORMATION: Synthetic polypeptide for Hras palmitoylation
      CaaX sequence
```

<400> SEQUENCE: 14

Gly Cys Met Ser Cys Lys Cys Val Leu Ser
1               5                   10

<210> SEQ ID NO 15
<211> LENGTH: 30
<212> TYPE: DNA
<213> ORGANISM: Artificial
<220> FEATURE:
<223> OTHER INFORMATION: Synthetic DNA for Hras palmitoylation CaaX
      sequence

<400> SEQUENCE: 15
ggctgcatga gctgcaagtg tgtgctctcc                                    30

<210> SEQ ID NO 16
<211> LENGTH: 14
<212> TYPE: PRT
<213> ORGANISM: Artificial
<220> FEATURE:
<223> OTHER INFORMATION: Synthetic polypeptide for Kras4B polybasic CaaX
      terminus sequence

<400> SEQUENCE: 16

Lys Lys Lys Lys Lys Lys Ser Lys Thr Lys Cys Val Ile Met
1               5                   10

<210> SEQ ID NO 17
<211> LENGTH: 45
<212> TYPE: DNA
<213> ORGANISM: Artificial
<220> FEATURE:
<223> OTHER INFORMATION: Synthetic DNA for Kras4B polybasic CaaX
      terminus sequence

<400> SEQUENCE: 17
ggtaaaaaga agaaaaagaa gtcaaagaca aagtgtgtaa ttatg                   45

<210> SEQ ID NO 18
<211> LENGTH: 14
<212> TYPE: PRT
<213> ORGANISM: Artificial
<220> FEATURE:
<223> OTHER INFORMATION: Synthetic polypeptide for Lyn kinase NT13
      plasma membrane targeting sequence

<400> SEQUENCE: 18

Met Gly Cys Ile Lys Ser Lys Gly Lys Asp Ser Ala Gly Ala
1               5                   10

<210> SEQ ID NO 19
<211> LENGTH: 42
<212> TYPE: DNA
<213> ORGANISM: Artificial
<220> FEATURE:
<223> OTHER INFORMATION: Synthetic DNA for Lyn kinase NT13 plasma
      membrane targeting sequence

<400> SEQUENCE: 19
atgggatgta taaaatcaaa agggaaagac agcgcgggag ca                      42